(12) United States Patent
Saito et al.

(10) Patent No.: US 6,384,063 B1
(45) Date of Patent: May 7, 2002

(54) COMPOUND HAVING EFFECT OF PROMOTING NEURON DIFFERENTIATION

(75) Inventors: Seiichi Saito, Kashiwa; Masashi Nagai, Tanashi; Tomio Morino, Omiya; Tsugio Tomiyoshi, Tokyo; Takaaki Nishikiori, Yono; Atsushi Kuwahara, Neyagawa; Takamichi Sato, Yono; Takashi Harada, Tokyo, all of (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/463,354

(22) PCT Filed: Jul. 24, 1998

(86) PCT No.: PCT/JP98/03313

§ 371 Date: Mar. 31, 2000

§ 102(e) Date: Mar. 31, 2000

(87) PCT Pub. No.: WO99/05091

PCT Pub. Date: Feb. 4, 1999

(30) Foreign Application Priority Data

| Jul. 25, 1997 | (JP) | ............................................. 9-213896 |
| Jul. 30, 1997 | (JP) | ............................................. 9-218370 |
| Jul. 30, 1997 | (JP) | ............................................. 9-218371 |
| Jul. 30, 1997 | (JP) | ............................................. 9-218372 |
| Aug. 29, 1997 | (JP) | ............................................. 9-247534 |
| Jan. 16, 1998 | (JP) | ........................................... 10-018304 |
| Jan. 16, 1998 | (JP) | ........................................... 10-018305 |
| Jan. 16, 1998 | (JP) | ........................................... 10-018306 |
| Jan. 16, 1998 | (JP) | ........................................... 10-018307 |

(51) Int. Cl.[7] ........................ A61K 31/44; C07D 213/56
(52) U.S. Cl. ...................................... 514/355; 546/316
(58) Field of Search ........................... 514/355; 546/316

(56) References Cited

U.S. PATENT DOCUMENTS

| 3,755,118 | A |   | 8/1973 | Partridge, Jr. et al. .. 204/158 R |
| 5,332,751 | A | * | 7/1994 | Yoshino et al. .............. 514/355 |
| 6,194,421 | B1 | * | 2/2001 | Cohen et al. ................ 514/277 |

FOREIGN PATENT DOCUMENTS

| HU | P9402558 | 11/1994 |
| JP | 57-77669 | 5/1982 |
| JP | 62-149666 | 7/1987 |
| JP | 5-238978 | 9/1993 |
| WO | 93/17683 | 9/1993 |
| WO | 97/28114 | 8/1997 |

OTHER PUBLICATIONS

Copy of the Hungarian Patent Office Novelty Search Report dated Mar. 22, 2001.

Kuliev, A.M., et al., "Synthesis of aminomethylthiomethyl delivatives of cyclopentanone and cyclohexanone and conversion of the resulting substances.", Zh. Org. Khim., 1977, vol. 13, No. 10, p. 1193–1195.

Takamatsu, Y., et al., "Inhibition of human hepatic glutathione S–transferase isozymes by ethacrynic acid and its metabolites.", Toxicol. Lett., 1992, vol. 62, No. 2–3, p. 241–245.

(List continued on next page.)

Primary Examiner—Ralph Gitomer
Assistant Examiner—Devesh Khare
(74) Attorney, Agent, or Firm—Nields & Lemack

(57) ABSTRACT

A novel cystacycline derivative which has an excellent effect of promoting the differentiation of neurons and is useful as a remedy for central nervous system disorders, a remedy for peripheral nerve disorders, etc.

12 Claims, 3 Drawing Sheets

OTHER PUBLICATIONS

Copy of the International Search Report dated Oct. 27, 1998.
Database Beilstein Online! Beilstein Institute for Organic Chemistry, Frankfurt/Main, DE; Database accession No. 4459857; XP-002174252 Abstract.
Database Beilstein Online! Beilstein Institute for Organic Chemistry, Frankfurt/Main, DE; Database accession No. 4493886;XP-002174253 Abstract.
Database Beilstein Online! Beilstein Institute for Organic Chemistry, Frankfurt/Main, DE; Database accession No. 2024214; XP-002174254 Abstract.
Database Beilstein Online! Beilstein Institute for Organic Chemistry, Frankfurt/Main, DE; Database accession No. 3050771; XP-002174255 Abstract.
Database Beilstein Online! Beilstein Institute for Organic Chemistry, Frankfurt/Main, DE; Database accession No. 4673843; XP-002174256 Abstract.
Database Beilstein Online! Beilstein Institute for Organic Chemistry, Frankfurt/Main, DE; Database accession No. 4412465; XP-002174257 Abstract.
Database Beilstein Online! Beilstein Institute for Organic Chemistry, Frankfurt/Main, DE; Database accession No. 1935567; XP-002174258 Abstract.

Database Beilstein Online! Beilstein Institute for Organic Chemistry, Frankfurt/Main, DE; Database accession No. 3107650; XP-002174259 Abstract.

Database Beilstein Online! Beilstein Institute for Organic Chemistry, Frankfurt/Main, DE; Database accession No. 3978182; XP-002174260 Abstract.

Database Beilstein Online! Beilstein Institute for Organic Chemistry, Frankfurt/Main, DE; Database accession No. 1142839; XP-002174261 Abstract.

Database Beilstein Online! Beilstein Institute for Organic Chemistry, Frankfurt/Main, DE; Database accession No.2359784; XP-002174262 Abstract.

Marian Mikoljczyk et al.:"Total synthesis of (+-)-sarkomycin"TETRAHEDRON., vol.45, No. 22, 1989, pp. 7023-30, XP-002174251.

Copy of the Supplemental European Search Report dated Aug. 8, 2001.

* cited by examiner

COMPOUND HAVING EFFECT OF PROMOTING NEURON DIFFERENTIATION

TECHNICAL FIELD

The present invention relates to novel compounds having a neuron differentiation promoting activity and pharmaceutical use thereof.

BACKGROUND ART

Neurotrophic factors are proteinaceous compounds that participate in differentiation induction of neurons and in maintainance of the existence and survival of nerve cells. Nerve growth factors (hereinafter often abbreviated as NGF) are known to be representative of such compounds (Ann. Neuro., 10, 499–503 (1981)). It is manifested that NGF is deeply involved in the differentiation, existence maintenance and repair of neurons in both the central and peripheral nervous systems.

Damages of nerves caused by aging, internal and external factors often develop pathological symptoms. Such damages are found to cause, in the central nervous system, Alzheimer's disease, dementia induced by cerebro-vascular disorders, disturbance of consciousness due to cerebral contusion, tremor or muscle rigidity by Parkinson's disease, etc. It is also known that damages in the peripheral nervous system are induced by amyotrophic lateral sclerosis, spinal muscle atrophy, motor function disturbances due to neuron damages accompanied by accidents, etc., and that neuropathies are induced by diabetes mellitus, uremia, vitamin B1 or B12 deficiency, chronic liver disease, sarcoidosis, amyloidosis, hypothyrea, cancer, angiopathy, Sjögren symptoms, immunopathy accompanied by infections, hereditary disease, physical compression, drugs (carcinostatic agents, tuberculostatic agents, anti-epileptic agents, etc.) or intoxication (arsenic, thallium, carbon disulfide, etc.); in more detail, see RINSHO KENSA (Clinical Test), 40, 760–766 (1996). It was the recognition in the art that when neurons suffer irreversible damages from these disorders, it was difficult to regenerate and repair the damaged neurons. However, on the hypothesis that neuropathy could be treated if the neurotrophic factors act on neurons, development of neurotrophic factors as medicaments against neuropathy has been made. (Science, 264, 772–774 (1994)). For instance, clinical trial of NGF is in progress against Alzheimer's disease, neural damages or spinal injuries.

NGF is a series of proteins having approximately 50,000 molecular weight. For the treatment of neuropathy, it generally takes a long period of time. For these reasons, it is difficult to develop efficient administration and pharmaceutical formulation. Gene therapy namely induction of NGF gene, is also another choice for the treatment but its therapeutic effect is yet unclear.

It is known that when NGF is present, PC 12 cells—which are the established cell line cloned from rat adrenal medulla pheochromocytoma—terminate cell proliferation and differentiate into neuron-like cells with neurites. This procedure enables to screen an effective substance having a NGF-like neuron differentiation promoting activity. For example, antibiotic staurosporin was found to have the PC 12 cell differentiation promoting activity (SHINKEI KAGAKU, 26, 200–220 (1987)). A similar differentiation promoting activity was recently observed in a biological active compound NK175203 (hereinafter referred to as cystacyclin) which was produced from Streptomyces sp. NK175203 strain FERM BP-4372 (WO 95/31992).

However, the toxicity and pharmacokinetics of staurosporin m vivo make its application as a medicament difficult. It has thus been strongly desired to develop a low molecular weight compound that exhibits a neuron differentiation promoting activity, is low toxic and is readily prepared synthetically.

DISCLOSURE OF INVENTION

The present inventors have made extensive investigations on cystacycline derivatives and as a result, have found novel compounds represented by general formulas [1A], [1B], [1C], [1D], [1E] and [1F] and pharmacologically acceptable salts thereof. The present invention has thus been accomplished. The present invention relates to the following compounds and compositions comprising the same.

1) A cyclopentanone derivative represented by a formula [1A]:

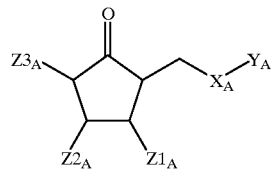

[1A]

wherein $X_A$ is O, S, SO, $SO_2$ or NH;

$Y_A$ is a straight or branched aliphatic hydrocarbon group having 1 to 20 carbon atoms, which may be substituted or unsubstituted, or a substituted or unsubstituted aromatic hydrocarbon group or monocyclic aromatic heterocyclic ring having 3 to 6 carbon atoms;

each of $Z1_A$, $Z2_A$ and $Z3_A$, which may be the same or different and independently represents carboxy or a group derived therefrom, an unsubstituted or substituted alkyl having 1 to 4 carbon atoms, hydroxy or a group derived therefrom, amino or a group derived therefrom, sulfonate or a group derived therefrom, phosphate or a group derived therefrom, a monocyclic heteroaryl, a halogen or hydrogen; or $Z2_A$ and $Z3_A$ are combined together to form a substituted or unsubstituted aromatic hydrocarbon or aromatic heterocyclic ring; and, $Z1_A$ is carboxy or a group derived therefrom, an unsubstituted or substituted alkyl having 1 to 4 carbon atoms, hydroxy or a group derived therefrom, amino or a group derived therefrom, a halogen or hydrogen, with the proviso that, when $Z2_A$ and $Z3_A$ are both hydrogen, $Z1_A$ is hydroxy or a group derived therefrom, amino or a group derived therefrom, sulfonate or a monocyclic aromatic heterocyclic ring, a halogen or hydrogen, and $Y_A$ is a substituted or unsubstituted straight or branched aliphatic hydrocarbon group having 1 to 6 carbon atoms;

with the proviso that (1) through (7) are excluded:
(1) when $Z1_A$ and $Z2_A$ are hydrogen, $X_A$ is S, $Y_A$ is methyl or benzyl and, $Z3_A$ is methoxycarbonyl,
(2) when $Z1_A$ and $Z2_A$ are hydrogen, $X_A$ is O or N, $Y_A$ is benzyl and, $Z3_A$ is carboxy, methoxycarbonyl or ethoxycarbonyl;
(3) $X_A$ is N or O, $Z1_A$ and $Z3_A$ are hydrogen and, $Z2_A$ is carboxy or methoxycarbonyl;
(4) $X_A$ is O, $Z1_A$ is hydroxy or a group derived therefrom, $Z2_A$ is hydrogen and, $Z3_A$ is amino or a group derived therefrom;

(5) $X_A$ is S, $Y1_A$ is phenyl, $Z1_A$ is dimethoxymethyl and, $Z2_A$ and $Z3_A$ are hydrogen;
(6) $X_A$ is O, $Y1_A$ is methyl, $Z1_A$ is 1-methoxy-1-phenylthiomethyl and, $Z2_A$ and $Z3_A$ are hydrogen;
(7) $Z1_A$ is S, SO or $SO_2$, $Z2_A$ is hydroxy or a group derived therefrom and, $Z3_A$ is hydrogen;

or a pharmacologically acceptable salt thereof;

a 2,3-di-substituted cyclopentanone derivative of formula [1B]:

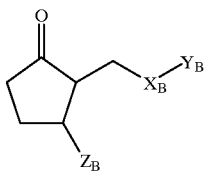

[1B]

wherein:
$X_B$ is O, S, SO, $SO_2$ or NH;
$Y_B$ is:
  an unsubstituted or substituted straight or branched aliphatic hydrocarbon group having 7 to 20 carbon atoms,
  a straight or branched aliphatic hydrocarbon group having 1 to 6 carbon atoms, wherein:
    at least one hydrogen is substituted with COW1 (wherein W1 is an unsubstituted or substituted aromatic heterocyclic ring or saturated heterocyclic ring) and, at least one hydrogen may be further substituted with a group derived from amino; or,
    at least one hydrogen is substituted with NHCOV1 (wherein V1 is an alkyl having 2 to 5 carbon atoms containing 4 to 11 halogen atoms) and at least one hydrogen may be further substituted with carboxy or a group derived therefrom; or,
    at least one hydrogen is substituted with a substituted or unsubstituted monocyclic aromatic heterocyclic ring and, at least one hydrogen may be further substituted with amino or a group derived therefrom; or,
  a substituted or unsubstituted aromatic hydrocarbon group or monocyclic aromatic heterocyclic ring having 3 to 6 carbon atoms;
$Z_B$ is carboxy or a group derived therefrom, sulfonate or a group derived therefrom, phosphate or a group derived therefrom, an unsubstituted or substituted alkyl having 1 to 4 carbon atoms, hydroxy, OR1 (wherein R1 is an unsubstituted or substituted alkyl having 1 to 4 carbon atoms or, an unsubstituted or substituted acyl having 1 to 5 carbon atoms), NHCOR2 (wherein R2 is an unsubstituted or substituted alkyl having 1 to 4 carbon atoms), $NHSO_2R2'$ (wherein R2' is an unsubstituted or substituted alkyl having 1 to 4 carbon atoms or phenyl), a monocyclic aromatic heterocyclic ring, a halogen or hydrogen;

or a pharmacologically acceptable salt thereof;

a cyclopentenone derivative of formula [1C]:

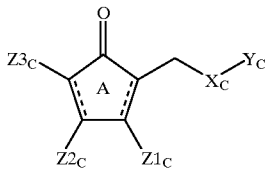

[1C]

wherein:
ring A has one double bond conjugated with oxo;
$X_c$ is O, S, SO, $SO_2$ or NH;
$Y_c$ is a substituted or unsubstituted aliphatic hydrocarbon group having 1 to 6 carbon atoms or a substituted or unsubstituted aromatic hydrocarbon group or monocyclic aromatic heterocyclic ring having 3 to 6 carbon atoms;
  each of $Z1_c$, $Z2_c$ and $Z3_c$, which may be the same or different and independently represents carboxy or a group derived therefrom, hydroxy or a group derived therefrom, amino or a group derived therefrom, a substituted or unsubstituted alkyl or alkenyl having 1 to 4 carbon atoms, a monocyclic aromatic heterocyclic ring, a halogen atom or hydrogen;
  with the proviso that, when $X_c$ is O or NH, $Z1_c$ and $Z3_c$ are not hydrogen and, $Z2_c$ is not hydrogen or, hydroxy or a group derived therefrom;

or a pharmacologically acceptable salt thereof;

a ketone derivative of formula [1D]:

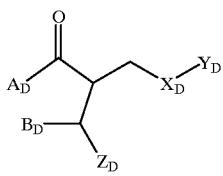

[1D]

wherein:
$A_D$ is an unsubstituted or substituted aliphatic hydrocarbon group having 1 to 4 carbon atoms, an unsubstituted or substituted aromatic hydrocarbon, heterocyclic ring or saturated heterocyclic ring;
$B_D$ is hydrogen or an unsubstituted or substituted aliphatic hydrocarbon group having 1 to 4 carbon atoms; or,
$A_D$ and $B_D$ are combined together to form an unsubstituted or substituted cycloalkan-1-one ring having 3 to 7 carbon atoms (except for 5 carbon atoms);
$X_D$ is O, S, SO, $SO_2$ or NH;
$Y_D$ is a substituted or unsubstituted aliphatic hydrocarbon group having 1 to 6 carbon atoms or a substituted or unsubstituted aromatic hydrocarbon group or monocyclic aromatic heterocyclic ring having 3 to 6 carbon atoms;
$Z_D$ is carboxy or a group derived therefrom, an unsubstituted or substituted alkyl or alkenyl having 1 to 4 carbon atoms, hydroxy or a group derived therefrom, amino or a group derived therefrom, sulfonate or a group derived therefrom or, phosphate or a group derived therefrom, a monocyclic aromatic heterocyclic ring, a halogen or hydrogen;

with the proviso that, when $A_D$ and $B_D$ are combined together to form a cyclobutane ring, the following (1) through (4) are excluded:
(1) $X_D$ is O, $Y_D$ is methyl, n-octyl or n-hexadecyl and, $Z_D$ is methoxycarbonyl;
(2) $X_D$ is O, $Y_D$ is benzyl and, $Z_D$ is benzyloxylmethyl;
(3) $X_D$ is O, $Y_D$ is p-methoxybenzyl and, $Z_D$ is p-methoxybenzyloxymethyl; and,
(4) $X_D$ is O, $Y_D$ is trityl and $Z_D$ is trityloxymethyl or, when $A_D$ is an unsubstituted benzene ring and $B_D$ is hydrogen, $X_D$ is S, $Y_D$ is methyl, ethyl or isopropyl and $Z_D$ is carboxy;

or a pharmacologically acceptable salt thereof;

a compound of formula [1E]:

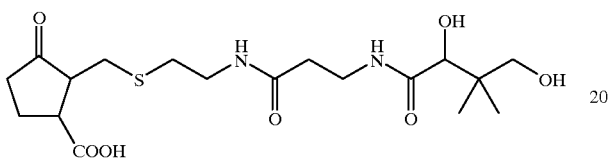

[1E]

or a pharmacologically acceptable salt thereof; or, a β-di-substituted aminoketone derivative of formula [1F]:

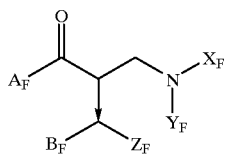

[1F]

wherein:
$A_F$ is an unsubstituted or substituted aliphatic hydrocarbon group having 1 to 4 carbon atoms or, an unsubstituted or substituted aromatic hydrocarbon ring, aromatic heterocyclic ring or saturated heterocyclic ring;

$B_F$ is hydrogen or, an unsubstituted or substituted aliphatic hydrocarbon group having 1 to 4 carbon atoms; or, $A_F$ and $B_F$ are combined together to form an unsubstituted or substituted cycloalkan-1-one ring having 3 to 7 carbon atoms or, to form a cycloalkan-1-one ring having 3 to 7 carbon atoms and fused with an aromatic hydrocarbon or a aromatic heterocyclic ring;

each of $X_F$ and $Y_F$ is an unsubstituted or substituted straight or branched aliphatic hydrocarbon group having 1 to 10 carbon atoms or, $X_F$ and $Y_F$ are bound to each other directly or via a hetero atom to form an unsubstituted or substituted heterocyclic ring;

$Z_F$ is carboxy or a group derived therefrom, an unsubstituted or substituted alkyl or alkenyl having 1 to 4 carbon atoms, hydroxy or a group derived therefrom, amino or a group derived therefrom, sulfonate or a group derived therefrom, phosphate or a group derived therefrom, a monocyclic aromatic heterocyclic ring or a halogen;

with the proviso that, when $A_F$ is an unsubstituted benzene ring, excluded are those wherein $B_F$ is hydrogen, $X_F$ and $Y_F$ are bound to each other directly to form a piperidine ring and, $Z_F$ is carboxy; or a pharmacologically acceptable salt thereof.

2) A cyclopentanone derivative of formula [1A] or a pharmacologically acceptable salt thereof, according to 1) above, wherein:

$X_A$ is S, O, S or SO;

$Y_A$ is a straight or branched aliphatic hydrocarbon group having 1 to 20 carbon atoms (wherein at least one hydrogen atom is substituted with carboxy or a group derived therefrom, or amino or a group derived therefrom);

each of $Z1_A$, $Z2_A$ and $Z3_A$, which may be the same or different and independently represents carboxy or a group derived therefrom, an unsubstituted or substituted alkyl having 1 to 4 carbon atoms, hydroxy or a group derived therefrom, amino or a group derived therefrom, a monocyclic aromatic heterocyclic ring, a halogen or hydrogen; or $Z2_A$ and $Z3_A$ are combined together to form a substituted or unsubstituted aromatic hydrocarbon or a aromatic heterocyclic ring; and, $Z1_A$ is carboxy or a group derived therefrom, an unsubstituted or substituted alkyl having 1 to 4 carbon atoms, hydroxy or a group derived therefrom, amino or a group derived therefrom, a halogen or hydrogen.

3) A cyclopentanone derivative of formula [1A] or a pharmacologically acceptable salt thereof, according to 2) described above, wherein:

$X_A$ is S;

$Y_A$ is a straight or branched aliphatic hydrocarbon group having 1 to 6 carbon atoms, wherein;

at least one hydrogen atom is substituted with carboxy, COOR1 (wherein R1 is a substituted or unsubstituted alkyl, alkenyl or alkynyl having 1 to 4 carbon atoms), COW1 (wherein W1 is a heterocyclic ring unsubstituted or substituted with carboxy or a group derived therefrom) or NR2R3 (wherein each of R2 and R3, which may be different or the same independently, represents hydrogen, an unsubstituted or substituted alkyl having 1 to 4 carbon atoms or, an unsubstituted or substituted acyl having 1 to 5 carbon atoms);

each of $Z1_A$, $Z2_A$ and $Z3_A$, which may be the same or different and independently represents carboxy, COOR4 (wherein R4 is an unsubstituted or substituted alkyl having 1 to 4 carbon atoms), CONR5R6 (wherein each of R5 and R6, which may be different or the same independently, represents hydrogen or a substituted or unsubstituted alkyl having 1 to 4 carbon atoms), cyano, hydroxy, OR7 (wherein R7 is an unsubstituted or substituted alkyl having 1 to 4 carbon atoms or, an unsubstituted or substituted acyl having 1 to 5 carbon atoms), NR8R9 (wherein each of R8 and R9, which may be the same or different and independently represents hydrogen, an unsubstituted or substituted alkyl having 1 to 4 carbon atoms or, an unsubstituted or substituted acyl having 1 to 5 carbon atoms), CH$_2$OR10 (wherein R10 is hydrogen, an unsubstituted or substituted alkyl having 1 to 4 carbon atoms or, an unsubstituted or substituted acyl having 1 to 5 carbon atoms), chlorine, fluorine or hydrogen; or, $Z2_A$ and $Z3_A$ are combined together to form a substituted or unsubstituted aromatic hydrocarbon; and, $Z1_A$ is carboxy, COOR4 (wherein R4 is an unsubstituted or substituted alkyl having 1 to 4 carbon atoms), CONR5R6 (wherein each of R5 and R6, which may be different or the same independently, represents hydrogen or a substituted or unsubstituted alkyl having 1 to 4 carbon atoms), cyano, hydroxy, OR7 (wherein R7 is an unsubstituted or substituted alkyl having 1 to 4 carbon atoms or, an unsubstituted or substituted acyl having 1 to 5 carbon atoms), NR8R9 (wherein each of R8 and R9 which may be the same or different and independently represents hydrogen, an unsubstituted or substituted alkyl having 1 to 4 carbon atoms or, an unsubstituted or substituted acyl having 1 to 5 carbon atoms), $CH_2OR10$ (wherein R10 is hydrogen, an unsubstituted or substituted alkyl having 1 to 4 carbon atoms or, an unsubstituted or substituted acyl having 1 to 5 carbon atoms), chlorine, fluorine or hydrogen.

4) A cyclopentanone derivative of formula [1A] or a pharmacologically acceptable salt thereof, according to 3) described above, wherein:

$X_A$ is S;

$Y_A$ is a straight aliphatic hydrocarbon group having 1 to 6 carbon atoms, wherein:
at least two hydrogen atoms are substituted with any of carboxy, COOR1' (wherein R11 is an alkyl, alkenyl or alkynyl having 1 to 4 carbon atoms), COW2 (wherein W2 is a saturated heterocyclic ring unsubstituted or substituted with COOR11 (wherein R11 is an alkyl having 1 to 4 carbon atoms) or NHCOR12 (wherein R12 is an alkyl having 1 to 4 carbon atoms);

each of $Z1_A$, $Z2_A$ and $Z3_A$, which may be the same or different and independently represents carboxy, COOR4' (wherein R4' is an alkyl having 1 to 4 carbon atoms), hydroxy, OCOR13 (wherein R13 is an alkyl having 1 to 4 carbon atoms), $CH_2OR10'$ (wherein R10' is hydrogen, an alkyl having 1 to 4 carbon atoms or an acyl having 1 to 5 carbon atoms), or hydrogen; or, $Z2_A$ and $Z3_A$ are combined together to form a benzene ring unsubstituted or substituted with an alkyl having 1 to 4 carbon atoms, an alkyloxy having 1 to 4 carbon atoms, nitro, trifluoromethyl or halogen; and, $Z1_A$ is carboxy, COOR4' (wherein R4' is an alkyl having 1 to 4 carbon atoms), hydroxy, OCOR13 (wherein R13 is an alkyl having 1 to 4 carbon atoms), $CH_2OR10'$ (wherein R10' is hydrogen, an alkyl having 1 to 4 carbon atoms or an acyl having 1 to 5 carbon atoms), or hydrogen.

5) A cyclopentanone derivative of formula [1A] or a pharmacologically acceptable salt thereof, according to 4) described above, wherein:

$X_A$ is S;

$Y_A$ is a straight aliphatic hydrocarbon group having 1 to 6 carbon atoms, wherein:
one hydrogen is substituted with carboxy, methoxycarbonyl, COW3 (wherein W3 is a pyrrolidine, piperidine, azetidine, morpholine or piperazine ring, which may be unsubstituted or substituted with methoxycarbonyl) and one other hydrogen is substituted with acetylamino;

each of $Z1_A$, $Z2_A$ and $Z3_A$, which may be the same or different and independently represents carboxy, methoxycarbonyl, hydroxy, acetyloxymethyl, hydroxymethyl or hydrogen; or, $Z2_A$ and $Z3_A$ are combined together to form unsubstituted benzene ring; and, $Z1_A$ is carboxy, methoxycarbonyl, hydroxy, acetyloxymethyl, hydroxymethyl or hydrogen.

6) A cyclopentanone derivative of formula [1A] or a pharmacologically acceptable salt thereof, according to 5) described above, wherein the cyclopentanone derivative is selected from the group consisting of:

(I) $X_A$ is S, $Y_A$ is 2-acetylamino-2-carboxyethyl, Z1A and $Z3_A$ are hydrogen and, $Z2_A$ is carboxy;

(II) $X_A$ is S, $Y_A$ is 2-acetylamino-2-methoxycarbonylethyl, $Z1_A$ and $Z3_A$ are hydrogen and, $Z2_A$ is carboxy;

(III) $X_A$ is S, $Y_A$ is 2-acetylamino-2-carboxyethyl, $Z1_A$ and $Z3_A$ are hydrogen and, $Z2_A$ is hydroxy;

(IV) $X_A$ is S, $Y_A$ is 2-acetylamino-3-oxo-3-{1-(2-methoxycarbonyl)pyrrolidinyl}propyl, $Z1_A$ and $Z3_A$ are hydrogen and, $Z2_A$ is hydroxy;

(V) $X_A$ is S, $Y_A$ is 2-acetylamino-2-methoxycarbonylethyl, $Z2_A$ and $Z3_A$ are combined together to form an unsubstituted benzene ring and, $Z1_A$ is carboxy; and, (VI) $X_A$ is S, $Y_A$ is 2-acetylamino-2-carboxyethyl, $Z2_A$ and $Z3_A$ are combined together to form an unsubstituted benzene ring and, $Z1_A$ is carboxy.

7) A 2,3-di-substituted cyclopentanone derivative of formula [1B] or a pharmacologically acceptable salt thereof, according to 1) above, wherein:

$X_B$ is S, O or SO;

$Y_B$ is a straight or branched aliphatic hydrocarbon group having 7 to 20 carbon atoms (wherein at least one hydrogen may optionally be substituted with carboxy or a group derived therefrom or, amino or a group derived therefrom); and, $Z_B$ is carboxy, COOR3 (wherein R3 is an unsubstituted or substituted alkyl having 1 to 4 carbon atoms), $CH_2OR4$ (wherein R4 is hydrogen or an unsubstituted or substituted alkyl having 1 to 4 carbon atoms) or, $CH_2OCOR5$ (wherein R5 is an unsubstituted or substituted alkyl having 1 to 4 carbon atoms).

8) A 2,3-di-substituted cyclopentanone derivative of formula [1B] or a pharmacologically acceptable salt thereof, according to 7) described above, wherein:

$X_B$ is S;

$Y_B$ is a straight aliphatic hydrocarbon group having 7 to 20 carbon atoms (wherein at least two hydrogen atoms are substituted with carboxy, COOR6 (wherein R6 is an alkyl, alkenyl or alkynyl having 1 to 4 carbon atoms) or NR7R8 (wherein each of R7 and R8, which may be the same or different and independently represents hydrogen, an alkyl having 1 to 4 carbon atoms or an acyl having 1 to 5 carbon atoms); and, $Z_B$ is carboxy, methoxycarbonyl, hydroxymethyl or acetyloxymethyl.

9) A 2,3-di-substituted cyclopentanone derivative of formula [1B] or a pharmacologically acceptable salt thereof, according to 8) described above, wherein:

$X_B$ is S;

$Y_B$ is 11-acetylamino-11-carboxy-n-undecyl; and, $Z_B$ is carboxy.

10) A 2,3-di-substituted cyclopentanone derivative of formula [1B] or a pharmacologically acceptable salt thereof, according to 1) above, wherein:

$X_B$ is S, O or SO;

$Y_B$ is a straight or branched aliphatic hydrocarbon group having 1 to 6 carbon atoms wherein at least one hydrogen is substituted with COW2 {wherein W2 is a saturated heterocyclic ring unsubstituted or substituted with carboxy, a hydroxyalkyl having 1 to 4 carbon atoms, phenyl or COOR9 (wherein R9 is an unsubstituted or substituted alkyl having 1 to 4 carbon atoms)} and, at least one other hydrogen is substituted with NR10R11 (wherein each of R10 and R11, which may be the same or different and independently represents hydrogen, an unsubstituted or substituted alkyl having 1 to 4 carbon atoms or, an unsubstituted or substituted acyl having 1 to 5 carbon atoms); and, $Z_B$ is carboxy, COOR3 (wherein R3 is an unsubstituted or substituted alkyl having 1 to 4 carbon atoms), $CH_2OR4$ (wherein R4 is hydrogen or an unsubstituted or substituted alkyl having 1 to 4 carbon atoms) or, $CH_2OCOR5$ (wherein R5 is an unsubstituted or substituted alkyl having 1 to 4 carbon atoms).

11) A 2,3-di-substituted cyclopentanone derivative of formula [1B] or a pharmacologically acceptable salt thereof, according to 10) described above, wherein:

$X_B$ is S;

$Y_B$ is a straight or branched aliphatic hydrocarbon group having 1 to 6 carbon atoms {wherein one hydrogen is substituted with COW3 (wherein W3 is a 1-azetidinyl, 1-piperidyl, 1-pyrrolidinyl, 1-piperazinyl or 4-morpholinyl group, which group may be unsubstituted or substituted with carboxy, methoxycarbonyl, 2-hydroxyethyl, phenyl or tert-butoxycarbonyl) and one other hydrogen is substituted with NHCOR12 (wherein R12 is an alkyl having 1 to 4 carbon atoms)}; and, $Z_B$ is carboxy, methoxycarbonyl, hydroxymethyl or acetyloxy.

12) A 2,3-di-substituted cyclopentanone derivative of formula [1B] described in 1) above or a pharmacologically acceptable salt thereof, according to 11) described above, wherein:

$X_B$ is S;

$Y_B$ is 2-acetylamino-3-oxo-3-(1-pyrrolidinyl)propyl, 2-acetylamino-3-{1-(2-methoxycarbonyl)pyrrolidinyl-3-oxopropyl, 2-acetylamino-3-oxo-3-(1-piperidyl)propyl, 2-acetylamino-3-(4-morpholinyl)-3-oxopropyl, 2-acetylamino-3-{1-(2-methoxycarbonyl)azetidinyl}-3-oxopropyl, 2-acetylamino-3-oxo-3-(1-piperazinyl)propyl, 2-acetylamino-3-[1-{4-(2-hydroxyethyl)piperazinyl}]-3-oxopropyl, 2-acetylamino-3-{1-(4-phenylpiperazinyl)}-3-oxopropyl or 2-acetylamino-3-{1-(4-tert-butoxycarbonylpiperazinyl)}-3-oxopropyl; and, $Z_B$ is carboxy or methoxycarbonyl.

13) A 2,3-di-substituted cyclopentanone derivative of formula [1B] described in 1) above or a pharmacologically acceptable salt thereof, according to 1) above, wherein:

$X_B$ is S, O or SO;

$Y_B$ is a straight or branched aliphatic hydrocarbon group having 1 to 6 carbon atoms {wherein at least one hydrogen is substituted with NHCOV1 (wherein V1 is an alkyl having 2 to 5 carbon atoms and containing 4 to 11 halogen atoms) and, at least one other hydrogen may be further substituted with carboxy or COOR13 (wherein R13 is an unsubstituted or substituted alkyl, alkenyl or alkynyl having 1 to 4 carbon atoms)}; and, $Z_B$ is carboxy, COOR3 (wherein R3 is an unsubstituted or substituted alkyl having 1 to 4 carbon atoms), $CH_2OR4$ (wherein R4 is hydrogen or an unsubstituted or substituted alkyl having 1 to 4 carbon atoms) or $CH_2OCOR5$ (wherein R5 is an unsubstituted or substituted alkyl having 1 to 4 carbon atoms).

14) A 2,3-di-substituted cyclopentanone derivative of formula [1B] described in 1) above or a pharmacologically acceptable salt thereof, according to 13) described above, wherein:

$X_B$ is S;

$Y_B$ is a straight aliphatic hydrocarbon group having 1 to 6 carbon atoms {wherein one hydrogen is substituted with NHCOV2 (wherein V2 is an alkyl having 2 to 5 carbon atoms and containing 4 to 11 fluorine atoms) and, one other hydrogen is further substituted with carboxy or COOR13' (wherein R13' is an alkyl, alkenyl or alkynyl having 1 to 4 carbon atoms)}; and, $Z_B$ is carboxy, methoxycarbonyl, hydroxymethyl or acetyloxymethyl.

15) A 2,3-di-substituted cyclopentanone derivative of formula [1B] described in 1) above or a pharmacologically acceptable salt thereof, according to 14) described above, wherein:

$X_B$ is S;

$Y_B$ is 2-carboxy-2-(pentafluoropropionyl)aminoethyl; and, $Z_B$ is carboxy or hydroxymethyl.

16) A 2,3-di-substituted cyclopentanone derivative of formula [1B] described in 1) above or a pharmacologically acceptable salt thereof, according to 1) above, wherein:

$X_B$ is S, O or SO;

$Y_B$ is a straight or branched aliphatic hydrocarbon group having 1 to 6 carbon atoms {wherein at least one hydrogen is substituted with a substituted or unsubstituted monocyclic aromatic heterocyclic ring and at least one other hydrogen is further substituted with NR15R16 (wherein each of R15 and R16, which may be the same or different and independently represents hydrogen, an unsubstituted or substituted alkyl having 1 to 4 carbon atoms, or an unsubstituted or substituted acyl having 1 to 5 carbon atoms)}; and, $Z_B$ is carboxy, COOR3 (wherein R3 is an unsubstituted or substituted alkyl having 1 to 4 carbon atoms), $CH_2OR4$ (wherein R4 is hydrogen or an unsubstituted or substituted alkyl having 1 to 4 carbon atoms) or $CH_2OCOR5$ (wherein R5 is an unsubstituted or substituted alkyl having 1 to 4 carbon atoms).

17) A 2,3-di-substituted cyclopentanone derivative of formula [1B] described in 1) above or a pharmacologically acceptable salt thereof, according to 16) described above, wherein:

$X_B$ is S;

$Y_B$ is a straight aliphatic hydrocarbon group having 1 to 4 carbon atoms {wherein one hydrogen should be substituted with a pyridine ring unsubstituted or substituted with an alkyl having 1 to 4 carbon atoms or with 5-tetrazolyl, and one other hydrogen may be further substituted with NHCOR17 (wherein R17 is an alkyl having 1 to 4 carbon atoms}; and, $Z_B$ is carboxy, methoxycarbonyl, hydroxymethyl or acetyloxymethyl.

18) A 2,3-di-substituted cyclopentanone derivative of formula [1B] described in 1) above or a pharmacologically acceptable salt thereof, according to 17) described above, wherein:

$X_B$ is S;

$Y_B$ is 3-(3-pyridyl)propyl, 3-{3-(1-methylpyridinium iodide)}propyl or 2-acetylamino-2-(5-tetrazolyl)ethyl;

$Z_B$ is carboxy or methoxycarbonyl.

19) A cyclopentenone derivative of formula [1C] described in 1) above or a pharmacologically acceptable salt thereof, according to 1) above, wherein:

ring A forms an oxo-conjugated double bond together with the carbon atom bound to CH2-Xc-Yc;

$X_c$ is S, O or SO;

$Y_c$ is an aliphatic hydrocarbon group having 1 to 6 carbon atoms (wherein at least one hydrogen is substituted with carboxy or a group derived therefrom, amino or a group derived therefrom or, hydroxy or a group derived therefrom); and, each of $Z1_c$, $Z2_c$ and $Z3_c$, which may be the same or different and independently represents carboxy or a group derived therefrom, hydroxy or a group derived therefrom, amino or a group derived therefrom, a substituted or unsubstituted alkyl or alkenyl having 1 to 4 carbon atoms, a monocyclic aromatic heterocyclic ring, a halogen or hydrogen.

20) A cyclopentenone derivative of formula [iC] described in 1) above or a pharmacologically acceptable salt thereof, according to 19) described above, wherein:

ring A forms an oxo-conjugated double bond together with the carbon atom bound to $CH_2$—$X_c$—$Y_c$;

$X_c$ is S, O or SO;

$Y_c$ is an aliphatic hydrocarbon group having 1 to 6 carbon atoms (wherein at least one hydrogen is substituted with carboxy, COOR1 (wherein R1 is a substituted or unsubstituted alkyl or alkenyl having 1 to 4 carbon atoms), CONR2R3 (wherein each of R2 and R3 which may be the same or different and independently represents hydrogen or an unsubstituted or substituted alkyl having 1 to 4 carbon atoms), COW (wherein W is a heterocyclic ring unsubstituted or substituted with carboxy or a group derived therefrom or, amino or a group derived therefrom), NR4R5 (wherein each of R4 and R5, which may be the same or different and independently represents hydrogen, an unsubstituted or substituted alkyl having 1 to 4 carbon atoms or, an unsubstituted or substituted acyl having 1 to 5 carbon atoms) or OR6 (wherein R6 is hydrogen, an unsubstituted or substituted alkyl having 1 to 4 carbon atoms or, an unsubstituted or substituted acyl having 1 to 5 carbon atoms); and, each of $Z1_c$, $Z2_c$ and $Z3_c$ independently represents carboxy, COOR7 (wherein R7 is an unsubstituted or substituted alkyl having 1 to 4 carbon atoms), CONR8R9 (wherein each of R8 and R9, which may be the same or different and independently represents hydrogen or an unsubstituted or substituted alkyl having 1 to 4 carbon atoms), cyano, $CH_2OR10$ (wherein R10 is hydrogen, an unsubstituted or substituted alkyl having 1 to 4 carbon atoms or, an unsubstituted or substituted acyl having 1 to 5 carbon atoms), hydroxy, OCOR11 (wherein R11 is an unsubstituted or substituted alkyl having 1 to 4 carbon atoms), NR12R13 (wherein each of R12 and R13, which may be the same or different and independently represents hydrogen, an unsubstituted or substituted alkyl having 1 to 4 carbon atoms or, an unsubstituted or substituted acyl having 1 to 5 carbon atoms), 5-tetrazolyl, chlorine, fluorine or hydrogen.

21) A cyclopentenone derivative of formula [1C] described in 1) above or a pharmacologically acceptable salt thereof, according to 20) described above, wherein:

ring A forms an oxo-conjugated double bond together with the carbon atom bound to $CH_2$—$X_c$—$Y_c$;

$X_c$ is S;

$Y_c$ is an aliphatic hydrocarbon group having 1 to 6 carbon atoms (wherein at least two hydrogen atoms are substituted with carboxy, COOR1' (wherein R1' is an alkyl or alkenyl having 1 to 4 carbon atoms), NHCOR14 (wherein R14 is an alkyl having 1 to 4 carbon atoms which hydrogen may optionally be substituted with fluorine), hydroxy, or OCOR15 (wherein R15 is an alkyl having 1 to 4 carbon atoms); and, each of $Z1_c$, $Z2_c$ and $Z3_c$ is carboxy, COOR7' (wherein R7' is an alkyl having 1 to 4 carbon atoms) or $CH_2OR10'$ (wherein R10' is hydrogen or an acyl having 1 to 5 carbon atoms).

22) A cyclopentenone derivative of formula [1C] described in 1) above or a pharmacologically acceptable salt thereof, according to 21) described above, wherein:

ring A forms an oxo-conjugated double bond together with the carbon atom bound to $CH_2$—$X_c$—$Y_c$;

$X_c$ is S;

$Y_c$ is 2-acetylamino-2-carboxyethyl; and, either $Z1_c$ or $Z2_c$ is hydroxy and the remaining groups out of $Z1_c$, $Z2_c$ and $Z3_3$ are all hydrogen.

23) A cyclopentenone derivative of formula [1C] described in 1) above or a pharmacologically acceptable salt thereof, according to 1) above, wherein:

ring A forms an oxo-conjugated double bond without containing the carbon atom bound to $CH_2$—$X_c$—$Y_c$;

$X_c$ is S, O or SO;

$Y_c$ is an aliphatic hydrocarbon group having 1 to 6 carbon atoms (wherein at least one hydrogen is substituted with carboxy or a group derived therefrom, amino or a group derived therefrom or, hydroxy or a group derived therefrom); and, each of $Z1_c$, $Z2_c$ and $Z3_c$ is carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring, a halogen or hydrogen.

24) A cyclopentenone derivative of formula [1C] described in 1) above or a pharmacologically acceptable salt thereof, according to 23) described above, wherein:

ring A forms an oxo-conjugated double bond without containing the carbon atom bound to $CH_2$—$X_c$—$Y_c$;

$X_c$ is S, O or SO;

$Y_c$ is an aliphatic hydrocarbon group having 1 to 6 carbon atoms (wherein at least one hydrogen is substituted with carboxy, COOR1 (wherein R1 is a substituted or unsubstituted alkyl or alkenyl having 1 to 4 carbon atoms), CONR2R3 (wherein each of R2 and R3 which may be the same or different and independently represents hydrogen or an unsubstituted or substituted alkyl having 1 to 4 carbon atoms), COW (wherein W is a heterocyclic ring unsubstituted or substituted with carboxy or a group derived therefrom or, amino or a group derived therefrom), NR4R5 (wherein each of R4 and R5, which may be the same or different and independently represents hydrogen, an unsubstituted or substituted alkyl having 1 to 4 carbon atoms or, an unsubstituted or substituted acyl having 1 to 5 carbon atoms) or OR6 (wherein R6 is hydrogen, an unsubstituted or substituted alkyl having 1 to 4 carbon atoms or, an unsubstituted or substituted acyl having 1 to 5 carbon atoms); and, each of $Z1_c$, $Z2_c$ and $Z3_c$ independently represents carboxy, COOR7 (wherein R7 is an unsubstituted or substituted alkyl having 1 to 4 carbon atoms), CONR8R9 (wherein each of R8 and R9, which may be the same or different and independently represents hydrogen or an unsubstituted or substituted alkyl having 1 to 4 carbon atoms), cyano, $CH_2OR10$ (wherein R10 is hydrogen, an unsubstituted or substituted alkyl having 1 to 4 carbon atoms or, an unsubstituted or substituted acyl having 1 to 5 carbon atoms), hydroxy, OCOR11 (wherein R11 is an unsubstituted or substituted alkyl having 1 to 4 carbon atoms), NR12R13 (wherein each of R12 and R13, which may be the same or different and independently represents hydrogen, an unsubstituted or substituted alkyl having 1 to 4 carbon atoms or, an unsubstituted or substituted acyl having 1 to 5 carbon atoms), 5-tetrazolyl, chlorine, fluorine or hydrogen.

25) A cyclopentenone derivative of formula [1C] described in 1) above or a pharmacologically acceptable salt thereof, according to 24) described above, wherein:

ring A forms an oxo-conjugated double bond without containing the carbon atom bound to $CH_2-X_c-Y_c$;

$X_c$ is S;

$Y_c$ is an aliphatic hydrocarbon group having 1 to 6 carbon atoms (wherein at least two hydrogen atoms are substituted with carboxy, COOR1' (wherein R1' is an alkyl or alkenyl having 1 to 4 carbon atoms), NHCOR14 (wherein R14 is an alkyl having 1 to 4 carbon atoms which hydrogen may optionally be substituted with fluorine), hydroxy or OCOR15 (wherein R15 is an alkyl having 1 to 4 carbon atoms); and, each of $Z1_c$, $Z2_c$ and $Z3_3$ is carboxy, COOR7' (wherein R7' is an alkyl having 1 to 4 carbon atoms) or $CH_2OR10'$ (wherein R10' is hydrogen or an acyl having 1 to 5 carbon atoms).

26) A cyclopentenone derivative of formula [1C] described in 1) above or a pharmacologically acceptable salt thereof, according to 25) described above, wherein:

ring A forms an oxo-conjugated double bond without containing the carbon atom bound to $CH_2-X_c-Y_c$;

$X_c$ is S;

$Y_c$ is 2-acetylamino-2-carboxyethyl; and, all of $Z1_c$, $Z2_c$ and $Z3_c$ are hydrogen.

27) A ketone derivative of formula [1D] described in 1) above or a pharmacologically acceptable salt thereof, according to 1) above, wherein:

$A_D$ is an unsubstituted or substituted aliphatic hydrocarbon group having 1 to 4 carbon atoms;

$B_D$ is hydrogen or an unsubstituted or substituted aliphatic hydrocarbon group having 1 to 4 carbon atoms;

$X_D$ is S, O, or SO;

$Y_D$ is an aliphatic hydrocarbon group having 1 to 6 carbon atoms (wherein at least one hydrogen is substituted with carboxy or a group derived therefrom, amino or a group derived therefrom or, hydroxy or a group derived therefrom); and, $Z_D$ is carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring, a halogen or hydrogen.

28) A ketone derivative of formula [1D] described in 1) above or a pharmacologically acceptable salt thereof, according to 27) described above, wherein:

$A_D$ is an aliphatic hydrocarbon group having 1 to 4 carbon atoms;

$B_D$ is hydrogen or an aliphatic hydrocarbon group having 1 to 4 carbon atoms;

$X_D$ is S, O, or SO;

$Y_D$ is an aliphatic hydrocarbon group having 1 to 6 carbon atoms (wherein at least one hydrogen is substituted with carboxy, COOR1 (wherein R1 is a substituted or unsubstituted alkyl or alkenyl having 1 to 4 carbon atoms), CONR2R3 (wherein each of R2 and R3 which may be the same or different and independently represents hydrogen or an unsubstituted or substituted alkyl having 1 to 4 carbon atoms), COW (wherein W is a heterocyclic ring unsubstituted or substituted with carboxy or a group derived therefrom or, amino or a group derived therefrom), NR4R5 (wherein each of R4 and R5, which may be the same or different and independently represents hydrogen, an unsubstituted or substituted alkyl having 1 to 4 carbon atoms or, an unsubstituted or substituted acyl having 1 to 5 carbon atoms) or OR6 (wherein R6 is hydrogen, an unsubstituted or substituted alkyl having 1 to 4 carbon atoms or, an unsubstituted or substituted acyl having 1 to 5 carbon atoms); and, $Z_D$ is carboxy, COOR7 (wherein R7 is an unsubstituted or substituted alkyl having 1 to 4 carbon atoms), CONR8R9 (wherein each of R8 and R9, which may be the same or different and independently represents hydrogen or an unsubstituted or substituted alkyl having 1 to 4 carbon atoms), cyano, $CH_2OR10$ (wherein R10 is hydrogen, an unsubstituted or substituted alkyl having 1 to 4 carbon atoms or, an unsubstituted or substituted acyl having 1 to 5 carbon atoms), hydroxy, OCOR11 (wherein R11 is an unsubstituted or substituted alkyl having 1 to 4 carbon atoms), NR12R13 (wherein each of R12 and R13 which may be the same or different and independently represents hydrogen, an unsubstituted or substituted alkyl having 1 to 4 carbon atoms or, an unsubstituted or substituted acyl having 1 to 5 carbon atoms), 5-tetrazolyl, chlorine, fluorine or hydrogen.

29) A ketone derivative of formula [1D] described in 1) above or a pharmacologically acceptable salt thereof, according to 28) described above, wherein:

$A_D$ is an alkyl having 1 to 4 carbon atoms;

$B_D$ is hydrogen or an alkyl having 1 to 4 carbon atoms;

$X_D$ is S;

$Y_D$ is an aliphatic hydrocarbon group having 1 to 6 carbon atoms (wherein at least two hydrogen atoms are substituted with carboxy, COOR1' (wherein R1 is an alkyl or alkenyl having 1 to 4 carbon atoms), NHCOR14 (wherein R14 is an alkyl having 1 to 4 carbon atoms which hydrogen may optionally be substituted with fluorine), hydroxy or OCOR15 (wherein R15 is an alkyl having 1 to 4 carbon atoms);

$Z_D$ is carboxy, COOR7' (wherein R7' is an alkyl having 1 to 4 carbon atoms) or $CH_2OR10'$ (wherein R10' is hydrogen or an acyl having 1 to 5 carbon atoms).

30) A ketone derivative of formula [1D] described in 1) above or a pharmacologically acceptable salt thereof, according to 29) described above, wherein:

$A_D$ is methyl;

$B_D$ is hydrogen;

$X_D$ is S;

$Y_D$ is 2-acetylamino-2-carboxyethyl or 2-acetylamino-2-methoxycarbonylethyl; and, $Z_D$ is carboxy, methoxycarbonyl, acetoxymethyl or hydroxymethyl.

31) A ketone derivative of formula [1D] described in 1) above or a pharmacologically acceptable salt thereof, according to 1) above, wherein:

15

$A_D$ is an unsubstituted or substituted aromatic hydrocarbon, aromatic heterocyclic ring or saturated heterocyclic ring;

$B_D$ is hydrogen or an unsubstituted or substituted aliphatic hydrocarbon group having 1 to 4 carbon atoms;

$X_D$ is S, O, or SO;

$Y_D$ is an aliphatic hydrocarbon group having 1 to 6 carbon atoms (wherein at least one hydrogen is substituted with carboxy or a group derived therefrom, amino or a group derived therefrom or, hydroxy or a group derived therefrom); and, $Z_D$ is carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring, a halogen or hydrogen.

32) A ketone derivative of formula [1D] described in 1) above or a pharmacologically acceptable salt thereof, according to 31) described above, wherein:

$A_D$ is an unsubstituted benzene ring wherein, when substituted, 1 to 3 hydrogen atoms are substituted with an unsubstituted or substituted alkyl group having 1 to 4 carbon atoms, a halogen, hydroxy, an alkoxy having 1 to 4 carbon atoms, amino, an alkyl- or dialkylamino having 1 to 4 carbon atoms, thiol, carboxy, an alkoxycarbonyl having 1 to 4 carbon atoms, an acyloxy having 1 to 5 carbon atoms, an acylthio having 1 to 5 carbon atoms, an acylamino having 1 to 5 carbon atoms, cyano or trifluoromethyl;

$B_D$ is hydrogen or an aliphatic hydrocarbon group having 1 to 4 carbon atoms;

$X_D$ is S, O, or SO;

$Y_D$ is an aliphatic hydrocarbon group having 1 to 6 carbon atoms (wherein at least one hydrogen is substituted with carboxy, COOR1 (wherein R1 is a substituted or unsubstituted alkyl or alkenyl having 1 to 4 carbon atoms), CONR2R3 (wherein each of R2 and R3 which may be the same or different and independently represents hydrogen or an unsubstituted or substituted alkyl having 1 to 4 carbon atoms), COW (wherein W is a heterocyclic ring which may be unsubstituted or substituted with carboxy or a group derived therefrom or, amino or a group derived therefrom), NR4R5 (wherein each of R4 and R5, which may be the same or different and independently represents hydrogen, an unsubstituted or substituted alkyl having 1 to 4 carbon atoms or, an unsubstituted or substituted acyl having 1 to 5 carbon atoms) or OR6 (wherein R6 is hydrogen, an unsubstituted or substituted alkyl having 1 to 4 carbon atoms or, an unsubstituted or substituted acyl having 1 to 5 carbon atoms); and, $Z_D$ is carboxy, COOR7 (wherein R7 is an unsubstituted or substituted alkyl having 1 to 4 carbon atoms), CONR8R9 (wherein each of R8 and R9, which may be the same or different and independently represents hydrogen or an unsubstituted or substituted alkyl having 1 to 4 carbon atoms), cyano, CH$_2$OR10 (wherein R10 is hydrogen, an unsubstituted or substituted alkyl having 1 to 4 carbon atoms or, an unsubstituted or substituted acyl having 1 to 5 carbon atoms), hydroxy, OCOR11 (wherein R11 is an unsubstituted or substituted alkyl having 1 to 4 carbon atoms), NR12R13 (wherein each of R12 and R13 which may be the same or different and independently represents hydrogen, an unsubstituted or substituted alkyl having 1 to 4 carbon atoms or, an unsubstituted or substituted acyl having 1 to 5 carbon atoms), 5-tetrazolyl, chlorine, fluorine or hydrogen.

16

33) A ketone derivative of formula [1D] described in 1) above or a pharmacologically acceptable salt thereof, according to 32) described above, wherein:

$A_D$ is an unsubstituted or substituted benzene ring, wherein, when substituted, 1 to 3 hydrogen atoms are substituted with methyl, methoxy, methoxycarbonyl, nitro, cyano, a halogen or trifluoromethyl;

$B_D$ is hydrogen or an alkyl having 1 to 4 carbon atoms;

$X_D$ is S;

$Y_D$ is an aliphatic hydrocarbon group having 1 to 6 carbon atoms (wherein at least two hydrogen atoms are substituted with carboxy, COOR1' (wherein R1' is an alkyl or alkenyl having 1 to 4 carbon atoms), NHCOR14 (wherein R14 is an alkyl having 1 to 4 carbon atoms which hydrogen may optionally be substituted with fluorine), hydroxy or OCOR15 (wherein R15 is an alkyl having 1 to 4 carbon atoms);

$Z_D$ is carboxy, COOR7' (wherein R7' is an alkyl having 1 to 4 carbon atoms) or CH$_2$OR10' (wherein R10' is hydrogen or an acyl having 1 to 5 carbon atoms).

34) A ketone derivative of formula [1D] described in 1) above or a pharmacologically acceptable salt thereof, according to 33) described above, wherein:

$A_D$ is an unsubstituted benzene ring or a benzene ring substituted with methyl or methoxy;

$B_D$ is hydrogen;

$X_D$ is S;

$Y_D$ is 2-acetylamino-2-carboxyethyl, 2-acetylamino-2-methoxycarbonylethyl or 2-acetylaminoethyl; and, $Z_D$ is carboxy, methoxycarbonyl, acetoxymethyl or hydroxymethyl.

35) A ketone derivative of formula [1D] described in 1) above or a pharmacologically acceptable salt thereof, according to 1) above, wherein:

$A_D$ and $B_D$ are combined together to form an unsubstituted or substituted cycloalkan-1-one ring having 3 to 7 carbon atoms (except for 5 carbon atoms);

$X_D$ is S, O, or SO;

$Y_D$ is an aliphatic hydrocarbon group having 1 to 6 carbon atoms (wherein at least one hydrogen is substituted with carboxy or a group derived therefrom, amino or a group derived therefrom or, hydroxy or a group derived therefrom); and, $Z_D$ is carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring, a halogen or hydrogen.

36) A ketone derivative of formula [1D] described in 1) above or a pharmacologically acceptable salt thereof, according to 35) described above, wherein:

$A_D$ and $B_D$ are combined together to form an unsubstituted or substituted cyclobutan-1-one ring or cyclohexan-1-one ring;

$X_D$ is S, O, or SO;

$Y_D$ is an aliphatic hydrocarbon group having 1 to 6 carbon atoms (wherein at least one hydrogen is substituted with carboxy, COOR1 (wherein R1 is a substituted or unsubstituted alkyl or alkenyl having 1 to 4 carbon atoms), CONR2R3 (wherein each of R2 and R3 which may be the same or different and independently represents hydrogen or an unsubstituted or substituted alkyl having 1 to 4 carbon atoms), COW (wherein W is a heterocyclic ring which may be unsubstituted or substituted with carboxy or a group derived therefrom or, amino or a group derived therefrom), NR4R5 (wherein each of R4 and R5, which may be the same or different and independently represents hydrogen, an unsubstituted or substituted alkyl having 1 to 4 carbon atoms or, an unsubstituted or substituted acyl having 1 to 5 carbon atoms) or OR6 (wherein R6 is hydrogen, an unsubstituted or substituted alkyl having 1 to 4 carbon atoms or, an unsubstituted or substituted acyl having 1 to 5 carbon atoms); and, $Z_D$ is carboxy, COOR7 (wherein R7 is an unsubstituted or substituted alkyl having 1 to 4 carbon atoms), CONR8R9 (wherein each of R8 and R9, which may be the same or different and independently represents hydrogen or an unsubstituted or substituted alkyl having 1 to 4 carbon atoms), cyano, $CH_2OR10$ (wherein R10 is hydrogen, an unsubstituted or substituted alkyl having 1 to 4 carbon atoms or, an unsubstituted or substituted acyl having 1 to 5 carbon atoms), hydroxy, OCOR11 (wherein R11 is an unsubstituted or substituted alkyl having 1 to 4 carbon atoms), NR12R13 (wherein each of R12 and R13, which may be the same or different and independently represents hydrogen, an unsubstituted or substituted alkyl having 1 to 4 carbon atoms or, an unsubstituted or substituted acyl having 1 to 5 carbon atoms), 5-tetrazolyl, chlorine, fluorine or hydrogen.

37) A ketone derivative of formula [1D] described in 1) above or a pharmacologically acceptable salt thereof, according to 36) described above, wherein:

$A_D$ and $B_D$ are combined together to form a cyclobutan-1-one ring or cyclohexan-1-one ring;

$X_D$ is S;

$Y_D$ is an aliphatic hydrocarbon group having 1 to 6 carbon atoms (wherein at least two hydrogen atoms are substituted with carboxy, COOR1' (wherein R1' is an alkyl or alkenyl having 1 to 4 carbon atoms), NHCOR14 (wherein R14 is an alkyl having 1 to 4 carbon atoms which hydrogen may optionally be substituted with fluorine), hydroxy or OCOR15 (wherein R15 is an alkyl having 1 to 4 carbon atoms);

$Z_D$ is carboxy, COOR7' (wherein R7' is an alkyl having 1 to 4 carbon atoms) or $CH_2OR10'$ (wherein R10' is hydrogen or an acyl having 1 to 5 carbon atoms).

38) A ketone derivative of formula [1D] described in 1) above or a pharmacologically acceptable salt thereof, according to 37), wherein:

(I) $A_D$ and $B_D$ are combined together to form a cyclobutan-1-one ring, $X_D$ is S, $Y_D$ is 2-acetylamino-2-carboxyethyl and, $Z_D$ is carboxy;

(II) $A_D$ and $B_D$ are combined together to form a cyclobutan-1-one ring, $X_D$ is S, $Y_D$ is 2-acetylamino-2-methoxycarbonylethyl and, $Z_D$ is methoxycarbonyl;

(III) $A_D$ and $B_D$ are combined together to form a cyclobutan-1-one ring, $X_D$ is S, $Y_D$ is 2,3-dihydroxy-n-propyl and, $Z_D$ is acetoxymethyl; and, (IV) $A_D$ and $B_D$ are combined together to form a cyclohexan-1-one ring, $X_D$ is S, $Y_D$ is 2-acetylamino-2-carboxyethyl and, $Z_D$ is carboxy.

39) A β-di-substituted aminoketone derivative of formula [1F] described in 1) above or a pharmacologically acceptable salt thereof, according to 1) above, wherein:

$A_F$ is an unsubstituted or substituted aliphatic hydrocarbon group having 1 to 4 carbon atoms;

$B_F$ is hydrogen or, an unsubstituted or substituted aliphatic hydrocarbon group having 1 to 4 carbon atoms;

$X_F$ and $Y_F$ are a straight or branched aliphatic hydrocarbon group having 1 to 10 carbon atoms (wherein at least one hydrogen may optionally be substituted with carboxy or a group derived therefrom, amino or a group derived therefrom or, hydroxy or a group derived therefrom) or; $X_F$ and $Y_F$ are bound to each other directly or via a hetero atom to form a monocyclic heterocyclic ring (wherein at least one hydrogen may optionally be substituted with an alkyl having 1 to 4 carbon atoms, phenyl, carboxy or a group derived therefrom, amino or a group derived therefrom or, hydroxy or a group derived therefrom);

$Z_F$ is carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring or a halogen.

40) A β-di-substituted aminoketone derivative of formula [1F] described in 1) above or a pharmacologically acceptable salt thereof, according to 39) described above, wherein:

$A_F$ is methyl, ethyl, n-propyl or isopropyl, which may be unsubstituted or substituted;

$B_F$ is hydrogen;

each of $X_F$ and $Y_F$, which may be the same or different and independently represents an alkyl having 1 to 6 carbon atoms or, $X_F$ and $Y_F$ are bound to each other directly or via a hetero atom to form a monocyclic heteroaryl ring which may be unsubstituted or substituted with an alkyl having 1 to 4 carbon atoms or phenyl;

$Z_F$ is carboxy, COOR1 (wherein R1 is a substituted or unsubstituted alkyl having 1 to 4 carbon atoms or, phenyl), CONR2R3 (wherein each of R2 and R3, which may be the same or different and independently represents hydrogen or an unsubstituted or substituted alkyl having 1 to 4 carbon atoms), cyano, $CH_2OR4$ (wherein R4 is hydrogen, an unsubstituted or substituted alkyl having 1 to 4 carbon atoms or, an unsubstituted or substituted acyl having 1 to 5 carbon atoms), hydroxy, OR5 (wherein R5 is an unsubstituted or substituted alkyl having 1 to 4 carbon atoms or, an unsubstituted or substituted acyl having 1 to 5 carbon atoms), NR6R7 (wherein each of R6 and R7, which may be the same or different and independently represents hydrogen, an unsubstituted or substituted alkyl having 1 to 4 carbon atoms or, an unsubstituted or substituted acyl having 1 to 5 carbon atoms), 5-tetrazolyl, chlorine or fluorine. 41) A β-di-substituted aminoketone derivative of formula [1F] described in 1) above or a pharmacologically acceptable salt thereof, according to 40) described above, wherein:

$A_F$ is methyl;

$B_F$ is hydrogen;

$X_F$ and $Y_F$ are both ethyl n-propyl or isopropyl, $X_F$ and $Y_F$ are bound to each other directly or via a hetero atom to form a pyrrolidine, piperidine, morpholine, 4-methylpiperazine or 4-phenylpiperazine ring;

$Z_F$ is carboxy, COOR1' (wherein R1' is an alkyl having 1 to 4 carbon atoms), CONR2'R3' (wherein R2' and R3', which may be the same or different and each is hydrogen or an alkyl having 1 to 4 carbon atoms) or cyano.

42) A β-di-substituted aminoketone derivative of formula [1F] described in 1) above or a pharmacologically acceptable salt thereof, according to 1) above, wherein:

$A_F$ is an unsubstituted or substituted aryl, heteroaryl or saturated heterocyclic ring;

B$_F$ is hydrogen or, an unsubstituted or substituted aliphatic hydrocarbon group having 1 to 4 carbon atoms;

X$_F$ and Y$_F$ are a straight or branched aliphatic hydrocarbon group having 1 to 10 carbon atoms (wherein at least one hydrogen may optionally be substituted with carboxy or a group derived therefrom, amino or a group derived therefrom or, hydroxy or a group derived therefrom) or, X$_F$ and Y$_F$ are bound to each other directly or via a hetero atom to form a heterocyclic ring (wherein at least one hydrogen may optionally be substituted with an alkyl having 1 to 4 carbon atoms, phenyl, carboxy or a group derived therefrom, amino or a group derived therefrom or, hydroxy or a group derived therefrom);

Z$_F$ is carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring or a halogen.

43) A β-di-substituted aminoketone derivative of formula [1F] described in 1) above or a pharmacologically acceptable salt thereof, according to 42) described above, wherein:

A$_F$ is an unsubstituted or substituted benzene ring or, monocyclic aromatic heterocyclic ring;

B$_F$ is hydrogen;

X$_F$ and Y$_F$, which may be the same or different, are a straight or branched aliphatic hydrocarbon group having 1 to 6 or, X$_F$ and Y$_F$ are bound to each other directly or via a hetero atom to form a heterocyclic ring unsubstituted or substituted with an alkyl having 1 to 4 carbon atoms or phenyl;

Z$_F$ is carboxy, COOR1 (wherein R1 is a substituted or unsubstituted alkyl having 1 to 4 carbon atoms or, phenyl), CONR2R3 (wherein each of R2 and R3, which may be the same or different and independently represents hydrogen or an unsubstituted or substituted alkyl having 1 to 4 carbon atoms), cyano, CH$_2$OR4 (wherein R4 is hydrogen, an unsubstituted or substituted alkyl having 1 to 4 carbon atoms or, an unsubstituted or substituted acyl having 1 to 5 carbon atoms), hydroxy, OR5 (wherein R5 is an unsubstituted or substituted alkyl having 1 to 4 carbon atoms or, an unsubstituted or substituted acyl having 1 to 5 carbon atoms), NR6R7 (wherein each of R6 and R7, which may be the same or different and independently represents hydrogen, an unsubstituted or substituted alkyl having 1 to 4 carbon atoms or, an unsubstituted or substituted acyl having 1 to 5 carbon atoms), 5-tetrazolyl, chlorine or fluorine.

44) A β-di-substituted aminoketone derivative of formula [1F] described in 1) above or a pharmacologically acceptable salt thereof, according to 43) described above, wherein:

A$_F$ is an unsubstituted or substituted benzene ring wherein, when substituted, 1 to 3 hydrogen atoms are substituted with an alkyl having 1 to 4 carbon atoms, a halogen, hydroxy, an alkoxy having 1 to 4 carbon atoms, amino, an alkyl- or dialkylamino having 1 to 4 carbon atoms, thiol, carboxy, an alkoxycarbonyl having 1 to 4 carbon atoms, an acyloxy having 1 to 5 carbon atoms, an acylthio having 1 to 5 carbon atoms, an acylamino having 1 to 5 carbon atoms, cyano or trifluoromethyl;

B$_F$ is hydrogen;

each of X$_F$ and Y$_F$, which may be the same or different and independently represents an alkyl having 1 to 6 carbon atoms or, X$_F$ and Y$_F$ are bound to each other directly or via a hetero atom to form a monocyclic heterocyclic ring unsubstituted or substituted with an alkyl having 1 to 4 carbon atoms or phenyl;

Z$_F$ is carboxy, COOR1' (wherein R1' is an alkyl having 1 to 4 carbon atoms), CONR2'R3' (wherein R2' and R3', which may be the same or different and each is hydrogen or an alkyl having 1 to 4 carbon atoms), cyano, or CH$_2$OR4' (wherein R4' is hydrogen, an alkyl having 1 to 4 carbon atoms or an acyl having 1 to 5 carbon atoms).

45) A β-di-substituted aminoketone derivative of formula [1F] described in 1) above or a pharmacologically acceptable salt thereof, according to 44) described above, wherein:

A$_F$ is an unsubstituted or substituted benzene ring, wherein, when substituted, 1 to 3 hydrogen atoms are substituted with methyl, methoxy, methoxycarbonyl, nitro, cyano, a halogen or trifluoromethyl;

B$_F$ is hydrogen;

X$_F$ and Y$_F$ are both ethyl, n-propyl or isopropyl; or, X$_F$ and Y$_F$ are bound to each other directly or via a hetero atom to form a pyrrolidine, piperidine, morpholine, 4-methylpiperazine or 4-phenylpiperazine ring;

Z$_F$ is carboxy, COOR1" (wherein R1" is methyl or ethyl), CONR2"R3" (wherein R2" and R3", which may be the same or different and each is hydrogen, methyl or ethyl) or cyano.

46) A β-di-substituted aminoketone derivative of formula [1F] described in 1) above or a pharmacologically acceptable salt thereof, according to 1) above, wherein:

A$_F$ and B$_F$ are combined together to form an unsubstituted or substituted cycloalkan-1-one ring having 3 to 7 carbon atoms or, A$_F$ and B$_F$ are combined together to form a cycloalkan-1-one ring having 3 to 7 carbon atoms, which ring is fused with an aromatic hydrocarbon or a aromatic heterocyclic ring.

X$_F$ and Y$_F$ are a straight or branched aliphatic hydrocarbon group having 1 to 10 carbon atoms (wherein at least one hydrogen may optionally be substituted with carboxy or a group derived therefrom, amino or a group derived therefrom or, hydroxy or a group derived therefrom) or, X$_F$ and Y$_F$ are bound to each other directly or via a hetero atom to form a heterocyclic ring (wherein at least one hydrogen may optionally be substituted with an alkyl having 1 to 4 carbon atoms, phenyl, carboxy or a group derived therefrom, amino or a group derived therefrom or, hydroxy or a group derived therefrom);

Z$_F$ is carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring or a halogen.

47) A β-di-substituted aminoketone derivative of formula [1F] described in 1) above or a pharmacologically acceptable salt thereof, according to 46) described above, wherein:

A$_F$ and B$_F$ are combined together to form an unsubstituted or substituted cycloalkan-1-one ring having 4 to 6 carbon atoms or, to form an unsubstituted or substituted cycloalkan-1-one ring having 4 to 6 carbon atoms which is fused with an aromatic hydrocarbon or monocyclic aromatic heterocyclic ring;

each of X$_F$ and Y$_F$, which may be the same or different and independently is a straight or branched aliphatic hydrocarbon group having 1 to 6 carbon atoms or, X$_F$ and Y$_F$ are bound to each other directly or via a hetero atom to form a monocyclic heterocyclic ring, which may be unsubstituted or substituted with an alkyl having 1 to 4 carbon atoms or phenyl;

$Z_F$ is carboxy, COOR1 (wherein R1 is a substituted or unsubstituted alkyl having 1 to 4 carbon atoms or, phenyl), CONR2R3 (wherein each of R2 and R3, which may be the same or different and independently represents hydrogen or an unsubstituted or substituted alkyl having 1 to 4 carbon atoms), cyano, $CH_2OR4$ (wherein R4 is hydrogen, an unsubstituted or substituted alkyl having 1 to 4 carbon atoms or, an unsubstituted or substituted acyl having 1 to 5 carbon atoms), hydroxy, OR5 (wherein R5 is an unsubstituted or substituted alkyl having 1 to 4 carbon atoms or, an unsubstituted or substituted acyl having 1 to 5 carbon atoms, preferably an alkyl having 1 to 4 carbon atoms or an acyl having 1 to 5 carbon atoms), NR6R7 (wherein each of R6 and R7, which may be the same or different and independently is hydrogen, an alkyl having 1 to 4 carbon atoms or an acyl having 1 to 5 carbon atoms), 5-tetrazolyl, chlorine or fluorine.

48) A β-di-substituted aminoketone derivative of formula [1F] described in 1) above or a pharmacologically acceptable salt thereof, according to 47) described above, wherein:

$A_F$ and $B_F$ are combined together to form an unsubstituted or substituted cyclopentan-1-one ring or to form an unsubstituted or substituted cyclopentan-1-one ring fused with a benzene or monocyclic aromatic heterocyclic ring;

each of $X_F$ and $Y_F$, which may be the same or different and independently is an alkyl 1 to 6 carbon atoms or, $X_F$ and $Y_F$ are bound to each other directly or via a hetero atom to form a monocyclic heteroaryl ring, which may be unsubstituted or substituted with an alkyl having 1 to 4 carbon atoms or phenyl;

$Z_F$ is carboxy, COOR1' (wherein R1' is an alkyl having 1 to 4 carbon atoms), CONR2'R3' (wherein R2' and R3', which may be the same or different and each is hydrogen or an alkyl having 1 to 4 carbon atoms), cyano or $CH_2OR4'$ (wherein R4' is hydrogen, an alkyl having 1 to 4 carbon atoms or an acyl having 1 to 5 carbon atoms).

49) A β-di-substituted aminoketone derivative of formula [1F] described in 1) above or a pharmacologically acceptable salt thereof, according to 48) described above, wherein:

$A_F$ and $B_F$ are combined together to form a cyclopentan-1-one ring or indan-1-one ring;

$X_F$ and $Y_F$ are both ethyl, n-propyl or isopropyl; or, $X_F$ and $Y_F$ are bound to each other directly or via a hetero atom to form a pyrrolidine, piperidine, morpholine, 4-methylpiperazine or 4-phenylpiperazine ring; and, $Z_F$ is carboxy, COOR1" (wherein R1" is methyl or ethyl), CONR2"R3" (wherein R2" and R3", which may be the same or different and each is hydrogen, methyl or ethyl) or cyano.

50) A pharmaceutical composition comprising as an effective ingredient a cyclopentanone derivative of formula [1A] according to 1) above or a cyclopentanone derivative according to any one of 2) through 6) described above, or a pharmacologically acceptable salt thereof, wherein the cyclopentanone derivative further includes:

(1) when $Z1_A$ and $Z2_A$ are hydrogen, $X_A$ is S, $Y_A$ is methyl or benzyl and, $Z3_A$ is methoxycarbonyl, (2) when $Z1_A$ and $Z2_A$ are hydrogen, $X_A$ is O or N, $Y_A$ is benzyl and, $Z3_A$ is carboxy, methoxycarbonyl or ethoxycarbonyl;

(3) $X_A$ is N or O, $Z1_A$ and $Z3_A$ are hydrogen and, $Z2_A$ is carboxy or methoxycarbonyl;

(4) $X_A$ is O, $Z1_A$ is hydroxy or a group derived therefrom, $Z2_A$ is hydrogen and, $Z3_A$ is amino or a group derived therefrom;

(5) $X_A$ is S, $Y1_A$ is phenyl, $Z1_A$ is dimethoxymethyl and, $Z2_A$ and $Z3_A$ are hydrogen;

(6) $X_A$ is O, $Y1_A$ is methyl, $Z1_A$ is 1-methoxy-1-phenylthiomethyl and, $Z2_A$ and $Z3_A$ are hydrogen;

(7) $Z1_A$ is S, SO or $SO_2$, $Z2_A$ is hydroxy or a group derived therefrom and, $Z3_A$ is hydrogen.

51) A composition for the treatment of central nervous disorders comprising as an effective ingredient a cyclopentanone derivative of formula [1A] according to 1) above or a cyclopentanone derivative according to any one of 2) through 6) described above, or a pharmacologically acceptable salt thereof, wherein the cyclopentanone derivative further includes:

(1) when $Z1_A$ and $Z2_A$ are hydrogen, $X_A$ is S, $Y_A$ is methyl or benzyl and, $Z3_A$ is methoxycarbonyl, (2) when $Z1_A$ and $Z2_A$ are hydrogen, $X_A$ is O or N, $Y_A$ is benzyl and, $Z3_A$ is carboxy, methoxycarbonyl or ethoxycarbonyl;

(3) $X_A$ is N or O, $Z1_A$ and $Z3_A$ are hydrogen and, $Z2_A$ is carboxy or methoxycarbonyl;

(4) $X_A$ is O, $Z1_A$ is hydroxy or a group derived therefrom, $Z2_A$ is hydrogen and, $Z3_A$ is amino or a group derived therefrom;

(5) $X_A$ is S, $Y1_A$ is phenyl, $Z1_A$ is dimethoxymethyl and, $Z2_A$ and $Z3_A$ are hydrogen;

(6) $X_A$ is O, $Y1_A$ is methyl, $Z1_A$ is 1-methoxy-1-phenylthiomethyl and, $Z2_A$ and $Z3_A$ are hydrogen;

(7) $Z1_A$ is S, SO or $SO_2$, $Z2_A$ is hydroxy or a group derived therefrom and, $Z3_A$ is hydrogen.

52) A composition for the treatment of peripheral nervous disorders comprising as an effective ingredient a cyclopentanone derivative of formula [1A] according to 1) above or a cyclopentanone derivative according to any one of 2) through 6) described above, or a pharmacologically acceptable salt thereof, wherein the cyclopentanone derivative further includes:

(1) when $Z1_A$ and $Z2_A$ are hydrogen, $X_A$ is S, $Y_A$ is methyl or benzyl and, $Z3_A$ is methoxycarbonyl, (2) when $Z1_A$ and $Z2_A$ are hydrogen, $X_A$ is O or N, $Y_A$ is benzyl and, $Z3_A$ is carboxy, methoxycarbonyl or ethoxycarbonyl;

(3) $X_A$ is N or O, $Z1_A$ and $Z3_A$ are hydrogen and, $Z2_A$ is carboxy or methoxycarbonyl;

(4) $X_A$ is O, $Z1_A$ is hydroxy or a group derived therefrom, $Z2_A$ is hydrogen and, $Z3_A$ is amino or a group derived therefrom;

(5) $X_A$ is S, $Y1_A$ is phenyl, $Z1_A$ is dimethoxymethyl and, $Z2_A$ and $Z3_A$ are hydrogen;

(6) $X_A$ is O, $Y1_A$ is methyl, $Z1_A$ is 1-methoxy-1-phenylthiomethyl and, $Z2_A$ and $Z3_A$ are hydrogen;

(7) $Z1_A$ is S, SO or $SO_2$, $Z2_A$ is hydroxy or a group derived therefrom and, $Z3_A$ is hydrogen.

53) A composition for promoting nerve cell differentiation comprising as an effective ingredient a cyclopentanone derivative of formula [1A] according to 1) above or a cyclopentanone derivative according to any one of 2) through 6) described above, or a pharmacologically acceptable salt thereof, wherein the cyclopentanone derivative further includes:

23

(1) when $Z1_A$ and $Z2_A$ are hydrogen, $X_A$ is S, $Y_A$ is methyl or benzyl and, $Z3_A$ is methoxycarbonyl, (2) when $Z1_A$ and $Z2_A$ are hydrogen, $X_A$ is O or N, $Y_A$ is benzyl and, $Z3_A$ is carboxy, methoxycarbonyl or ethoxycarbonyl;

(3) $X_A$ is N or O, $Z1_A$ and $Z3_A$ are hydrogen and, $Z2_A$ is carboxy or methoxycarbonyl;

(4) $X_A$ is O, $Z1_A$ is hydroxy or a group derived therefrom, $Z2_A$ is hydrogen and, $Z3_A$ is amino or a group derived therefrom;

(5) $X_A$ is S, $Y1_A$ is phenyl, $Z1_A$ is dimethoxymethyl and, $Z2_A$ and $Z3_A$ are hydrogen;

(6) $X_A$ is O, $Y1_A$ is methyl, $Z1_A$ is 1-methoxy-1-phenylthiomethyl and, $Z2_A$ and $Z3_A$ are hydrogen;

(7) $Z1_A$ is S, SO or $SO_2$, $Z2_A$ is hydroxy or a group derived therefrom and, $Z3_A$ is hydrogen.

54) A pharmaceutical composition comprising as an effective ingredient a 2,3-di-substituted cyclopentanone derivative of formula [1B] described in 1) above or a 2,3-di-substituted cyclopentanone derivative according to any one of 7) through 18) described above, or a pharmacologically acceptable salt thereof.

55) A composition for the treatment of central nervous disorders comprising as an effective ingredient a 2,3-di-substituted cyclopentanone derivative of formula [1B] described in 1) above or a 2,3-di-substituted cyclopentanone derivative according to any one of 7) through 18) described above, or a pharmacologically acceptable salt thereof.

56) A composition for the treatment of peripheral nervous disorders comprising as an effective ingredient a 2,3-di-substituted cyclopentanone derivative of formula [1B] described in 1) above or a 2,3-di-substituted cyclopentanone derivative according to any one of 7) through 18), or a pharmacologically acceptable salt thereof.

57) A composition for promoting nerve cell differentiation comprising as an effective ingredient a 2,3-di-substituted cyclopentanone derivative of formula [1B] described in 1) above or a 2,3-di-substituted cyclopentanone derivative according to any one of 7) through 18), or a pharmacologically acceptable salt thereof.

58) A pharmaceutical composition comprising as an effective ingredient a cyclopentenone derivative of formula [1C] described in 1) above or a cyclopentenone derivative according to any one of 19) through 26), or a pharmacologically acceptable salt thereof, wherein said cyclopentenone derivative further includes the cases that when $X_c$ is O or NH, $Z1_c$ and $Z3_c$ are hydrogen and, $Z2_c$ is hydrogen or, hydroxy or a group derived therefrom.

59) A composition for the treatment of central nervous disorders comprising as an effective ingredient a cyclopentenone derivative of formula [1C] described in 1) above or a cyclopentenone derivative according to any one of 19) through 26) described above, or a pharmacologically acceptable salt thereof, wherein said cyclopentenone derivative further includes the cases that when $X_c$ is O or NH, $Z1_c$ and $Z3_c$ are hydrogen and, $Z2_c$ is hydrogen or, hydroxy or a group derived therefrom.

60) A composition for the treatment of peripheral nervous disorders comprising as an effective ingredient a cyclopentenone derivative of formula [1C] described in 1) above or a cyclopentenone derivative according to any one of 19) through 26) described above, or a pharmacologically acceptable salt thereof, wherein said cyclopentenone derivative further includes the cases that when $X_c$ is O or NH, $Z1_c$ and $Z3_c$ are hydrogen and, $Z2_c$ is hydrogen or, hydroxy or a group derived therefrom.

24

61) A composition for promoting nerve cell differentiation comprising as an effective ingredient a cyclopentenone derivative of formula [1C] described in 1) above or a cyclopentenone derivative according to any one of 19) through 26) described above, or a pharmacologically acceptable salt thereof, wherein said cyclopentenone derivative further includes the cases that when $X_c$ is O or NH, $Z1_c$ and $Z3_c$ are hydrogen and, $Z2_c$ is hydrogen or, hydroxy or a group derived therefrom.

62) A pharmaceutical composition comprising as an effective ingredient a ketone derivative of formula [1D] according to 1) above or a ketone derivative according to any one of 26) through 38) described above, or a pharmacologically acceptable salt thereof, wherein, when $A_D$ and $B_D$ are combined together to form a cyclobutane ring, the ketone derivative further includes (1) through (4):

(1) $X_D$ is O, $Y_D$ is methyl, n-octyl or n-hexadecyl and, $Z_D$ is methoxycarbonyl;

(2) $X_D$ is O, $Y_D$ is benzyl and, $Z_D$ is benzyloxylmethyl;

(3) $X_D$ is O, $Y_D$ is p-methoxybenzyl and, $Z_D$ is p-methoxybenzyloxymethyl; and, (4) $X_D$ is O, $Y_D$ is trityl and $Z_D$ is trityloxymethyl and when $A_D$ is an unsubstituted benzene ring and $B_D$ is hydrogen, $X_D$ is S, $Y_D$ is methyl, ethyl or isopropyl and $Z_D$ is carboxy.

63) A composition for the treatment of central nervous disorders comprising as an effective ingredient a ketone derivative of formula [1D] according to 1) above or a ketone derivative according to any one of 26) through 38) described above, or a pharmacologically acceptable salt thereof, wherein, when $A_D$ and $B_D$ are combined together to form a cyclobutane ring, the ketone derivative further includes (1) through (4):

(1) $X_D$ is O, $Y_D$ is methyl, n-octyl or n-hexadecyl and, $Z_D$ is methoxycarbonyl;

(2) $X_D$ is O, $Y_D$ is benzyl and, $Z_D$ is benzyloxylmethyl;

(3) $X_D$ is O, $Y_D$ is p-methoxybenzyl and, $Z_D$ is p-methoxybenzyloxymethyl; and, (4) $X_D$ is O, $Y_D$ is trityl and $Z_D$ is trityloxymethyl and when $A_D$ is an unsubstituted benzene ring and $B_D$ is hydrogen, $X_D$ is S, $Y_D$ is methyl, ethyl or isopropyl and $Z_D$ is carboxy.

64) A composition for the treatment of peripheral nervous disorders comprising as an effective ingredient a ketone derivative of formula [1D] according to 1) above or a ketone derivative according to any one of 26) through 38) described above, or a pharmacologically acceptable salt thereof, wherein, when $A_D$ and $B_D$ are combined together to form a cyclobutane ring, the ketone derivative further includes (1) through (4):

(1) $X_D$ is O, $Y_D$ is methyl, n-octyl or n-hexadecyl and, $Z_D$ is methoxycarbonyl;

(2) $X_D$ is O, $Y_D$ is benzyl and, $Z_D$ is benzyloxylmethyl;

(3) $X_D$ is O, $Y_D$ is p-methoxybenzyl and, $Z_D$ is p-methoxybenzyloxymethyl; and, (4) $X_D$ is O, $Y_D$ is trityl and $Z_D$ is trityloxymethyl and when $A_D$ is an unsubstituted benzene ring and $B_D$ is hydrogen, $X_D$ is S, $Y_D$ is methyl, ethyl or isopropyl and $Z_D$ is carboxy.

65) A composition for promoting nerve cell differentiation comprising as an effective ingredient a ketone derivative of formula [1D] according to 1) above or a ketone derivative according to any one of 26) through 38) described above, or a pharmacologically acceptable salt thereof, wherein, when $A_D$ and $B_D$ are combined together to form a cyclobutane ring, the ketone derivative further includes (1) through (4):

(1) $X_D$ is O, $Y_D$ is methyl, n-octyl or n-hexadecyl and, $Z_D$ is methoxycarbonyl;

(2) $X_D$ is O, $Y_D$ is benzyl and, $Z_D$ is benzyloxymethyl;

(3) $X_D$ is O, $Y_D$ is p-methoxybenzyl and, $Z_D$ is p-methoxybenzyloxymethyl; and, (4) $X_D$ is O, $Y_D$ is trityl and $Z_D$ is trityloxymethyl and when $A_D$ is an unsubstituted benzene ring and $B_D$ is hydrogen, $X_D$ is S, $Y_D$ is methyl, ethyl or isopropyl and $Z_D$ is carboxy.

66) A pharmaceutical composition comprising as an effective ingredient a compound of formula [1E] according to 1) above or a pharmacologically acceptable salt thereof.

67) A composition for the treatment of central nervous disorders comprising as an effective ingredient a compound of formula [1E] according to 1) above or a pharmacologically acceptable salt thereof.

68) A composition for the treatment of peripheral nervous disorders comprising as an effective ingredient a compound of formula [1E] according to 1) above or a pharmacologically acceptable salt thereof.

69) A composition for promoting nerve cell differentiation comprising as an effective ingredient a compound of formula [1E] according to 1) above or a pharmacologically acceptable salt thereof.

70) A pharmaceutical composition comprising as an effective ingredient a β-di-substituted aminoketone derivative of formula [1F] according to 1) above or β-di-substituted aminoketone derivative according to any of 39)~49) described above, or a pharmacologically acceptable salt thereof, wherein, when $A_F$ is an unsubstituted benzene ring, the β-di-substituted aminoketone derivative further includes those wherein $B_F$ is hydrogen, $X_F$ is bound directly to $Y_F$ to form a piperidine ring and, $Z_F$ is carboxy.

71) A composition for the treatment of central nervous disorders comprising as an effective ingredient a β-di-substituted aminoketone derivative of formula [1F] according to 1) above or a β-di-substituted aminoketone derivative according to any of 39)~49) described above, or a pharmacologically acceptable salt thereof, wherein, when $A_F$ is an unsubstituted benzene ring, the β-di-substituted aminoketone derivative further includes those wherein $B_F$ is hydrogen, $X_F$ is directly bound to $Y_F$ to form a piperidine ring and, $Z_F$ is carboxy.

72) A composition for the treatment of peripheral nervous disorders comprising as an effective ingredient a β-di-substituted aminoketone derivative of formula [1F] according to 1) above or a β-di-substituted aminoketone derivative according to any of 39)~49) described above, or a pharmacologically acceptable salt thereof, wherein, when $A_F$ is an unsubstituted benzene ring, the β-di-substituted aminoketone derivative further includes those wherein $B_F$ is hydrogen, $X_F$ is directly bound to $Y_F$ to form a piperidine ring and, $Z_F$ is carboxy.

73) A composition for promoting nerve cell differentiation comprising as an effective ingredient a β-di-substituted aminoketone derivative of formula [1F] according to 1) above or a β-di-substituted aminoketone derivative according to any of 39)~49) described above, or a pharmacologically acceptable salt thereof, wherein, when $A_F$ is an unsubstituted benzene ring, the β-di-substituted aminoketone derivative further includes those wherein $B_F$ is hydrogen, $X_F$ is directly bound to $Y_F$ to form a piperidine ring and, $Z_F$ is carboxy.

BEST MODE FOR CARRYING OUT THE INVENTION

Figure 1:
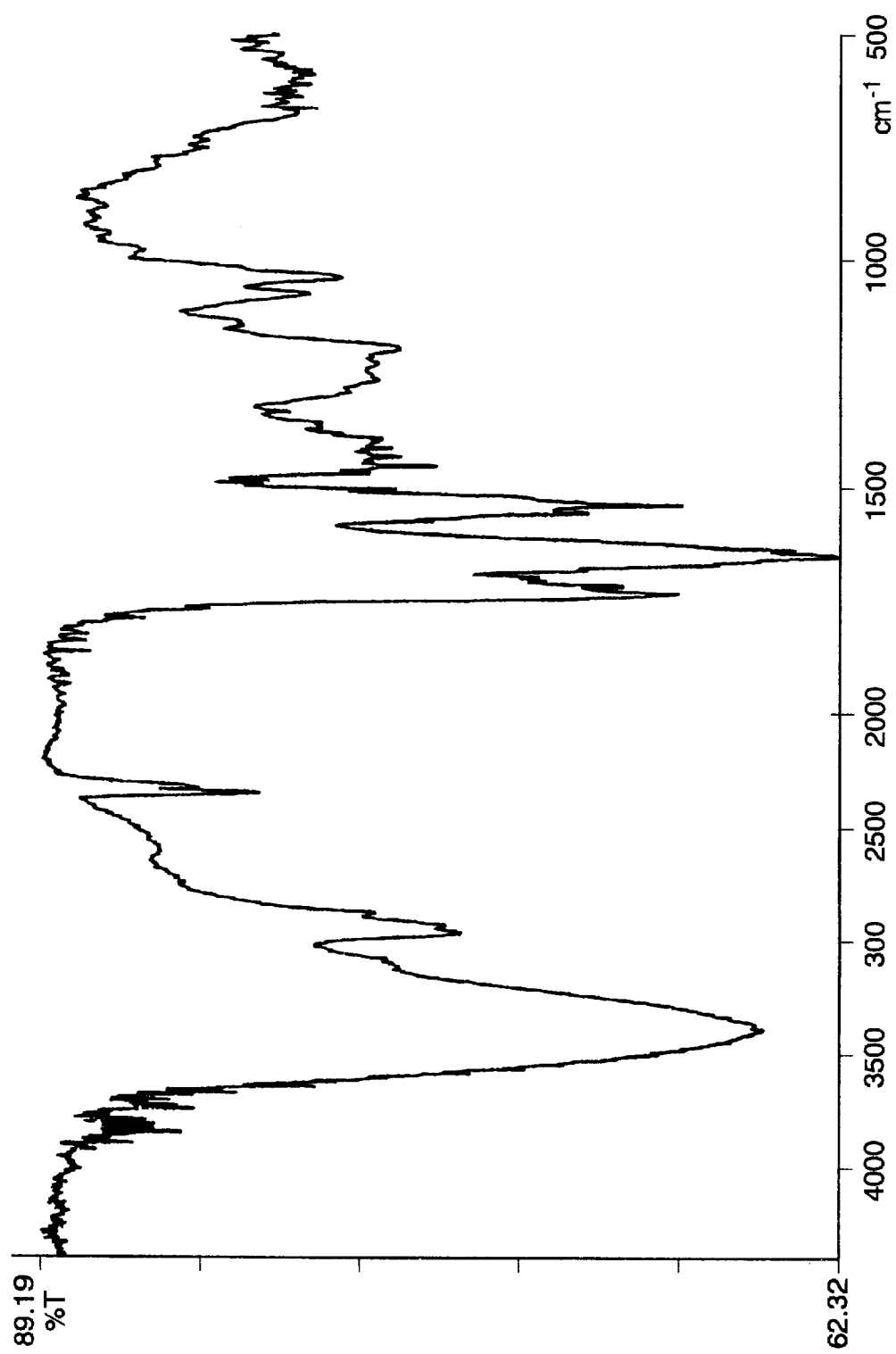
FIG. 1 shows the infrared absorption spectrum of NA32176A (compound of formula [1E]) measured using a potassium bromide tablet.

The compounds of the present invention represented by formulas [1A], [1B], [1C], [1D], [1E] and [1F] exhibit a neuron differentiation promoting activity and can be used as medicaments for the treatment of nerve disturbances in the central and peripheral nervous systems.

The compounds of the present invention will be described below in more detail.

[A] Compounds of formula [1A]

In the general formula [1A], $X_A$ is preferably O, S or SO, most preferably S.

The straight or branched aliphatic group having 1 to 20 carbon atoms, which is shown by $Y_A$ in the general formula [1A], refers to an alkyl or alkenyl having 1 to 20 carbon atoms, preferably an alkyl having 1 to 6 carbon atoms, e.g., methyl, ethyl, n-propyl, n-butyl, n-pentyl, n-hexyl, isopropyl or tert-butyl, more preferably a straight aliphatic group having 1 to 4 carbon atoms, most preferably, ethyl. The aliphatic group may be either unsubstituted or substituted. Where the aliphatic group is substituted, 1 to 6, preferably 1 to 3 substituents may be present on the aliphatic group. Examples of such substituents are carboxy or a group derived therefrom, amino or a group derived therefrom, or hydroxy or a group derived therefrom.

In the aromatic hydrocarbon and monocyclic aromatic heterocyclic ring having 3 to 6 carbon atoms in the general formula [1A], the aromatic hydrocarbon group is preferably a benzene ring and the monocyclic aromatic heterocyclic ring refers to a 5- or 6-membered ring containing a nitrogen, oxygen or sulfur atom. Where these groups are substituted, examples of the substituents are the same as given for the aliphatic group.

The group derived from carboxy includes a carboxy-functional group such as an esterified or amidated carboxy group, cyano, hydroxymethyl or aminomethyl formed by reducing these functional groups, and functional groups derived therefrom by modification like acylation of the functional groups. Preferably, the carboxy and the group derived therefrom include carboxy, COOR1 (wherein R1 is a substituted or unsubstituted alkyl, alkenyl or alkynyl having 1 to 4 carbon atoms), and COW (wherein W is an unsubstituted or substituted saturated heterocyclic ring. The alkyl, alkenyl or alkynyl shown by R1 for COOR1 may be straight, branched or cyclic. When R1 is substituted 1 to 6, preferably 1 to 3 substituents may be present on R1, and examples of the substituent are a halogen, hydroxy, carboxy, methoxycarbonyl, cyano and acetylamino. R1 is preferably unsubstituted. Examples of the alkyl group are methyl, ethyl, ethylene, n-propyl, isopropyl, cyclopropyl, n-butyl, isobutyl, tert-butyl and cyclobutyl, preferably methyl, ethyl, ethylene and n-propyl, more preferably methyl. Examples of the alkenyl group are vinyl, 2-propenyl, isopropenyl and 2-butenyl. A typical example of the alkynyl group is 2-propenyl. W represents a heterocyclic ring, preferably a saturated heterocyclic ring, more preferably an azetidine, piperidine, pyrrolidine, morpholine or piperazine ring. These heterocyclic rings may be linked to carbonyl via a carbon or nitrogen atom, preferably linked to carbonyl via nitrogen. Where the heterocyclic ring is substituted, 1 to 4, preferably 1 to 2 substituents may be present on each ring. Preferred examples of the substituents are carboxy and a group derived therefrom, more preferably carboxy and COOR11 (wherein R11 is an unsubstituted or substituted alkyl having 1 to 4 carbon atoms; in this case, examples of the alkyl and the substituents where the alkyl is substituted are the same as in R1 described above).

Examples of the group derived from amino include such functional groups that amino is alkylated, acylated or sulfonated, nitro, hydroxyamino, imino and a heterocyclic group containing the nitrogen atom of amino, preferably a group shown by NR2R3 (wherein each of R2 and R3, which may be different or the same, independently represents hydrogen, an unsubstituted or substituted alkyl having 1 to 4 carbon atoms or an unsubstituted or substituted acyl having 1 to 5 carbon atoms). In the group shown by NR2R3, the alkyl for R2 and R3 and the substituents where the alkyl is substituted are the same as in R1. The acyl for R2 and R3 may be straight, branched, cyclic, saturated or unsaturated. Where the acyl is substituted, the substituents are the same as in R1. More preferably, the amino-derived group is represented by NHCOR12 (wherein R12 is an alkyl having 1 to 4 carbon atoms and examples of R12 are the same as in R1), and most preferably, R12 is methyl.

Examples of the group derived from hydroxy include a functional group in which hydroxy is alkylated or acylated, e.g., OCOR14 (wherein the alkylated functional group in R14 is an unsubstituted or substituted alkyl and examples of the alkyl are the same as in R1; and the acylated functional group in R14 is an unsubstituted or substituted acyl and examples of the acyl are the same as in R2), a keto and a halogen.

Each of $Z1_A$, $Z2_A$ and $Z3_A$ in the compounds of formula [1A] represents carboxy or a group derived therefrom, an unsubstituted or substituted alkyl having 1 to 4 carbon atoms, hydroxy or a group derived therefrom, amino or a group derived therefrom, sulfate or a group derived therefrom, phosphate or a group derived therefrom, a monocyclic aromatic heterocyclic ring, a halogen or hydrogen; or $Z2_A$ and $Z3_A$ are combined together to form a substituted or unsubstituted aromatic hydrocarbon or a aromatic heterocyclic ring; in this case $Z1_A$ is carboxy or a group derived therefrom, an unsubstituted or substituted alkyl having 1 to 4 carbon atoms, hydroxy or a group derived therefrom, amino or a group derived therefrom, a halogen or hydrogen. Examples of the group derived from sulfate are groups from sulfonamide derivatives, such as $SO_2NH_2$, $SO_2NHCH_3$, $SO_2N(CH_3)_2$ and $SO_2NHCOCH_3$. Examples of the group derived from phosphate are $P(O)(OH)H$, $P(O)(OH)(NH_2)$ and $P(O)(OH)CH(OCH_3)_2$. Examples of the groups derived from carboxy, hydroxy and amino are the same as described above. Examples of the group derived from amino further include $NHSO_2Ph$, $NHCOCF_3$, $NHCOC_2F_5$, $NHSO_2CF_3$ and $NHSO_2C_2F_5$. Preferred examples of $Z1_A$, $Z2_A$ and $Z3_A$ include carboxy, COOR4 (wherein R4 is an unsubstituted or substituted alkyl having 1 to 4 carbon atoms), CONR5R6 (wherein each of R5 and R6, which may be different or the same, independently represents hydrogen or a substituted or unsubstituted alkyl having 1 to 4 carbon atoms), cyano, hydroxy, OR7 (wherein R7 is an unsubstituted or substituted alkyl having 1 to 4 carbon atoms or an unsubstituted or substituted acyl having 1 to 5 carbon atoms), NR8R9 (wherein each of R8 and R9, which may be the same or different, independently represents hydrogen, an unsubstituted or substituted alkyl having 1 to 4 carbon atoms or an unsubstituted or substituted acyl having 1 to 5 carbon atoms), $CH_2OR10$ (wherein R10 is hydrogen, an unsubstituted or substituted alkyl having 1 to 4 carbon atoms or an unsubstituted or substituted acyl having 1 to 5 carbon atoms), 5-tetrazolyl, a halogen or hydrogen. Examples of the aforesaid unsubstituted or substituted alkyl having 1 to 4 carbon atoms, the alkyl shown by R4, R5, R6, R7, R8, R9 or R10 and the substituents when these groups are substituted are the same as in R1. Examples of the acyl shown by R7, R8, R9 or R10 and the substituents when these groups are substituted are the same as in R2. Specific examples of the acyl are acetyl, propionyl, acroyl, propioloyl, n-butyryl, isobutyryl, crotonoyl, valeryl, isovaleryl and pivaloyl, preferably acetyl, propionyl, acroyl and propioloyl, more preferably acetyl. A particularly preferred combination of R8 and R9 is that R8 is hydrogen and R9 is acetyl. Examples of the halogen are fluorine, chlorine, bromine and iodine, preferably fluorine and chlorine. Preferred examples of the substituents for $Z1_A$, $Z2_A$ and $Z3_A$ are the case where one or two are substituents other than hydrogen, more preferably, substituents such as carboxy, COOR4, OCOR13 (wherein R13 is an alkyl having 1 to 4 carbon atoms and examples of the alkyl are the same as in those of R1), hydroxy and $CH_2OR10$, most preferably, carboxy, methoxycarbonyl, hydroxymethyl, hydroxy and acetyloxymethyl.

Examples of the aromatic hydrocarbon formed by combining $Z2_A$ and $Z3_A$ are a benzene ring and a naphthalene ring. Examples of the aromatic heterocyclic ring formed by $Z2_A$ and $Z3_A$ are a 6-membered heteroaryl such as a pyridine, pyrazine or pyrimidine ring, and a 5-membered aromatic heterocyclic ring such as a thiophene, pyrrole, furan, oxazole, thiazole, isoxazole, isothiazole or azole ring. Preferably, the group formed by $Z2_A$ and $Z3_A$ is an aromatic hydrocarbon, more preferably a benzene ring. When the ring is substituted, examples of the substituents are the same as in those of Z. Preferred examples of the substituents include an alkyl having 1 to 4 carbon atoms, preferably, methyl, ethyl, n-propyl and isopropyl, which may be unsubstituted or substituted with a halogen (e.g., fluorine) such as trifluoromethyl; an alkyloxy having 1 to 4 carbon atoms such as methoxy and ethoxy; nitro, and a halogen, e.g., fluorine, chlorine or bromine.

[B] Compounds of formula [1B]

In the compounds of the present invention represented by formula [1B], $X_B$ ?? is preferably S, O or SO, most preferably S.

The straight or branched aliphatic hydrocarbon group having 7 to 20 carbon atoms, which is shown by YB, refers to an alkyl or alkenyl group having 7 to 20 carbon atoms. Examples of the alkyl or alkenyl are n-pentyl, n-octyl, n-nonyl, n-decanyl, n-undecanyl, n-dodecanyl, n-tridecanyl, n-tetradecanyl, n-pentadecanyl, n-dodecanyl, n-hexadecanyl, n-pentadecanyl and n-octadecanyl, preferably an alkyl having 7 to 15 carbon atoms, most preferably n-dodecyl. The aliphatic hydrocarbon group may be unsubstituted or substituted. Where the aliphatic hydrocarbon group is substituted, the aliphatic group may have, for example, 1 to 6, preferably 1 to 3 substituents thereon. As such substituents, there are carboxy or a group derived therefrom, amino or a group derived therefrom, hydroxy or a group derived therefrom.

The group derived from carboxy includes a carboxy-functional group such as an esterified or amidated carboxy group, cyano, hydroxymethyl or aminomethyl formed by reducing these functional groups, and functional groups derived therefrom by modification like acylation of the functional groups. Preferably, the carboxy and the group derived therefrom include carboxy and COOR6 (wherein R6 is an unsubstituted or substituted alkyl, alkenyl or alkynyl having 1 to 4 carbon atoms). The alkyl, alkenyl or alkynyl shown by R6 in COOR6 may be straight, branched or cyclic. Where R6 is substituted, examples of the substituent are a halogen, hydroxy, carboxy, methoxycarbonyl, cyano and acetamido. R6 is preferably unsubstituted. Examples of the alkyl group are methyl, ethyl, ethylene, n-propyl, isopropyl, cyclopropyl, n-butyl, isobutyl, tert-butyl and cyclobutyl, preferably methyl, ethyl, ethylene and n-propyl. Examples of the alkenyl group are vinyl, 2-propenyl, isopropenyl and 2-butenyl. A typical example of the alkynyl group is 2-propenyl.

Examples of the group derived from amino include such functional groups that amino is alkylated, acylated or sulfonated, nitro, hydroxyamino, imino and a heterocyclic group containing the nitrogen atom of amino, preferably a group shown by NR7R8 (wherein each of R7 and R8, which may be different or the same, independently represents hydrogen, an unsubstituted or substituted alkyl having 1 to 4 carbon atoms or an unsubstituted or substituted acyl having 1 to 5 carbon atoms). In the group shown by NR7R8, the alkyl for R7 and R8 and the substituents where the alkyl is substituted are the same as in R6. The acyl for R7 and R8 may be straight, branched, cyclic, saturated or unsaturated. Where the acyl is substituted, the substituents are the same as in R6. Representative examples of the acyl are acetyl, propionyl, acroyl, propioloyl, n-butyryl, isobutyryl, crotonoyl, valeryl, isovaleryl and pivaloyl, preferably acetyl, propionyl, acroyl and propioloyl, more preferably acetyl. A particularly preferred combination of R7 and R8 is that R7 is hydrogen and R8 is acetyl.

Examples of the group derived from hydroxy include a functional group in which hydroxy is alkylated or acylated, e.g., OCOR14 (wherein the alkylated functional group in R14 is an unsubstituted or substituted alkyl and examples of the alkyl are the same as in R6; and the acylated functional group in R14 is an unsubstituted or substituted acyl and examples of the acyl are the same as in R7), a keto and a halogen.

In the compounds of general formula [1B], the straight or branched aliphatic group having 1 to 6 carbon atoms, which is substituted with COW, is exemplified by methyl, ethyl, n-propyl, n-butyl, n-pentyl, n-hexyl, isopropyl and tert-butyl, preferably a straight aliphatic group having 1 to 4 carbon atoms, more preferably ethyl. In the aliphatic group, at least one hydrogen, preferably one hydrogen, should be substituted with COW. W represents an unsubstituted or substituted heteroaryl or a saturated aromatic heterocyclic ring, preferably a saturated aromatic heterocyclic ring, more preferably an azetidine, piperidine, pyrrolidine, piperazine or morpholine ring. These heterocyclic rings may be linked to carbonyl via a carbon or nitrogen atom, preferably via nitrogen. Where the heterocyclic ring is substituted, each ring may contain 1 to 4, preferably 1 to 2 substituents thereon. Preferred examples of the substituents are carboxy, a hydroxyalkyl having 1 to 4 carbon atoms, phenyl or COOR9 (wherein R9 is an unsubstituted or substituted alkyl having 1 to 4 carbon atoms; in this case, examples of the alkyl and the substituents where the alkyl is substituted are the same as in R6 described above). Examples of the hydroxyalkyl are 2-hydroxyethyl, 3-hydroxypropyl and 4-hydroxybutyl, preferably 2-hydroxyethyl. COOR9 is preferably tert-butoxycarbonyl. In the COOR9, at least one hydrogen, preferably one hydrogen may be substituted with amino or a group derived therefrom. Examples of the group derived from amino are the same as described above, preferably NR10R11 (wherein each of R10 and R11, which may be the same or different, independently represents hydrogen, an unsubstituted or substituted alkyl having 1 to 4 carbon atoms or an unsubstituted or substituted acyl having 1 to 5 carbon atoms). In the group shown by NR10R11, examples of the alkyl and the substituents where the alkyl is substituted are the same as those given for R6. In the group shown by NR10R11, the acyl for R10 and R11 may be straight, branched, cyclic, saturated or unsaturated. Where the acyl is substituted, the substituents are the same as those given for R6, preferably NHCOR12 (wherein R12 is an alkyl having 1 to 4 carbon atoms and examples of the alkyl are the same as those given for R6).

In the compounds of general formula [1B], examples of the straight or branched aliphatic group having 1 to 6 carbon atoms and substituted with NHCOV1 are methyl, ethyl, n-propyl, n-butyl, n-pentyl, n-hexyl, isopropyl and tert-butyl, preferably a straight aliphatic group having 1 to 4 carbon atoms, more preferably ethyl. In the aliphatic group, at least one hydrogen, preferably one hydrogen, should be substituted with NHCOV1. V represents an alkyl having 2 to 5 carbon atoms, which contains 4 to 11 halogen atoms. Examples of the halogen are fluorine, chlorine, bromine and iodine, preferably fluorine. Specific examples of the NHCOV1-substituted alkyl are tetrafluoroethyl, heptafluoro-n-propyl, nonafluoro-n-butyl and undecafluoro-n-pentyl. In this aliphatic hydrocarbon group, at least one hydrogen, preferably one hydrogen may be substituted with carboxy or a group derived therefrom. Examples of the carboxy-derived group are the same as those described above, preferably carboxy or COOR13 (wherein R13 is an unsubstituted or substituted alkyl having 1 to 4 carbon atoms, an alkenyl or an alkynyl, and examples of these groups are the same as those given for R6), more preferably carboxy.

In $Y_B$ of the compounds represented by general formula [1B], the aryl having 3 to 6 carbon atoms refers to, e.g., a benzene ring and the monocyclic aromatic heterocyclic ring having 3 to 6 carbon atoms refers to a 5- or 6-membered ring containing nitrogen, oxygen or sulfur. Where the aromatic hydrocarbon ring or monocyclic aromatic heterocyclic ring is substituted, examples of such substituents are the same as those given for the aliphatic group above.

In $Y_B$ in the compounds represented by general formula [1B], the straight or branched aliphatic group having 1 to 6 carbon atoms, which is substituted with a monocyclic aromatic heterocyclic ring, is exemplified by methyl, ethyl, n-propyl, n-butyl, n-pentyl, n-hexyl, isopropyl and tert-butyl, preferably a straight aliphatic group having 1 to 4 carbon atoms, more preferably ethyl and n-propyl. In the aliphatic hydrocarbon group, at least one hydrogen, preferably one hydrogen, should be substituted with monocyclic aromatic heterocyclic ring. Examples of the monocyclic aromatic heterocyclic ring are a pyridine, pyrazine, pyrimidine, indole, pyrrole, imidazole, triazole, tetrazole, furan and thiophene ring, preferably pyridine or tetrazole. These heterocyclic rings may be linked to the aliphatic group via carbon or nitrogen, preferably via carbon. Where the heterocyclic ring is substituted, each ring may contain 1 to 4, preferably 1 to 2 substituents thereon. Examples of the substituents are an alkyl having 1 to 4 carbon atoms, preferably methyl. In this aliphatic group, at least one hydrogen, preferably one hydrogen may be substituted with amino or a group derived therefrom. Examples of the group derived from amino are the same as described above, preferably NR15R16 (wherein each of R15 and R16, which may be the same or different, independently represents hydrogen, an unsubstituted or substituted alkyl having 1 to 4 carbon atoms or an unsubstituted or substituted acyl having 1 to 5 carbon atoms). In the group shown by NR15R16, examples of the alkyl and the substituents where the alkyl is substituted are the same as those given for R6. The acyl may be straight, branched, cyclic, saturated or unsaturated. Where the acyl is substituted, the substituents are the same as those given for R6, preferably NHCOR17 (wherein R17 is an alkyl having 1 to 4 carbon atoms and examples of the alkyl are the same as those given for R6).

In the compounds represented by general formula [1B], $Z_B$ is carboxy or a group derived therefrom, sulfate or a group derived therefrom, phosphate or a group derived therefrom, an unsubstituted or substituted alkyl having 1 to 4 carbon atoms, hydroxy, OR1 (wherein R1 is an unsubstituted or substituted alkyl having 1 to 4 carbon atoms or an unsubstituted or substituted acyl having 1 to 5 carbon atoms), NHCOR2 (wherein R2 is an unsubstituted or substituted alkyl having 1 to 4 carbon atoms), $NHSO_2R2'$ (wherein R2' is an unsubstituted or substituted alkyl having 1 to 4 carbon atoms or phenyl), a monocyclic aromatic heterocyclic ring, a halogen or hydrogen. Examples of the carboxy-derived group are the same as those described above. Examples of the group derived from sulfate are groups from sulfonamide derivatives, such as $SO_2NH_2$, $SO_2NHCH_3$, $SO_2N(CH_3)_2$ and $SO_2NHCOCH_3$. Examples of the group derived from phosphate are $P(O)(OH)H$, $P(O)(OH)(NH_2)$ and $P(O)(OH)CH(OCH_3)_2$. Examples of the alkyl having 1 to 4 carbon atoms, the alkyl shown by R1, R2 and R2' and the substituents when these alkyl groups are substituted are the same as those given for R6. Examples of the acyl in R1 and the substituents when the acyl is substituted are the same as those given for R7. Examples of NHCOR2 are $NHCOCH_3$, $NHCOCF_3$ and $NHCOC_2F_5$. Examples of $NHSO_2R2'$ are $NHSO_2Ph$, $NHSO_2CF_3$ and $NHSO_2C_2F_5$. A preferred example of the monocyclic heteroaryl is 5-tetrazolyl. In $Z_R$, examples of the halogen are fluorine, chlorine, bromine and iodine, preferably fluorine and chlorine. Preferred examples of Z are carboxy, COOR3 (wherein R3 is an unsubstituted or substituted alkyl having 1 to 4 carbon atoms and examples of the alkyl and substituents on the alkyl are those given for R6), $CH_2OR4$ (wherein R4 is an unsubstituted or substituted alkyl having 1 to 4 carbon atoms and examples of the alkyl and substituents on the alkyl are those given for R6), and $CH_2OCOR5$ (wherein R5 is an unsubstituted or substituted alkyl having 1 to 4 carbon atoms and examples of the alkyl and substituents on the alkyl are those given for R6), more preferably, carboxy, methoxycarbonyl, hydroxymethyl and acetyloxymethyl.

[C] Compounds of formula [1C]

In the present invention, ring A in the compounds represented by general formula [1C] represents a 2-cyclopenten-1-one ring, which includes cases that the $Y_c$—$X_c$—$CH_2$ moiety is bound to the carbon with a double bond and the carbon with a single bond.

In the compounds of the present invention represented by formula [1C], $X_c$ is preferably S, O or SO, most preferably S.

In $Y_c$ in the compounds represented by general formula [1C], the straight or branched aliphatic group having 1 to 6 carbon atoms includes an alkyl or an alkenyl. Examples of the alkyl are methyl, ethyl, n-propyl, n-butyl, n-pentyl, n-hexyl, isopropyl and tert-butyl. Examples of the alkenyl are vinyl, 2-propenyl, isopropenyl and 2-butenyl. Preferably the aliphatic hydrocarbon group is an alkyl having 1 to 4 carbon atoms, more preferably ethyl. The aliphatic hydrocarbon group may be unsubstituted or substituted. Where the aliphatic hydrocarbon group is substituted, it may contain 1 to 6, preferably 1 to 4 substituents. As such substituents, there are carboxy or a group derived therefrom, amino or a group derived therefrom and, hydroxy or a group derived therefrom. The aromatic hydrocarbon ring or monocyclic aromatic heterocyclic ring having 3 to 6 carbon atoms refers to an aromatic hydrocarbon ring such as a benzene ring and a aromatic heterocyclic ring such as a 5- or 6-membered ring containing nitrogen, oxygen or sulfur. Where the aromatic hydrocarbon ring or aromatic heterocyclic ring is substituted, examples of such substituents are the same as those given for the aliphatic hydrocarbon group.

The group derived from carboxy includes a carboxy-functional group such as an esterified or amidated carboxy group, cyano, hydroxymethyl or aminomethyl formed by reducing these functional groups, and functional groups derived therefrom by modification like acylation or alkylation of the functional groups. Preferably, the carboxy and the group derived therefrom include carboxy, COOR1 (wherein R1 is an unsubstituted or substituted alkyl or alkenyl having 1 to 4 carbon atoms), CONR2R3 (wherein each of R2 and R3, which may be different or the same, independently represents hydrogen or a substituted or unsubstituted alkyl having 1 to 4 carbon atoms), and COW (W represents unsaturated or saturated heterocyclic ring). Herein, the alkyl shown by R1 for COOR1 may be straight, branched or cyclic. Examples of the alkyl group are methyl, ethyl, n-propyl, isopropyl, cyclopropyl, n-butyl, isobutyl, tert-butyl and cyclobutyl, preferably methyl, ethyl, and n-propyl, and more preferably methyl. Examples of the alkenyl are vinyl, 2-propenyl, isopropenyl and 2-butenyl. When substituted, for example, 1 to 6, preferably 1 to 3 substituents may be present. Examples of the substituents are a halogen, hydroxy, thiol, carboxy, methoxycarbonyl, acetyloxy, acetylthio, cyano and acetylamino. Examples of the halogen are bromine, chlorine and fluorine. Preferably, the substituent on R1 is unsubstituted.

Where the alkyl shown by R2 or R3 and its substituent(s) are substituted, examples of such substituents are the same as those given for R1.

Preferably W represents a saturated heterocyclic ring, more preferably, an azetidine, piperidine, pyrrolidine, piperazine or morpholine ring. These heterocyclic rings may be linked to carbonyl via carbon or nitrogen, preferably linked to carbonyl via nitrogen. Where the heterocyclic ring is substituted, 1 to 4, preferably 1 to 2 substituents may be present on each ring. Examples of the substituents are carboxy or a group derived therefrom and amino or a group derived therefrom. Examples of these groups are described in the specification.

Examples of the group derived from amino include such functional groups that amino is alkylated or acylated, nitro, hydroxyamino, imino and a heterocyclic group containing the nitrogen atom of amino, preferably a group shown by NR4R5 (wherein each of R4 and R5, which may be different or the same, independently represents hydrogen, an unsubstituted or substituted alkyl having 1 to 4 carbon atoms or an unsubstituted or substituted acyl having 1 to 5 carbon atoms). In the group shown by NR4R5, the alkyl for R4 and R5 and the substituents where the alkyl is substituted are the same as those in R1. The acyl for R4 and R5 may be straight, branched, cyclic, saturated or unsaturated. Representative examples of the acyl are acetyl, propionyl, acroyl, propioloyl, n-butyryl, isobutyryl, crotonoyl, valeryl, isovaleryl and pivaloyl. Where the acyl is substituted, the substituents are the same as those in R1. Preferably, the amino-derived group is NHCOR14 (wherein R14 is an alkyl having 1 to 4 carbon atoms in which hydrogen(s) may be substituted with fluorine(s); examples of the alkyl are the same as those in R1). The number of fluorine atoms which may be substituted is 1 to 9, preferably 1 to 7. Most preferably, R14 is methyl.

Examples of the group derived from hydroxy include a functional group in which hydroxy is alkylated or acylated, a keto and a halogen, preferably OCOR15 (wherein R15 is an alkyl having 1 to 4 carbon atoms and examples of the alkyl are the same as those in R1).

In the cyclopentenone derivatives of general formula [1C], each of $Z1_c$, $Z2_c$ and $Z3_c$ represents carboxy or a group derived therefrom, an unsubstituted or substituted alkyl or alkenyl having 1 to 4 carbon atoms, hydroxy or a group derived therefrom, amino or a group derived therefrom, a monocyclic aromatic heterocyclic ring, a halogen or hydrogen. Examples of the group derived from carboxy, amino or hydroxy are the same as described above. Examples of the alkyl and alkenyl and substituents when the alkyl and alkenyl are substituted are the same as those given for A. Preferred examples of $Z1_c$, $Z2_c$ and $Z3_c$ are carboxy, COOR7 (wherein R7 is an unsubstituted or substituted alkyl having 1 to 4 carbon atoms), cyano, hydroxy, CH2OR10 (wherein R10 is a hydrogen, an unsubstituted or substituted alkyl having 1 to 4 carbon atoms, or an unsubstituted or substituted acyl having 1 to 5 carbon atoms), OCOR11 (wherein R11 is an unsubstituted or substituted alkyl having 1 to 4 carbon atoms), NR12R13 (wherein each of R12 and R13, which may be different or the same, independently represents a hydrogen, an unsubstituted or substituted alkyl having 1 to 4 carbon atoms, or an unsubstituted or substituted acyl having 1 to 5 carbon atoms), 5-tetrazolyl, chlorine, fluorine, or hydrogen. The alkyl for R7, R8, R9, R10, R11, R12 and R13 and substituents when the alkyl is substituted are the same as those given for R1. Further, the acyl for R10, R12 and R13 and substituents when the acyl is substituted are the same as those given for R4. Preferred combination of R12 and R13 is that R12 is a hydrogen and R13 is acetyl. Examples of the halogen are fluorine, chlorine, bromine and iodine, preferably fluorine and chlorine. Preferred examples of substituents $Z1_c$, $Z2_c$ and $Z3_c$ are the case that all of the substituents are hydrogen, or that one or two are substituents other than hydrogen. More preferred examples of the substituents are, except for hydrogen, carboxy, COOR7' (wherein R7' is an alkyl having 1 to 4 carbon atoms) and $CH_2OR10'$ (wherein R10' is hydrogen, an unsubstituted or substituted acyl having 1 to 5 carbon atoms). Examples of R7' are the same as those given for R1. Examples of the acyl in R10' are the same as those given for R4, most preferably, carboxy, methoxycarbonyl, hydroxymethyl and acetyloxymethyl.

[D] Compounds of formula [1D]

In the ketone derivative of the present invention represented by general formula [1D], the unsubstituted or substituted aliphatic hydrocarbon group having 1 to 4 carbon atoms, which is shown by $A_D$, refers to an alkyl or alkenyl having 1 to 4 carbon atoms which may optionally be substituted. Examples of the alkyl group are methyl, ethyl, n-propyl, n-butyl, isopropyl, cyclopropyl and tert-butyl. Examples of the alkenyl are vinyl, 2-propenyl, isopropenyl and 2-butenyl. Preferably, the aliphatic hydrocarbon group is exemplified by methyl, ethyl, n-propyl and isopropyl, more preferably methyl. The aliphatic hydrocarbon group may be unsubstituted or substituted. When the aliphatic group is substituted, for example, 1 to 6, preferably 1 to 3 substituents may be present. Examples of the substituents are a halogen, hydroxy, thiol, carboxy, methoxycarbonyl, acetoxy, acetylthio, cyano and acetylamino. Examples of the halogen are bromine, chlorine and fluorine. Preferably, the aliphatic hydrocarbon group is unsubstituted.

The unsubstituted or substituted aromatic hydrocarbon ring, aromatic heterocyclic ring or saturated heterocyclic ring shown by $A_D$ in the compounds of general formula [1D] is exemplified by a benzene, 1-naphthalene, 2-naphthalene, thiophene, furan, pyrrole, imidazole, oxazole, pyrazole, isoxazole, pyridine, pyrazine, indane, quinoline, isoquinoline, quinazoline, coumarine, pyrrolidine, piperidine or piperazine ring, preferably a benzene ring and a monocyclic aromatic heterocyclic ring, more preferably a benzene ring. These rings may be unsubstituted or substituted. When substituted, 1 to 6, preferably 1 to 3 substituents may be present on each ring. Examples of the substituents include an alkyl having 1 to 4 carbon atoms, a halogen, hydroxy, an alkyloxy having 1 to 4 carbon atoms, amino, a monoalkylamino or dialkylamino having 1 to 4 carbon atoms, thiol, carboxy, an alkyloxycarbonyl having 1 to 4 carbon atoms, an acyloxy having 1 to 5 carbon atoms, an acylthio having 1 to 5 carbon atoms, an acylamino having 1 to 5 carbon atoms, cyano and trifluoromethyl. Examples of the halogen are bromine, chlorine and fluorine. Examples of the alkyl having 1 to 4 carbon atoms and the alkyl moiety in the acyl having 1 to 5 carbon atoms are the same as those given for A. Preferred examples of $A_D$ are those unsubstituted, or those substituted with methyl, methoxy, methoxycarbonyl, nitro, cyano, a halogen or trifluoromethyl, for 1 to 3 hydrogen atoms.

In the ketone derivatives of general formula [1D], examples of the unsubstituted or substituted aliphatic group $B_D$ having 1 to 4 carbon atoms are the same as those given for $A_D$, preferably hydrogen or methyl.

In the ketone derivatives of general formula [1D], $A_D$ and $B_D$ are combined together to form an unsubstituted or substituted cycloalkan-1-one ring having 3 to 7 carbon atoms (provided that a ring of 5 carbon atoms is excluded) and examples of such a ring include a cyclopropanone, cyclobutanone, cyclohexanone and cycloheptanone ring, preferably a cyclobutanone and cyclohexanone ring. The cycloalkan-1-one ring may be nsubstituted or substituted, except for the substitution in general formula [1D]. When the ring is substituted, 1 to 4, preferably 1 to 2 substituents may be present on each ring. Examples of the substituents include a halogen, hydroxy, thiol, carboxy, methoxycarbonyl, hydroxymethyl, acetoxymethyl, cyano and acetylamino. Examples of the halogen are the same as those given for $A_D$. Preferably, the ring is unsubstituted.

In the ketone derivatives of the present invention represented by formula [1D], $X_D$ is preferably S, O or SO, most preferably S.

In $Y_D$ in the ketone derivatives represented by general formula [1D], the straight or branched aliphatic hydrocarbon group having 1 to 6 carbon atoms includes an alkyl or an alkenyl. Examples of the alkyl are methyl, ethyl, n-propyl, n-butyl, n-pentyl, n-hexyl, isopropyl and tert-butyl. Examples of the alkenyl are vinyl, 2-propenyl, isopropenyl and 2-butenyl. Preferably the aliphatic group is an alkyl having 1 to 4 carbon atoms, more preferably ethyl. The aliphatic hydrocarbon group may be unsubstituted or substituted. Where the aliphatic hydrocarbon group is substituted, the group may contain, e.g., 1 to 6, preferably 1 to 4 substituents. As such substituents, there are carboxy or a group derived therefrom, amino or a group derived therefrom and, hydroxy or a group derived therefrom. The aromatic hydrocarbon ring or monocyclic aromatic heterocyclic ring having 3 to 6 carbon atoms refers to an aromatic hydrocarbon ring such as a benzene ring and a aromatic heterocyclic ring such as a 5- or 6-membered ring containing nitrogen, oxygen or sulfur. Where the aromatic hydrocarbon ring or aromatic heterocyclic ring is substituted, examples of such substituents are the same as those given for the aliphatic hydrocarbon group.

The group derived from carboxy includes a functional group of carboxy, such as an esterified or amidated carboxy group, cyano, hydroxymethyl or aminomethyl formed by reducing these functional groups, and functional groups derived therefrom by modification like acylation or alkylation of the functional groups. Preferably, the carboxy and the group derived therefrom include carboxy, COOR1 (wherein R1 is an unsubstituted or substituted alkyl or alkenyl having 1 to 4 carbon atoms), CONR2R3 (wherein each of R2 and R3, which may be different or the same, independently represents hydrogen or a substituted or unsubstituted alkyl having 1 to 4 carbon atoms) and COW (W is an unsubstituted or substituted heterocyclic ring). Herein, the alkyl shown by R1 in COOR1 may be straight, branched or cyclic. Examples of the alkyl moiety are methyl, ethyl, n-propyl, isopropyl, cyclopropyl, n-butyl, isobutyl, tert-butyl and cyclobutyl, preferably methyl, ethyl, and n-propyl, more preferably methyl. Examples of the alkenyl are vinyl, 2-propenyl, isopropenyl and 2-butenyl. Where the alkyl or alkenyl is substituted, e.g., 1 to 6, preferably 1 to 3 substituents may be present. Examples of the substituents are a halogen, hydroxy, thiol, carboxy, methoxycarbonyl, acetyloxy, acetylthio, cyano and acetylamino. Examples of the halogen are the same as defined for A. Preferably, the alkyl for R1 is unsubstituted.

Where the alkyl shown by R2 or R3 and its substituent(s) are substituted, examples of such substituents are the same as those defined for R1.

Preferably W represents a saturated heterocyclic ring, more preferably, an azetidine, piperidine, pyrrolidine, piperazine or morpholine ring. These heterocyclic rings may be coupled to carbonyl via carbon or nitrogen, preferably to carbonyl via nitrogen. Where the heterocyclic ring is substituted, 1 to 4, preferably 1 to 2 substituents may be present on each ring. Examples of the substituents are carboxy or a group derived therefrom and amino or a group derived therefrom. Examples of these substituents are as defined in the specification.

Examples of the group derived from amino include such functional groups that amino is alkylated, acylated, or sulfoylated nitro, hydroxyamino, imino and a heterocyclic group containing the nitrogen atom from the amino, preferably a group shown by NR4R5 (wherein each of R4 and R5, which may be different or the same, independently represents hydrogen, an unsubstituted or substituted alkyl having 1 to 4 carbon atoms or an unsubstituted or substituted acyl having 1 to 5 carbon atoms). In the group shown by NR4R5, the alkyl moiety for R4 and R5 and the substituents where the alkyl is substituted are the same as those defined for R1. The acyl for R4 and R5 may be straight, branched, cyclic, saturated or unsaturated. Representative examples of the acyl are acetyl, propionyl, acroyl, propioloyl, n-butyryl, isobutyryl, crotonoyl, valeryl, isovaleryl and pivaloyl. Where the acyl is substituted, examples of the substituents are the same as those defined for R1. Preferably, the amino-derived group is NHCOR14 (wherein R14 is an alkyl having 1 to 4 carbon atoms in which hydrogen(s) may be substituted with fluorine(s); examples of the alkyl are the same as those given for R1). The number of fluorine atoms which may be substituted is 1 to 9, preferably 1 to 7. Most preferably, R14 is methyl.

Examples of the group derived from hydroxy include a functional group in which hydroxy is alkylated or acylated, a keto and a halogen, preferably OCOR15 (wherein R15 is an alkyl having 1 to 4 carbon atoms and examples of the alkyl are the same as those defined for R1).

$Z_D$ in the ketone derivatives [1D] of the present invention represents carboxy or a group derived therefrom, an unsubstituted or substituted alkyl or alkenyl having 1 to 4 carbon atoms, hydroxy or a group derived therefrom, amino or a group derived therefrom, sulfate or a group derived therefrom, phosphate or a group derived therefrom, a monocyclic aromatic heterocyclic ring, a halogen or hydrogen. Examples of the group derived from carboxy, amino or hydroxy are the same as defined above. Examples of the group derived from amino further include $NHSO_2Ph$, $NHCOCF_3$, $NHCOC_2F_5$, $NHSO_2CF_3$ and $NHSO_2C_2F_5$. Examples of the alkyl and alkenyl, and the substituents where the alkyl or alkenyl is substituted are the same as those defined for $A_D$. Examples of the group derived from sulfate are groups from sulfonamide derivatives, e.g., $SO_2NH_2$, $SO_2NHCH_3$, $SO_2N(CH_3)_2$ and $SO_2NHCOCH_3$. Examples of the group derived from phosphate are $P(O)(OH)H$, $P(O)(OH)(NH_2)$ and $P(O)(OH)CH(OCH_3)_2$. Preferred examples of $Z_D$ include carboxy, COOR7 (wherein R7 is an unsubstituted or substituted alkyl having 1 to 4 carbon atoms), CONR8R9 (wherein each of R8 and R9, which may be different or the same, independently represents hydrogen or a substituted or unsubstituted alkyl having 1 to 4 carbon atoms), cyano, hydroxy, $CH_2OR10$ (wherein R10 is hydrogen, an unsubstituted or substituted alkyl having 1 to 4 carbon atoms or an unsubstituted or substituted acyl having 1 to 5 carbon atoms), OCOR11 (wherein R11 is an unsubstituted or substituted alkyl having 1 to 4 carbon atoms), NR12R13 (wherein each of R12 and R13, which may be the same or different, independently represents hydrogen, an unsubstituted or substituted alkyl having 1 to 4 carbon atoms or an unsubstituted or substituted acyl having 1 to 5 carbon atoms), 5-tetrazolyl, a halogen or hydrogen. Examples of the alkyl moiety shown by R7, R8, R9, R10, R11, R12 and R13 and the substituents when the alkyl moiety is substituted are the same as those defined for R1. Examples of the acyl shown by R10, R12 and R13 and the substituents when the acyl is substituted are the same as those defined for R4. A preferred combination of R12 and R13 is that R12 is hydrogen and R13 is acetyl. Examples of the halogen are fluorine, chlorine, bromine and iodine, preferably fluorine and chlorine. More preferred examples of $Z_D$ are carboxy, COOR7' (wherein R7' is an alkyl having 1 to 4 carbon atoms) and $CH_2OR10'$ (wherein R10' is hydrogen, an unsubstituted or substituted acyl having 1 to 5 carbon atoms). Examples of R7' are the same as those given for R1. Examples of the acyl moiety in R10' are the same as those given for R4, most preferably, carboxy, methoxycarbonyl, hydroxymethyl and acetyloxymethyl.

[E] Compound of formula [1E]

The compound of formula [1E] is represented by formula [1E] above.

[F] Compounds of formula [1F]

In the compounds of the present invention represented by general formula [1F], the unsubstituted or substituted aliphatic hydrocarbon group having 1 to 4 carbon atoms, which is shown by $A_F$, refers to an alkyl or alkenyl having 1 to 4 carbon atoms which may optionally be substituted. Examples of the alkyl group are methyl, ethyl, n-propyl, isopropyl, n-butyl, isobutyl and tert-butyl. Examples of the alkenyl are vinyl, 2-propenyl, isopropenyl and 2-butenyl. Preferably, the aliphatic hydrocarbon group is exemplified by methyl, ethyl, n-propyl and isopropyl, more preferably methyl. The aliphatic hydrocarbon group may be unsubstituted or substituted. Where the aliphatic hydrocarbon group is substituted, e.g., 1 to 6, preferably 1 to 3 substituents may be present. Examples of the substituents are an alkyl having 1 to 4 carbon atoms, a halogen, hydroxy, an alkyloxy having 1 to 4 carbon atoms, amino, a monoalkylamino or dialkylamino having 1 to 4 carbon atoms, nitro, cyano, trifluoromethyl, carboxy, an alkyloxycarbonyl having 1 to 4 carbon atoms, an acyloxy having 1 to 5 carbon atoms, an acylthio having 1 to 5 carbon atoms and an acylamino having 1 to 5 carbon atoms. Examples of the halogen are bromine, chlorine and fluorine. Examples of the alkyl having 1 to 4 carbon atoms and the alkyl moiety with 1 to 4 carbon atoms in the acyl having 1 to 5 carbon atoms are the same as those defined for $A_F$.

The unsubstituted or substituted aromatic hydrocarbon ring, aromatic heterocyclic ring or saturated heterocyclic ring group shown by $A_F$ in the compounds of general formula [1F] includes a benzene, 1-naphthalene, 2-naphthalene, thiophene, furan, pyrrole, imidazole, oxazole, pyrazole, isoxazole, pyridine, pyrazine, indane, quinoline, isoquinoline, quinazoline, coumarine, pyrrolidine, piperidine or piperazine ring, preferably a benzene ring and a monocyclic aromatic heterocyclic ring, more preferably a benzene ring. These rings may be unsubstituted or substituted. Where the ring is substituted, e.g., 1 to 6, preferably 1 to 3 substituents may be present on each ring. Examples of the substituents include an alkyl having 1 to 4 carbon atoms, a halogen, hydroxy, an alkyloxy having 1 to 4 carbon atoms, amino, a monoalkylamino or dialkylamino having 1 to 4 carbon atoms, thiol, carboxy, an alkyloxycarbonyl having 1 to 4 carbon atoms, an acyloxy having 1 to 5 carbon atoms, an acylthio having 1 to 5 carbon atoms, an acylamino having 1 to 5 carbon atoms, cyano and trifluoromethyl. Examples of the halogen are bromine, chlorine and fluorine. Examples of the alkyl having 1 to 4 carbon atoms and the alkyl moiety in the acyl having 1 to 5 carbon atoms are the same as those given for A. Preferred examples Of $A_F$ are those unsubstituted, or those substituted with methyl, methoxy, methoxycarbonyl, nitro, cyano, a halogen or trifluoromethyl, for 1 to 3 hydrogen atoms.

In the compounds of general formula [1F], examples of the unsubstituted or substituted aliphatic hydrocarbon group $B_F$ having 1 to 4 carbon atoms are the same as those given for $A_F$.

In the compounds of general formula [1F], $A_F$ and $B_F$ are combined together to form an unsubstituted or substituted cycloalkan-1-one ring having 3 to 7 carbon atoms. Examples of the ring include a cyclopropan-1-one, cyclobutan-1-one, cyclopentan-1-one, cyclohexan-1-one and cycloheptan-1-one ring, preferably a cyclobutan-1-one, cyclopentan-1-one and cyclohexan-1-one ring, more preferably cyclopentan-1-one. These rings may be unsubstituted or substituted. Where the ring is substituted, e.g., 1 to 2 substituents may be present on each ring. Examples of the substituents include a halogen, hydroxy, carboxy, methoxycarbonyl, acetoxy, acetylthio, cyano and acetylamino. Examples of the halogen are bromine, chlorine and fluorine. As an example that there are the two substituents, a fused ring with an aromatic hydrocarbon ring or aromatic heterocyclic ring is representative. Examples of the aromatic hydrocarbon ring formed by $A_F$ and $B_F$ are a benzene ring and a naphthalene ring. Examples of the aromatic heterocyclic ring are a 6-membered aromatic heterocyclic ring such as a pyridine, pyrazine or pyrimidine ring, and a 5-membered heteroaryl such as a thiophene, pyrrole, furan, oxazole, thiazole, isoxazole, isothiazole or azole ring. Preferably, the group formed by $A_F$ and $B_F$ is an aromatic hydrocarbon ring, more preferably a benzene ring. Where the ring is substituted, examples of the substituents are an alkyl having 1 to 4 carbon atoms, e.g., an unsubstituted alkyl such as ethyl, n-propyl and isopropyl, or an alkyl substituted with a halogen (e.g., fluorine) such as trifluoromethyl; an alkyloxy having 1 to 4 carbon atoms such as methoxy and ethoxy; nitro, and a halogen, e.g., fluorine, chlorine or bromine. Specific examples are indan-1-one, 6,7-dihydro-5-oxocyclopenta[b]pyridine and 5,6-dihydro-7-oxocyclopenta[b]pyridine, preferably indan-1-one.

In the compounds of the present invention represented by general formula [1F], the straight or branched aliphatic hydrocarbon group having 1 to 10 carbon atoms, which is shown by $X_F$ or $Y_F$, refers to an alkyl or alkenyl having 1 to 10 carbon atoms. Preferably, the aliphatic hydrocarbon group is an alkyl having 1 to 6 carbon atoms and examples of the alkyl group are ethyl, n-propyl, n-butyl, n-pentyl, n-hexyl, isopropyl and isobutyl, more preferably ethyl, n-propyl and isopropyl, most preferably ethyl. The aliphatic group may be unsubstituted or substituted. Where the aliphatic group is substituted, the aliphatic group may contain, e.g., 1 to 6, preferably 1 to 3 substituents. Examples of the substituents are carboxy or a group derived therefrom, amino or a group derived therefrom and, hydroxy or a group derived therefrom.

The group derived from carboxy includes a functional group of carboxy, such as an esterified or amidated carboxy group (e.g., —COOR1, —COOR1', —COOR1", —CONR2R3, —CONR2'R3', —CONR2"R3", etc. described below), cyano, hydroxymethyl or aminomethyl formed by reducing these functional groups, and functional groups derived therefrom by modification like acylation of the functional groups (e.g., —CH$_2$OR4, —CH$_2$OR4' described below).

Examples of the group derived from amino include such functional groups that amino is alkylated acylated or sulfonylated (e.g., —NR6R7 described above), nitro, hydroxyamino, imino and a heterocyclic group containing the nitrogen atom from the amino.

Examples of the group derived from hydroxy include a functional group in which hydroxy is alkylated or acylated (e.g., —OR5 described above), a keto and a halogen.

In the compounds of the present invention represented by general formula [1F], examples of the heterocyclic group formed by linking $X_F$ and $Y_F$ to each other directly or via a hetero atom are pyrrole, imidazole, indole, indazole, purine, carbazole, imidazolidine, imidazoline, pyrrolidine, piperidine, piperazine, morpholine and indoline ring. Preferably, the heterocyclic group is a monocyclic heterocyclic ring such as a pyrrole, imidazole, imidazolidine, imidazoline, pyrrolidine, piperidine, piperazine and morpholine ring, more preferably a saturated monocyclic heterocyclic ring such as a pyrrolidine, piperidine and morpholine ring. These rings may be unsubstituted or substituted. Where the ring is substituted, e.g., 1 to 6, preferably 1 to 3 substituents may be present on each ring. Examples of the substituents include an alkyl having 1 to 4 carbon atoms, phenyl, carboxy or a group derived therefrom, amino or a group derived therefrom and, hydroxy or a group derived therefrom. Examples of the group derived from carboxy, amino or hydroxy are described above. Preferred examples of the substituents are an alkyl having 1 to 4 carbon atoms and phenyl, more preferably methyl and phenyl. Preferred examples of the substituted heteroaryl are imidazolidine and piperazine rings, more preferably a 4-methylpiperazine and 4-phenylpiperazine ring.

In the compounds of the present invention represented by general formula [1F], $Z_F$ is carboxy or a group derived therefrom, an unsubstituted or substituted alkyl or alkenyl having 1 to 4 carbon atoms, hydroxy or a group derived therefrom, amino or a group derived therefrom, sulfate or a group derived therefrom, phosphate or a group derived therefrom, a monocyclic heteroaryl or a halogen. Examples of the group derived from carboxy, amino or hydroxy are described above. Examples of the group derived from amino further include $NHSO_2Ph$, $NHCOCF_3$, $NHCOC_2F_5$, $NHSO_2CF_3$ and $NHSO_2C_2F_5$. Examples of the group derived from sulfate are groups from sulfonamide derivatives, e.g., $SO_2NH_2$, $SO_2NHCH_3$, $SO_2N(CH_3)_2$ and $SO_2NHCOCH_3$. Examples of the group derived from phosphate are $P(O)(OH)H$, $P(O)(OH)(NH_2)$ and $P(O)(OH)CH(OCH_3)_2$. Examples of the alkyl group having 1 to 4 carbon atoms are methyl, ethyl, n-propyl, isopropyl and n-butyl. Examples of the alkenyl having 1 to 4 carbon atoms are vinyl, 2-propenyl, isopropenyl and 2-butenyl. Where the alkyl or alkenyl is substituted, examples of such substituents are the same as those defined for the aliphatic group in $A_F$. Examples of the monocyclic heteroaryl include 5-tetrazolyl, 3-(4H-5-oxo-1,2,4-oxadiazolyl), 5-(3-hydroxyisoxazolyl), 5-(3-hydroxyisothiazolyl) and 4-(3-hydroxy-1,2,5-thiadiazolyl). Examples of the halogen are fluorine, chlorine, bromine and iodine. More preferred examples of $Z_F$ are carboxy, COOR1 (wherein R1 is an unsubstituted or substituted alkyl having 1 to 4 carbon atoms or phenyl), CONR2R3 (wherein each of R2 and R3, which may be different or the same, independently represents hydrogen or a substituted or unsubstituted alkyl having 1 to 4 carbon atoms), cyano, $CH_2OR4$ (wherein R4 is hydrogen, an unsubstituted or substituted alkyl having 1 to 4 carbon atoms or an acyl having 1 to 5 carbon atoms), —OR5 (wherein R5 is an unsubstituted or substituted alkyl having 1 to 4 carbon atoms or an unsubstituted or substituted an acyl having 1 to 5 carbon atoms), 5-tetrazolyl, chlorine and fluorine. Examples of the substituents for the alkyl or acyl are the same as those defined for the substituents of the aliphatic group shown by $A_F$. More preferred examples of $A_F$ are carboxy, COOR1' (wherein R1' is an alkyl having 1 to 4 carbon atoms), CONR2'R3' (wherein each of R2' and R3', which may be different or the same, independently represents hydrogen or an alkyl having 1 to 4 carbon atoms), cyano and $CH_2OR4'$ (wherein R4' is hydrogen, an alkyl having 1 to 4 carbon atoms or an acyl having 1 to 5 carbon atoms). $Z_F$ as particularly preferred examples includes carboxy, COOR1" (wherein R1" is methyl or ethyl), CONR2"R3" (wherein each of R2" and R3", which may be different or the same, independently represents hydrogen, methyl or ethyl) and cyano.

Representative examples of the compounds in accordance with the present invention are listed below.

Compounds of formula [1A]

(1A) trans-4-{(2R)-2-acetylamino-2-carboxyethylthio}methyl-3-oxo-1-cyclopentanecarboxylic acid;

(2A) trans-4-{(2R)-2-acetylamino-2-methoxycarbonylethylthio}methyl-3-oxo-1-cyclopentanecarboxylic acid;

(3A) 2RS,4S)-2-{(2R)-2-acetylamino-2-carboxyethylthio}methyl-4-hydroxy-1-cyclopentanone;

(4A) 2RS,4S)-2-[(2R)-3-acetylamino-3-{1-{(2S)-2-methoxycarbonyl}pyrrolidinyl]-3-oxypropylthio}methyl-4-hydroxy-1-cyclopentanone;

(5A) 2-{(2R)-2-acetylamino-2-carboxyethylthio}methyl-3-oxo-1-indanecarboxylic acid;

(6A) 2-{(2R)-2-acetylamino-2-methoxycarbonylethylthio}methyl-3-oxo-1-indanecarboxylic acid Compounds of formula [1B]

(1B) (1R,2S)-2-[(2R)-{2-acetylamino-3-oxo-3-(1-pyrrolidinyl)}propylthio]methyl-3-oxo-1-cyclopentanecarboxylic acid;

(2B) (1R,2S)-2-[(2R)-{2-acetylamino-3-(4-morpholinyl)-3-oxo}propylthio]methyl-3-oxo-1-cyclopentanecarboxylic acid;

(3B) (1R,2S)-2-[(2R)-{2-acetylamino-3-oxo-3-(1-piperidinyl)propylthio}]methyl-3-oxo-1-cyclopentanecarboxylic acid;

(4B) (1R,2S)-2-[(2R)-({2-carboxy-2-pentafluoropropionylamino)ethylthio]methyl-3-oxo-1-cyclopentanecarboxylic acid;

(5B) trans-2-[(2R)-{2-acetylamino-3-oxo-3-(1-pyrrolidinyl)}propylthio]methyl-3-methoxycarbonyl-1-cyclopentanone;

(6B) trans-2-[(2R)-[2-acetylamino-3-{1-((2S)-2-methoxycarbonylpyrrolidinyl)}-3-oxo]propylthio]methyl-3-oxo-1-cyclopentanecarboxylic acid;

(7B) trans-2-[(2R)-[2-acetylamino-3-{1-((2S)-2-methoxycarbonylazetidinyl)}-3-oxo]propylthio]methyl-3-oxo-1-cyclopentanecarboxylic acid;

(8B) trans-2-[(2R)-(2-carboxy-2-pentafluoropropionylamino)ethylthio]methyl-3-hydroxymethyl-1-cyclopentanone;

(9B) trans-2-[(11-acetylamino- 11-carboxy)undecylthio]methyl-3-oxo-1-cyclopentanecarboxylic acid;

(10B) (1R,2S)-2-[(2R)-{2-acetylamino-3-oxo-3-(1-piperazinyl)propylthio}]methyl-3-oxo-1-cyclopentanecarboxylic acid;

(11B) (1R,2S)-2-[(2R)-{2-acetylamino-3-oxo-3-(1-(4-hydroxymethyl)piperazinyl)propylthio}]methyl-3-oxo-1-cyclopentanecarboxylic acid;

(12B) (1R,2S)-2-[(2R)-{2-acetylamino-3-oxo-3-(1-(4-tert-butoxycarbonyl)piperazinyl)propylthio}]methyl-3-oxo-1-cyclopentanecarboxylic acid;

(13B) (1R,2S)-2-[(2R)-[2-acetylamino-3-oxo-3-{1-(4-phenyl)piperazinyl}propylthio]methyl-3-oxo-1-cyclopentanecarboxylic acid;

(14B) (1R,2S)-2-{3-(3-pyridyl)propylthio}methyl-3-oxo-1-cyclopentanecarboxylic acid;

(15B) (1R,2S)-2-[3-{3-(1-methylpyridinium iodide)}propylthio]methyl-3-oxo-1-cyclopentanecarboxylic acid;

(16B) (1R,2S)-2-[2-acetylamino-2-(5-tetrazolyl)ethylthio]]methyl-3-oxo-1-cyclopentanecarboxylic acid Compounds of formula [1C]

(1C) 5-[(2R)-(2-acetylamino-2-carboxy)ethylthio]methyl-2-cyclopenten-1-one;

(2C) (4R)-2-[(2R)-(2-acetylamino-2-carboxy)ethylthio]methyl-4-hydroxy-2-cyclopenten-1-one;

(3C) 2-[(2R)-(2-acetylamino-2-carboxy)ethylthio]methyl-3-hydroxy-2-cyclopenten-1-one;

(4C) 5-[(2R)-(2-acetylamino-2-carboxy)ethylthio]methyl-4-carboxy-2-cyclopenten-1-one;

(5C) 5-[(2R)-(2-acetylamino-2-carboxy)ethylthio]methyl-4-methoxycarbonyl-2-cyclopenten-1-one;

(6C) 5-[(2R)-(2-acetylamino-2-carboxy)ethylthio]methyl-4-hydroxymethyl-2-cyclopenten-1-one;

(7C) 5-[(2R)-(2-acetylamino-2-carboxy)ethylthio]methyl-4-acetoxymethyl-2-cyclopenten-1-one;
(8C) 5-[(2R)-(2-acetylamino-2-methoxycarbonyl)ethylthio]methyl-4-carboxy-2-cyclopenten-1-one;
(9C) 5-[(2-acetylamino)ethylthio]methyl-4-carboxy-2-cyclopenten-1-one;
(10C) 2-[(2R)-(2-acetylamino-2-carboxy)ethylthio]methyl-3-carboxy-2-cyclopenten-1-one;
(11C) 2-[(2R)-(2-acetylamino-2-carboxy)ethylthio]methyl-3-methoxycarbonyl-2-cyclopenten-1-one;
(12C) 2-[(2R)-(2-acetylamino-2-carboxy)ethylthio]methyl-3-hydroxymethyl-2-cyclopenten-1-one;
(13C) 2-[(2R)-(2-acetylamino-2-carboxy)ethylthio]methyl-3-acetoxymethyl-2-cyclopenten-1-one;
(14C) 2-[(2R)-(2-acetylamino-2-methoxycarbonyl)ethylthio]methyl-3-carboxy-2-cyclopenten-1-one;
(15C) 2-[(2-methoxycarbonyl)ethylthio]methyl-3-carboxy-2-cyclopenten-1-one;
(16C) 2-[(2-acetylamino)ethylthio]methyl-3-carboxy-2-cyclopenten-1-one Compounds of formula [1D]
(1D) 3-{(2R)-2-acetylamino-2-carboxyethylthio}methyl-4-oxo-1-n-pentanoic acid;
(2D) 3-{(2R)-2-acetylamino-2-methoxycarbonylethylthio}methyl-4-oxo-1-n-pentanoic acid;
(3D) trans-2-{(2R)-2-acetylamino-2-methoxycarbonylethylthio}methyl-3-ethoxycarbonyl-1-cyclobutanone;
(4D) trans-2-{(2R)-2-acetylamino-2-carboxyethylthio}methyl-3-oxo-1-cyclobutanecarboxylic acid;
(5D) 2-(2,3-dihydroxy-n-propyl)thiomethyl-3-acetoxymethyl-1-cyclobutanone;
(6D) 2-{(2R)-2-acetylamino-2-carboxyethylthio}methyl-3-oxo-1-cyclohexanecarboxylic acid;
(7D) 3-[(2R)-(2-acetylamino-2-carboxy)ethylthio]methyl-4-oxo-4-phenylbutyric acid;
(8D) 3-[(2R)-(2-acetylamino-2-methoxycarbonyl)ethylthio]methyl-4-oxo-4-phenylbutyric acid;
(9D) 3-[(2R)-(2-acetylamino-2-methoxycarbonyl)ethylthio]methyl-4-(4-methoxyphenyl)-4-oxobutyric acid;
(10D) 3-{2-(acetylamino)ethylthio}methyl-4-(4-methoxyphenyl)-4-oxobutyric acid;
(11D) 3-{2-(acetylamino)ethylthio}methyl-4-oxo-4-phenylbutyric acid;
(12D) 3-{2-(acetylamino)ethylthio}methyl-4-(4-methylphenyl)-3-oxobutyric acid;
(13D) 3-{(2R)-(2-acetylamino-2-methoxycarbonyl)ethylthio}methyl-4-(4-methylphenyl)-3-oxobutyric acid;
(14D) 3-[(2R)-(2-acetylamino-2-carboxy)ethylthio]methyl-4-oxo-4-(4-trifluoromethylphenyl)butyric acid;
(15D) 3-[(2R)-(2-acetylamino-2-carboxy)ethylthio]methyl-4-oxo-4-(2-trifluoromethylphenyl)butyric acid;
(16D) 3-[(2R)-(2-acetylamino-2-carboxy)ethylthio]methyl-4-oxo-4-(3-trifluoromethylphenyl)butyric acid;
(17D) 3-[(2R)-(2-acetylamino-2-carboxy)ethylthio]methyl-4-oxo-4-(3-pyridyl)butyric acid;
(18D) 3-[(2R)-(2-acetylamino-2-carboxy)ethylthio]methyl-4-oxo-4-(2-pyridyl)butyric acid;
(19D) 3-[(2R)-(2-acetylamino-2-carboxy)ethylthio]methyl-4-oxo-4-(4-pyridyl)butyric acid;
(20D) 3-[(2R)-(2-acetylamino-2-carboxy)ethylthio]methyl-4-(1-naphthyl)-4-oxobutyric acid;
(21D) 3-[(2R)-(2-acetylamino-2-carboxy)ethylthio]methyl-4-(2-naphthyl)-4-oxobutyric acid;
(22D) 3-[(2R)-(2-acetylamino-2-carboxy)ethylthio]methyl-4-oxo-4-(1-piperidyl)butyric acid;
(23D) 3-[(2R)-(2-acetylamino-2-carboxy)ethylthio]methyl-4-(4-methyl-1-piperazinyl)-4-oxobutyric acid;
(24D) 3-[(2R)-(2-acetylamino-2-carboxy)ethylthio]methyl-4-oxo-4-(4-phenyl-1-piperazinyl)butyric acid;
(25D) 3-[(2R)-(2-acetylamino-2-carboxy)ethylthio]methyl-4-(2-furyl)-4-oxobutyric acid;
(26D) 3-[(2R)-(2-acetylamino-2-carboxy)ethylthio]methyl-4-(3-furyl)-4-oxobutyric acid;
(27D) 3-[(2R)-(2-acetylamino-2-carboxy)ethylthio]methyl-4-oxo-4-(2-thienyl)butyric acid;
(28D) 3-[(2R)-(2-acetylamino-2-carboxy)ethylthio]methyl-4-oxo-4-(3-thienyl)butyric acid;
(29D) 3-[(2R)-(2-acetylamino-2-carboxy)ethylthio]methyl-4-oxo-4-(2-pyrrolyl)butyric acid;
(30D) 3-[(2R)-(2-acetylamino-2-carboxy)ethylthio]methyl-4-oxo-4-(3-pyrrolyl)butyric acid;
(31D) 3-[(2R)-(2-acetylamino-2-carboxy)ethylthio]methyl-4-(2-imidazolyl)-4-oxobutyric acid;
(32D) 3-[(2R)-(2-acetylamino-2-methoxycarbonyl)ethylthio]methyl-4-oxo-4-(3-pyridyl)butyric acid;
(38D) 4-[(2R)-{(2-acetylamino-2-carboxy)ethylthio}]methyl-5-oxo-5-phenylpentanoic acid Compound of formula [1E]
(1E) (1R,2S)-2-[N-(panthoyl- -alanylamido)ethylthio]methyl-3-oxo-1-cyclopentanecarboxylic acid Compounds of formula [1F]
(1F) 4-oxo-4-phenyl-3-(1-piperidyl)methylbutyric acid;
(2F) 4-(4-methylphenyl)-4-oxo-3-(1-piperidyl)methylbutyric acid;
(3F) 4-(4-methoxyphenyl)-4-oxo-3-(1-piperidyl)methylbutyric acid;
(4F) 4-oxo-4-phenyl-3-(1-pyrrolidinyl)methylbutyric acid;
(5F) 3-(4-morpholinyl)methyl-4-oxo-4-phenylbutyric acid;
(6F) 3-{1-(4-methylpiperazinyl)}methyl-4-oxo-4-phenylbutyric acid;
(7F) 3-(diethylamino)methyl-4-oxo-4-phenylbutyric acid;
(8F) (1R,2R)-3-oxo-2-(1-piperidyl)methyl-1-cyclopentanecarboxylic acid;
(9F) 4-oxo-3-(1-piperidyl)methyl-4-(4-trifluoromethylphenyl) butyric acid;
(10F) 4-oxo-3-(1-piperidyl)methyl-4-(2-trifluoromethylphenyl) butyric acid;
(11F) 4-oxo-3-(1-piperidyl)methyl-4-(3-trifluoromethylphenyl)butyric acid;
(12F) 4-oxo-3-(1-piperidyl)methyl-4-(3-pyridyl)butyric acid;
(13F) 4-oxo-3-(1-piperidyl)methyl-4-(2-pyridyl)butyric acid;
(14F) 4-oxo-3-(1-piperidyl)methyl-4-(4-pyridyl)butyric acid;
(15F) 3-oxo-2-(1-piperidyl)methyl-1-indanecarboxylic acid;

(16F) 3-oxo-2-(1-pyrrolidinyl)methyl-1-indanecarboxylic acid;
(17F) 2-(4-morpholinyl)methyl-3-oxo-1-indanecarboxylic acid;
(18F) 2-{1-(4-methylpiperazinyl)}methyl-3-oxo-1-indanecarboxylic acid;
(19F) 3-{1-(4-phenylpiperazinyl)}methyl-4-oxo-4-phenylbutyric acid;
(20F) 4-oxo-4-(1-naphthyl)-3-(1-piperidyl)methylbutyric acid;
(21F) 4-oxo-4-(2-naphthyl)-3-(1-piperidyl)methylbutyric acid
(22F) 4-oxo-4-(1-piperidyl)-3-(1-piperidyl)methylbutyric acid;
(23F) 4-oxo-4-(4-methyl-1-piperazinyl)-3-(1-piperidyl)methylbutyric acid;
(24F) 4-oxo-4-(4-phenyl-1-piperazinyl)-3-(1-piperidyl)methylbutyric acid;
(25F) 4-oxo-4-(1-naphthyl)-3-(1-pyrrolidinyl)methylbutyric acid;
(26F) 4-oxo-4-(2-naphthyl)-3-(1-pyrrolidinyl)methylbutyric acid;
(26F) 4-(2-furyl)-4-oxo-3-(1-piperidyl)methylbutyric acid;
(27F) 4-(3-furyl)-4-oxo-3-(1-piperidyl)methylbutyric acid;
(28F) 4-oxo-3-(1-piperidyl)methyl-4-(2-thienyl)butyric acid;
(29F) 4-oxo-3-(1-piperidyl)methyl-4-(3-thienyl)butyric acid;
(30F) 4-oxo-3-(1-piperidyl)methyl-4-(2-pyrrolyl)butyric acid;
(31F) 4-oxo-3-(1-piperidyl)methyl-4-(3-pyrrolyl)butyric acid;
(32F) 4-(2-imidazolyl)-4-oxo-3-(1-piperidyl)methylbutyric acid;
(33F) 4-oxo-4-phenyl-3-(1-piperidyl)methylbutyronitrile;
(34F) methyl 4-oxo-4-phenyl-3-(1-piperidyl)methylbutyrate;
(35F) ethyl 4-oxo-4-phenyl-3-(1-piperidyl)methylbutyrate;
(36F) 4-(2-imidazolyl)-4-oxo-3-(1-pyrrolidinyl)methylbutyric acid;
(37F) 4-oxo-4-phenyl-3-(1-pyrrolidinyl)methylbutyronitrile;
(38F) 4-oxo-4-phenyl-3-(4-methyl-1-piperazinyl)methylbutyronitrile;
(39F) 4-oxo-4-phenyl-3-(4-morpholinyl)methylbutyronitrile;
(40F) 4-(2-imidazolyl)-4-oxo-3-(4-morpholinyl)methylbutyric acid;
(41F) 2-methyl-4-oxo-4-phenyl-3-(1-piperazinyl)methylbutyric acid;
(42F) 4-(1-piperazinyl)methyl-5-oxo-5-phenylpentanoic acid The compounds of the present invention may also be present in the form of stereoisomers such as geometrical isomers and mixtures thereof, diastereoisomers and mixtures thereof, optical isomers and racemic isomers. The compounds of the present invention cover all of these stereoisomers and mixtures thereof.

The compounds of the present invention may optionally be present in the form of pharmacologically acceptable salts thereof. Examples of such salts are salts with acids including inorganic salts such as hydrochlorides, sulfates, phosphates, and Group IIIA salts, e.g., aluminum salts, etc.; and organic salts such as p-toluenesulfonates. As salts with bases, there are salts with alkali metals such as sodium or potassium, salts with alkaline earth metals such as calcium, and organic salts with methylamine, ethylenediamine, etc. These pharmacologically acceptable salts of the compounds of the present invention may be prepared by known methods.

Hereinafter representative processes for preparing the compounds of the present invention are shown below but are not deemed to be limited to these processes only. The compounds of the present invention shown below and intermediates thereof may be isolated by conventional means of extraction, recrystallization, chromatography and the like.

[A] Processes for producing the compounds of formula [1A]

The compounds of general formula [1A] wherein $X_A$ is S, O, or NH are prepared by reacting cyclopentanone derivatives (the carbonyl at the 1-position thereof may be protected if necessary; hereinafter simply referred to as reactive derivatives) represented by general formula [2A]:

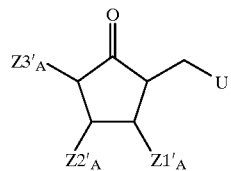

[2A]

(wherein U is a leaving group and, $Z1'_A$, $Z2'_A$ and $Z3'_A$ have the same significance as defined in $Z1_A$, $Z2_A$ and Z3A but when these groups contain a functional group(s), these groups may optionally be protected), with compounds of general formula [3A]:

$HX_A2-Y'_A$ [3A]

(wherein $X_A2$ is S, O or NH and $Y'_A$ has the same significance as defined for $Y_A$ but where it contains a functional group, the functional group may be protected, if desired), and when required, removing the protective group. Preferred examples of the reactive derivatives described above are compounds of general formulas [4A], [5A], [6A], [7A] and [8A].

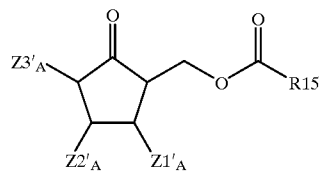

[4A]

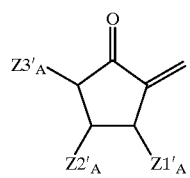

[5A]

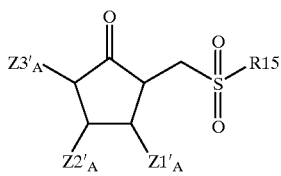

[6A]

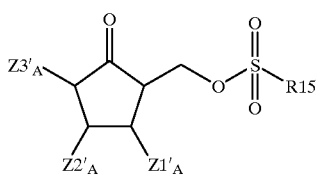

[7A]

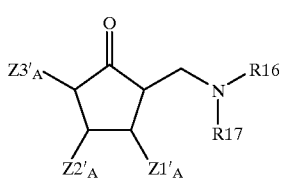

[8A]

In the formulas above, R15 is an hydrocarbon group having 1 to 10 carbon atoms, such as an alkyl, an alkenyl or an aryl. These groups may be substituted or unsubstituted. Where a substituent(s) are a functional group(s), the functional groups may be protected with protective groups, if necessary and desired. Each of R16 and R17, which may be the same or different, independently represents an alkyl having 1 to 4 carbon atoms, or R16 and R17 are combined together to form a piperazine or pyrrolidine ring. $Z1'_A$, $Z2'_A$ and $Z3'_A$ have the same significance as defined above.

Examples of the compounds of general formulas [4A], [5A], [6A] and [7A] are illustrated below.

(a) 4-[(2,3-O-isopropylidene)propylsulfonyl]methyl-3-oxo-1-cyclopentanecarboxylic acid
(b) 4-methylidene-3-oxo-1-cyclopentanecarboxylic acid
(c) (2RS,4S)-2-{(2R)-(2-acetylamino-2-methoxycarbonyl) ethylsulfonyl}methyl-4-hydroxycyclopentan-1-one In general formula [3A] wherein $X_A$ is S and $Y_A$ is an amino acid derivative residue, the compounds of formula [3A] include the following:

(d) (2R)-2-acetylamino-2-carboxyethanethiol
(e) (2R)-2-acetylamino-2-methoxycarbonylethanethiol For this reaction, any condensation process may be used so long as the compounds of formula [2A] can be condensed with the compounds of formula [3A]. The reaction is carried out generally in an organic solvent, water or a mixture thereof. As the organic solvent there may be employed an aromatic hydrocarbon such as benzene, toluene, etc.; an alcohol such as methanol, ethanol, etc.; an ether such as tetrahydrofuran, diethyl ether, etc.; a halogenated hydrocarbon such as methylene chloride, chloroform, etc.; a ketone such as acetone, methyl ethyl ketone, etc.; an aprotic polar solvent such as dimethyl sulfoxide, dimethylformamide, etc. Preferred examples of the solvent are an ether such as tetrahydrofuran or diethyl ether, a halogenated hydrocarbon such as methylene chloride or chloroform, a ketone such as acetone or methyl ethyl ketone, an aprotic polar solvent such as dimethyl sulfoxide or dimethylformamide, or a mixture of such solvent and water. The reaction proceeds generally in the presence of an acid or a base or in the absence or any catalyst, preferably under basic conditions using inorganic bases, e.g., potassium hydroxide, sodium hydroxide, potassium carbonate, sodium carbonate, sodium hydride, etc., or organic bases such as triethylamine, 1,8-diazabicyclo [5.4.0]-undeca-7-ene, etc. These reactants are employed in an amount of approximately 0.1 to 20-fold mols, preferably approximately 0.5 to 5-fold mols. The reaction temperature is not particularly limited so that the reaction may be carried out under cooling, at ambient temperature or with heating. Preferably, the reaction is performed at a temperature between 0° C. and 100° C. The compounds of formula [2A] may be reacted with the compounds of formula [3A] in an equimolar amount. Practically, the compounds of formula [3A] may be used in an excess amount, e.g., 1 to 2-fold mols. The reaction is performed in 0.1 to 200 hours, preferably 0.1 to 72 hours.

The compounds of formula [1A] wherein $X_A$ is $SO_2$ can be prepared by oxidizing the compounds of formula [1A] wherein $X_A$ is S, with an oxidizing agent. As the oxidizing agent, an organic peracid such as m-chloroperbenzoic acid, etc., an inorganic oxidizing agent such as permanganate, chromic acid, ruthenium tetroxide, etc., hydrogen peroxide, an organic peroxide, etc., preferably an organic peracid such as m-chloroperbenzoic acid.

The compounds of formula [1A] wherein $X_A$ is SO can be prepared by oxidizing the compounds of formula [1A] wherein $X_A$ is S, with an oxidizing agent. As the oxidizing agent, an organic peracid such as m-chloroperbenzoic acid, etc., an inorganic oxidizing agent such as manganese dioxide, chromic acid, ruthenium tetroxide, etc., hydrogen peroxide, an organic peroxide, a halogen type oxidizing agent such as periodic acid, etc.

For example, Compounds (a) and (b) described above are prepared by the following procedure.

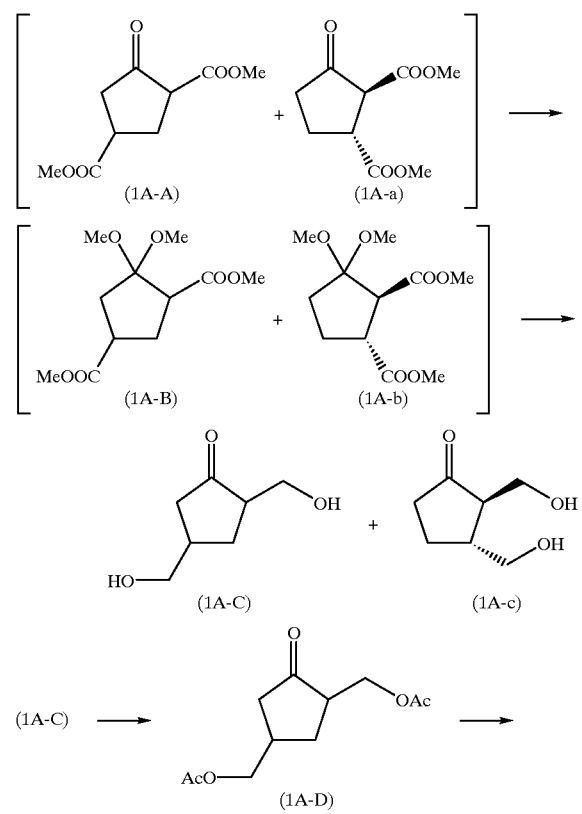

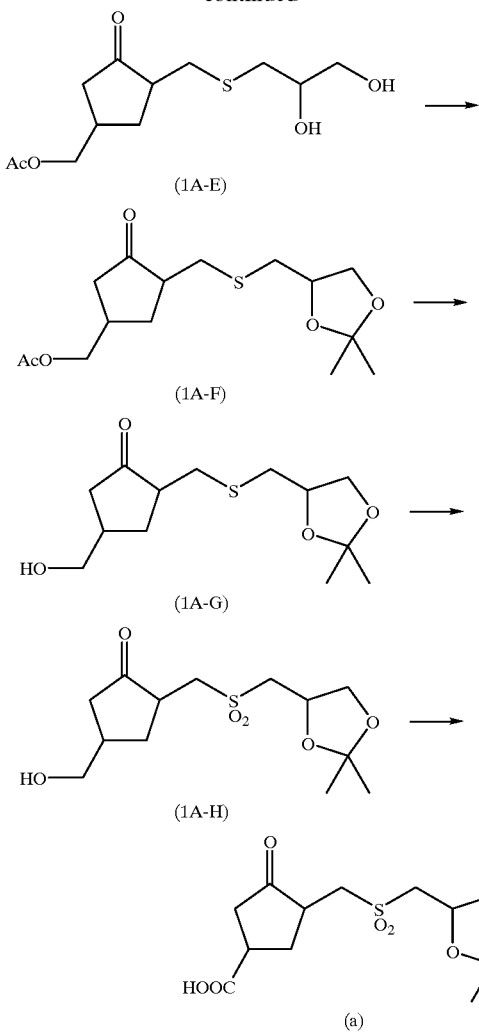

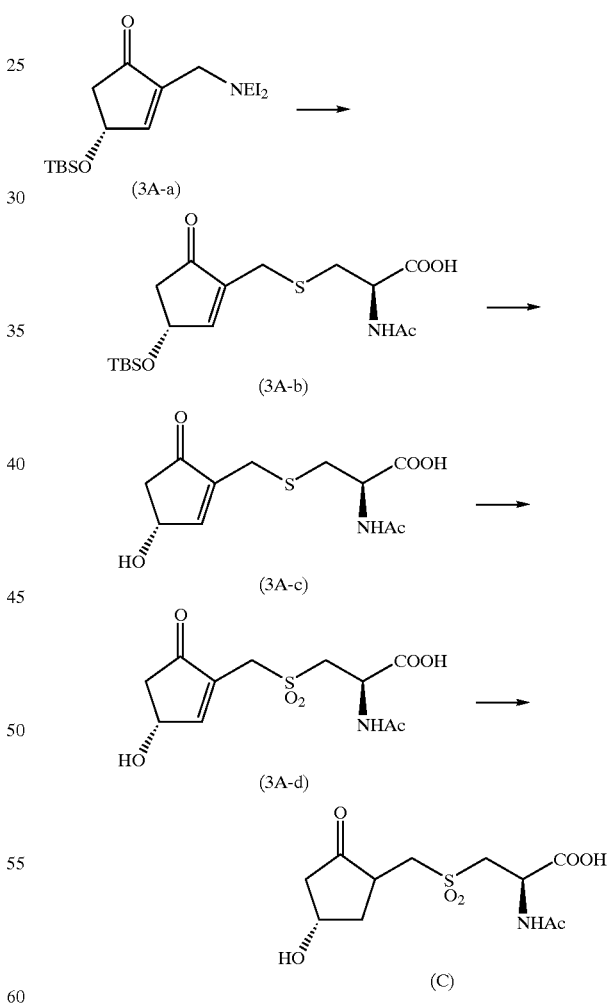

remove the acetyl and give Compound (1A-G). Next, Sulfide of Compound (1A-G) is oxidized form to sulfone. Thus, Compound (1A-H) is obtained. The reaction is carried out under conditions similar to those used for the foregoing oxidation wherein the conditions are set forth so as not to oxidize the hydroxy. In the case that the hydroxy is also oxidized, Compound (a) is obtained. Next, the hydroxy is oxidized to give Compound (a). Examples of the oxidizing agent that can be used are inorganic oxidizing agents such as permanganates and chromic acid, preferably chromic acid. Compound (b) may be prepared by maintaining Compound (a) under basic conditions similar to the conditions used for the condensation between the compounds of formula [2A] and the compounds of formula [3A]. In this reaction, there is no need to add the compounds of formula [3A]. Reactants used for the reaction are inorganic bases, e.g., potassium hydroxide, sodium hydroxide, potassium carbonate, sodium carbonate, etc., or organic bases such as triethylamine, 1,8-diazabicyclo[5.4.0]-undeca-7-ene, etc., preferably an organic base such as triethylamine.

Compound (c) can be prepared by the following procedure.

Starting 2,4-bis(methoxycarbonyl)cyclopentanone (Compound 1A-A) is known and can be prepared as a mixture of 2,3-bis(methoxycarbonyl)cyclopentanone (Compound 1A-a) by the process described in, e.g., J. Org. Chem., 47, 2379 (1982) or by a modification thereof. After the keto group of the mixture (Compound 1A-B and Compound 1A-b) is protected, the ester is converted into hydroxymethyl by reduction. The protective group is then removed to give 2,4-bis(hydroxymethyl)cyclopentanone (Compound 1A-C) and 2,3-bis(hydroxymethyl)cyclopentanone (Compound 1A-c). Compound (1A-c) is removed by silica gel column chromatography to isolate Compound (1A-C). Compound (1A-C) is acetylated in a conventional manner to give Compound (1A-D). The reaction for preparing Compound (1A-E) from Compound (1A-D) is carried out under similar conditions as used for the condensation between the compounds of formula [2A] and the compounds of formula [3A]. In this case, alpha-thioglycerine is used as the compound of formula [3A]. Next, the 1,2-diol moiety in Compound (1A-E) is protected. As the protective group, an acetal, a ketal or an ortho-ester may be employed. Compound (1A-E) is then converted into the isopropylidene preferably in the presence of an acid catalyst and acetone or its activated derivatives to give Compound (1A-F). Subsequently, Compound (1A-F) is subjected to alkaline hydrolysis in a conventional manner to Starting (4R)-2-(N,N-diethylamino)methyl-4-tert-butyldimethylsiloxy-2-cyclopenten-1-one (Compound 3A-a) is known and commercially available (from, e.g., The Shin-Etsu Chemical Co., Ltd.). For the reaction for preparing Compound (3A-b) from Compound (3A-a), reaction conditions similar to those used for the condensation between the compounds of formula [2A] and formula [3A] may be used. In this reaction, N-acetyl-L-cysteine is employed as the compound of formula [3B]. The protective group for the hydroxy of Compound (3B-b) is removed in a conventional manner, using an acid or a fluorine compound. By oxidation, the sulfide of Compound (3B-c) is then converted into the corresponding sulfone to give Compound (3B-d). The reaction can be performed under conditions similar to those for the oxidation above, so as not to oxidize the hydroxy. The double bond in the ring is then reduced with a reducing agent to give Compound (c). As the reducing agent there may be employed a catalytic reducing agent such as palladium-carbon, etc., a soluble metal reducing agent such as lithium-ammonia, etc., an organic tin hydride compound, an organic silicon hydride compound, etc., preferably a catalytic reducing agent such as palladium-carbon.

The compounds of general formulas [4A] through [7A] other than Compounds (a) to (c) described above may be prepared by appropriately modifying the foregoing processes used to prepare Compounds (a) to (c).

Compound (c) is commercially available (from, e.g., Tokyo Kasei K.K.). Compound (e) is readily prepared by heating Compound (d) in methanol in the presence of an acidic catalyst. As the acidic catalyst, there are an organic acid such as hydrochloric acid, sulfuric acid, etc., an organic acid such as p-toluenesulfonic acid, or a Lewis acid such as boron fluoride etherate, etc., preferably an organic acid such as p-toluenesulfonic acid.

For example, Compound (4A) of the present invention can be readily prepared by amidation of Compound (3A) as shown below.

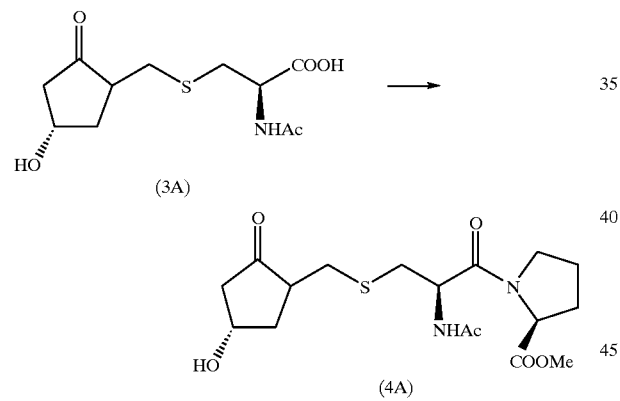

The amidation is effected by condensation under basic conditions or using a condensing agent. The use of a condensing agent is preferable for the amidation. Examples of the condensing agent are dicyclocarbodiimide (DCC) and WSC.

Compounds (5A) and (6A) of the present invention can be prepared by reacting the compounds of general formula [8a] with the compounds of general formula [3A] while heating. The reaction is carried out in the absence of a solvent or in an organic solvent with heating to 30° C. to 200° C. to give the desired product. As the compounds of formula (8A), e.g., (f) 2-(1-piperidylmethyl)-3-oxo-1-indanecarboxylic acid is representative. Compound (f) may be prepared by a modification of the process described in J. Med. Chem., 7, 716 (1964).

[B] Processes for preparing the compounds of formula 1B]

The compounds of general formula [1B] wherein $X_B$ is S, O or NH are prepared by reacting 2,3-substituted cyclopentanone derivatives (the carbonyl at the 1-position may be suitably protected; hereinafter simply referred to as reactive derivatives) represented by general formula [2B]:

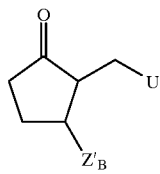

[2B]

(wherein U is a leaving group and, $Z'_B$ has the same significance as that of $Z_B$ but when the group contains a functional group, the functional group may be protected suitably), with compounds of general formula [3B]:

$HX_B2-Y'_B$ [3B]

(wherein $X_B2$ is S, O or NH and $Y'_B$ has the same significance as defined for $Y_B$ but where it contains a functional group, the functional group may be protected suitably), and when required, removing the protective group. Preferred examples of the reactive derivatives described above are compounds of general formulas [4B], [5B], [6B] and [7B].

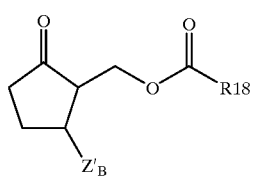

[4B]

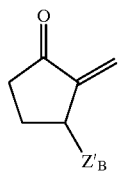

[5B]

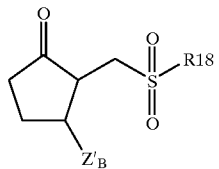

[6B]

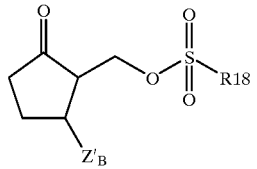

[7B]

In the formulas above, R18 is an aliphatic group having 1 to 10 carbon atoms, such as an alkyl, an alkenyl or an aryl. These groups may be substituted or unsubstituted. Where a functional group(s) are contained as a substituent(s), the functional groups may be adequately protected with protective groups.

Examples of the compounds of general formulas (4B], [5B], [6B] and [7B] are given below.
(a) 2,3-bis(acetoxymethyl)cyclopentanone
(b) 3-acetoxymethyl-2-methylidenecyclopentanone (c) 2-[(2,3-O-isopropylidene)propylsulfonyl]methyl-3-oxo-1-cyclopentanecarboxylic acid (d) 2-[(2,3-O-isopropylidene)propylsulfonyl]methyl-3-methoxycarbonylcyclopentanone (e) 2-methylidene-3-oxo-1-cyclopentanecarboxylic acid (f) 3-methoxycarbonyl-2-methylidenecyclopentanone In the general formula [3B] wherein $X_B$ is S and $Y_B$ is an amino acid derivative residue, the compounds of formula [3B] include the following:

(g) (2R)-2-acetylamino-3-oxo-3-(1-pyrrolidinyl)propanethiol (h) (2R)-2-acetylamino-3-(4-morpholinyl)-3-oxopropanethiol (i) (2R)-2-acetylamino-3-oxo-3-(1-piperidyl)propanethiol (j) (2R)-2-acetylamino-3-oxo-3-(1-pyrrolidinyl)propanethiol (k) (2R)-2-acetylamino-3-[1-{(2S)-2-methoxycarbonyl}pyrrolidinyl)-3-oxopropanethiol (l) (2R)-2-acetylamino-3-[1-{(2S)-2-methoxycarbonyl}azetidinyl)-3-oxopropanethiol (m) (2R)-2-acetylamino-3-oxo-3-(1-piperazinyl)propanethiol (n) (2R)-2-acetylamino-3-{1-(4-hydroxymethyl)piperazinyl}-3-oxopropanethiol (o) (2R)-2-acetylamino-3-{1-(4-tert-butoxycarbonyl}piperazinyl)-3-oxopropanethiol (p) (2R)-2-acetylamino-3-{1-(4-phenyl)piperazinyl}-3-oxopropanethiol (q) (2R)-2-carboxy-2-pentafluoropropionylaminoethanethiol (r) 1-acetylamino-1-carboxy-11-mercaptoundecanethiol (s) 2-acetylamino-2-(5-tetrazolyl)ethanethiol (t) 3-(3-pyridyl)propanethiol (u) 3-{3-(1-methylpyridinium iodide)}propanethiol The above reaction may be effected through any condensation so long as the compounds of formula [2B] can be condensed with the compounds of formula [3B]. The reaction is carried out generally in an organic solvent, water or a mixture thereof. As the organic solvent there may be employed an aromatic hydrocarbon such as benzene, toluene, etc.; an alcohol such as methanol, ethanol, etc.; an ether such as tetrahydrofuran, diethyl ether, etc.; a halogenated hydrocarbon such as methylene chloride, chloroform, etc.; a ketone such as acetone, methyl ethyl ketone, etc.; an aprotic polar solvent such as dimethyl sulfoxide, dimethylformamide, etc. Preferred examples of the solvent are an ether such as tetrahydrofuran or diethyl ether, a halogenated hydrocarbon such as methylene chloride or chloroform, a ketone such as acetone or methyl ethyl ketone, an aprotic polar solvent such as dimethyl sulfoxide or dimethylformamide, or a mixture of such solvent and water. The reaction proceeds generally in the presence of an acid or a base or in the absence of a catalyst, preferably under basic conditions. Reactants used for the reaction are inorganic bases, e.g., potassium hydroxide, sodium hydroxide, potassium carbonate, sodium carbonate, sodium hydride, etc., or organic bases such as triethylamine, 1,8-diazabicyclo[5.4.0]-undeca-7-ene, etc. These reactants are employed in an amount of approximately 0.1 to 20-fold mols, preferably approximately 0.5 to 5-fold mols. The reaction temperature is not particularly limited so that the reaction may be carried out under cooling, at ambient temperature or with heating. Preferably, the reaction is performed at a temperature between 0° C. and 100° C. The compounds of formula [2B] may be reacted with the compounds of formula [3B] in an equimolar amount. Practically, the compounds of formula [3B] may be used in an excess amount, e.g., 1 to 2-fold mols. The reaction is performed in 0.1 to 200 hours, preferably 0.1 to 72 hours.

The compounds of formula [1B] wherein $X_B$ is $SO_2$ can be prepared by oxidizing the compounds of formula [1B] wherein $X_B$ is S, with an oxidizing agent. As the oxidizing agent, an organic peracid such as m-chloroperbenzoic acid, etc., an inorganic oxidizing agent such as permanganate, chromic acid, ruthenium tetroxide, etc., hydrogen peroxide, an organic peroxide, etc., preferably an organic peracid such as m-chloroperbenzoic acid.

The compounds of formula [1B] wherein $X_B$ is SO can be prepared by oxidizing the compounds of formula [1B] wherein $X_B$ is S, with an oxidizing agent. As the oxidizing agent, an organic peracid such as m-chloroperbenzoic acid, etc., an inorganic oxidizing agent such as manganese dioxide, chromic acid, ruthenium tetroxide, etc., hydrogen peroxide, an organic peroxide, a halogen type oxidizing agent such as periodic acid, etc.

For example, Compounds (a) and (b) described above are prepared by the following procedure.

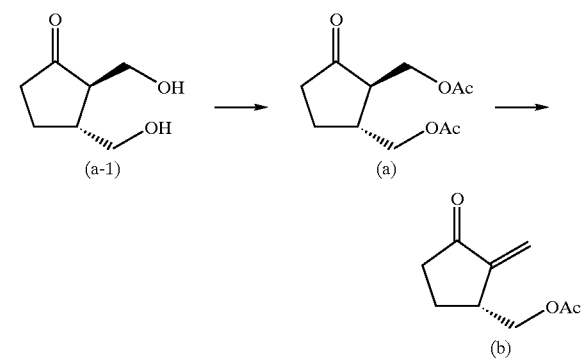

Starting 2,3-bis(hydroxymethyl)cyclopentanone (Compound a-1) is known by literature and may be prepared, e.g., by the method described in Japanese Patent KOKAI No. Hei 5-1044 or a modification thereof. Compound (a-1) is acetylated in a conventional manner to give Compound (a). Compound (a) that is optically active and has a steric configuration of (2R,3R) may be obtained according to the process disclosed in Japanese Patent KOKAI No. Hei 8-231469. The optically active form of Compound (a) may also be prepared, e.g., by optical resolution of the optically inactive form by chromatography for optical resolution. Compound (b) may be prepared by maintaining Compound (a) under basic conditions similar to the conditions used for the condensation between the compounds of formula [2B] and the compounds of formula [3B]; in conducting this reaction, there is no need to use the compounds of formula [3B]. Reactants used for the reaction are inorganic bases, e.g., potassium hydroxide, sodium hydroxide, potassium carbonate, sodium carbonate, sodium hydride, etc., or organic bases such as triethylamine, 1,8-diazabicyclo[5.4.0]-undeca-7-ene, etc., preferably an organic base such as triethylamine.

Compound s (c) and (d) may be prepared as indicated below.

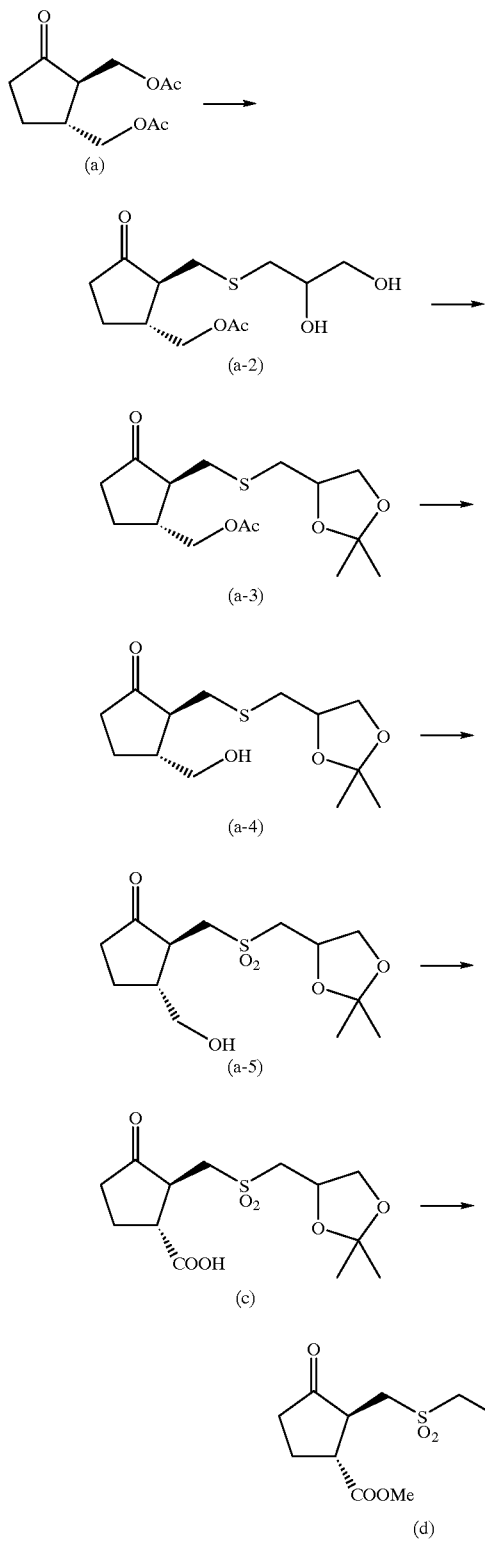

The reaction for preparing Compound (a-2) from Compound (a) is carried out under similar conditions as used for the condensation between the compounds of formula [2B] and the compounds of formula [3B]. In this case, alpha-thioglycerine is used as the compound of formula [3B].

Next, the 1,2-diol moiety in Compound (a-2) is protected. As the protective group, an acetal, a ketal or an ortho-ester may be employed. Compound (a-2) is then converted into the isopropylidene preferably in the presence of an acid catalyst and acetone or its activated derivatives to give Compound (a-3). Subsequently, Compound (a-3) is subjected to alkaline hydrolysis in a conventional manner to remove the acetyl. Thus, Compound (a-4) is obtained. Next, the sulfide of Compound (a-4) is oxidized to the sulfone to prepare Compound (a-5). The reaction is carried out under conditions similar to those used for the oxidation described above, wherein the conditions are set forth so as not to oxidize the hydroxy. In the case that the hydroxy is also oxidized, Compound (a) is obtained. The hydroxy is then oxidized to give Compound (c). Examples of the oxidizing agent that can be used in the reaction are an inorganic oxidizing agents such as permanganates and chromic acid, preferably chromic acid. Finally, the carboxylic acid in Compound (c) is esterified in a conventional manner to prepare Compound (d).

Compounds (e) and (f) can be prepared from Compounds (c) and (d) under conditions similar to the conditions used to convert Compound (a) to Compound (b).

Optically active form (Compounds C and D) of Compounds (c) and (d) may be prepared in a similar manner to the process for preparing Compounds (c) and (d) described above, which is illustrated below.

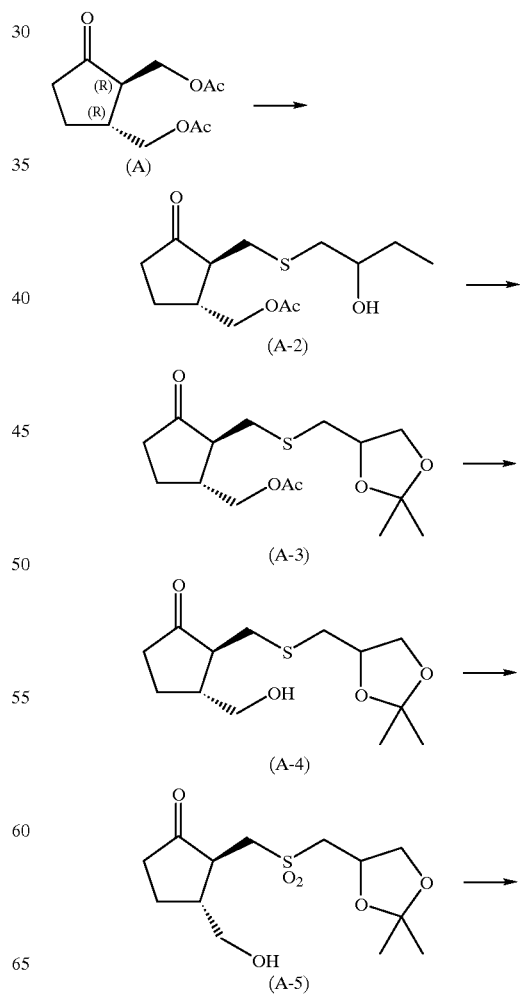

-continued

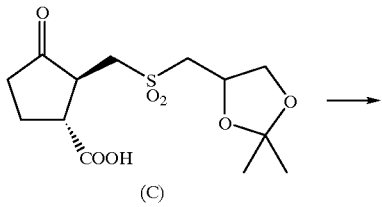

(C)

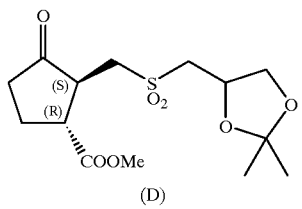

(D)

The compounds of general formulas [4B] through [7B] other than Compounds (a) to (f) described above may be prepared by appropriately modifying the foregoing processes used to prepare Compounds (a) to (f).

Compounds (g) to (u) may be prepared as shown below.

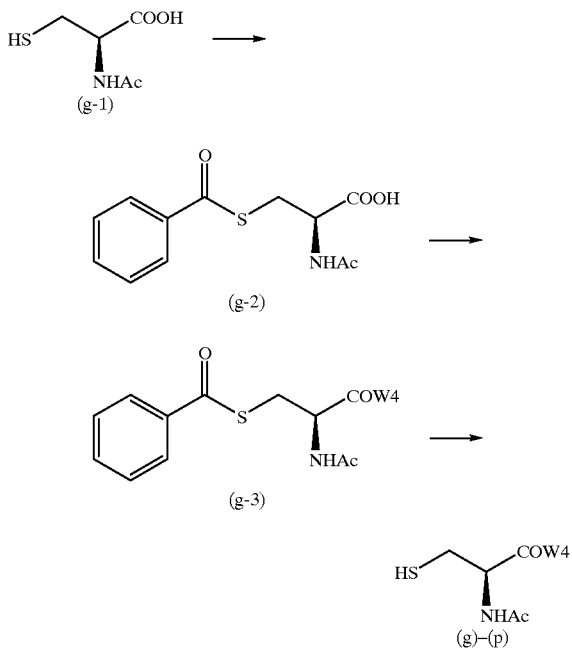

N-acetyl-L-cysteine (g-1) is benzoylated in a conventional manner to prepare Compound (g-2). Then, compounds of general formula [8b] below:

HW4  [8B]

wherein W4 is 1-piperidyl, 1-pyrrolidinyl, 4-morpholinyl, 1-(2-methoxycarbonyl)azetidinyl, 1-(2-methoxycarbonyl) pyrrolidinyl, 1-piperazinyl, 1-(4-hydroxyethyl)piperazinyl, 4-phenylpiperazinyl or 1-(4-tert-butoxycarbonyl) piperazinyl, are subjected to an amide-forming reaction in a conventional manner. Thus, Compound (g-3) is prepared. The protective benzoyl is removed by hydrolysis to give Compounds (g) to (p).

Compound (q) can be readily prepared by reacting L-cysteine with pentafluoropropionic anhydride.

Compound (r) can be prepared as shown below.

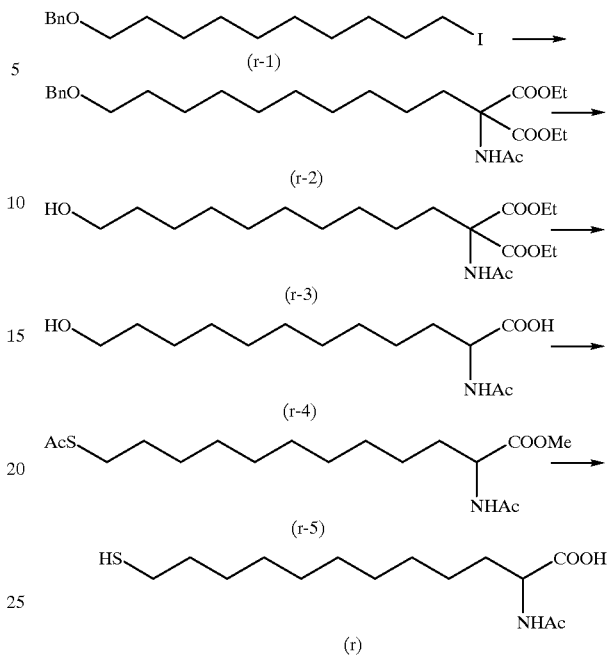

Compound (r-2) can be prepared by reacting Compound (r-1) readily available with diethyl acetylaminomalonate in the presence of a base, which is conventional in preparing amino acid derivatives. Next, protective benzyl is removed in a conventional manner to convert Compound (r-2) into Compound (r-3). Compound (r-3) is heated to decarboxylate under acidic conditions to prepare Compound (r-4). After the carboxy is protected in the form of the methyl ester, the hydroxy is converted into acetylthio under mild conditions in a conventional manner, using as reactants 2-fluoro-1-methylpyridinium p-toluenesulfonate, thioacetic acid and triethylamine. Thus, Compound (r-5) is prepared. By removing methoxy and S-acetyl protective groups under mild basic conditions, Compound (r) is obtained from Compound (r-5).

Compound (s) can be easily prepared by the procedures which comprises converting COOH of thiol-protected L-cysteine to cyano, reacting with sodium azide to convert into 5-tetrazolyl and removing the protective group to liberate thiol.

Compound (t) may be readily prepared by the process described in Chemistry Letters, 133–136 (1977), using 3-pyridinepropanol as a starting compound.

Compound (u) may be readily prepared by reacting thiol-protected Compound (t) with methyl iodide and then liberating thiol by removing the protective group from the resulting pyridinium iodide.

[C] Processes for preparing the compounds of formula [1C]

The compounds of general formula [1C] wherein $X_c$ is S, C or NH are prepared by reacting cyclopentenone derivatives (the carbonyl at the 1-position may be adequately protected; hereinafter simply referred to as reactive derivatives) represented by general formula [2C]:

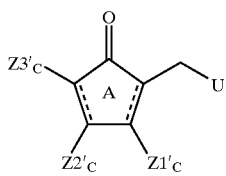

[2C]

(wherein U is a leaving group and, Z1'$_c$, Z2'$_c$ and Z3'$_c$ have the same significance as defined in Z1$_c$, Z2$_c$ and Z3$_c$ but when the group contains a functional group, the functional group may be suitably protected), with compounds of general formula [3C]:

HX$_c$2–Y'$_c$ [3C]

(wherein X$_c$2 is S, O or NH and Y'$_c$ has the same significance as defined for Y$_c$ but where it contains a functional group, the functional group may be properly protected), and when required, removing the protective group. Preferred examples of the reactive derivatives described above are compounds of general formulas [4C], [5C], [6C], [7C] and [8C].

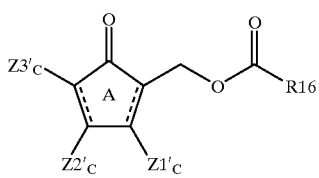

[4C]

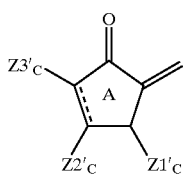

[5C]

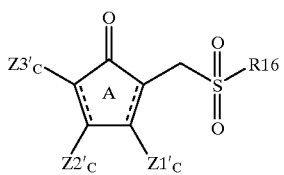

[6C]

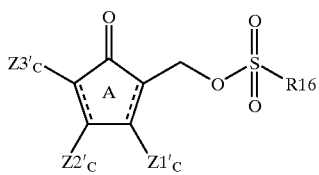

[7C]

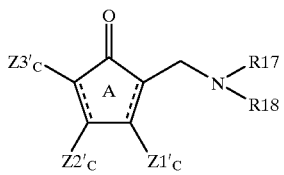

[8C]

In the formulas above, R16 is an aliphatic hydrocarbon group having 1 to 10 carbon atoms, such as an alkyl, an alkenyl or an aryl. These groups may be substituted or unsubstituted. Where a substituent(s) are a functional group (s), the functional groups may be protected with protective groups, if necessary and desired. R17 and R18 each represents hydrogen or an aliphatic hydrocarbon group having 1 to 10 carbon atoms, for example, an alkyl, an alkenyl or an aryl. These groups may be substituted or unsubstituted. Where a substituent(s) are a functional group(s), the functional groups may be protected with protective groups, if necessary and desired. Z1'$_c$, Z2'$_c$ and Z2'$_c$ have the same significance as defined above.

Examples of the compounds of general formulas [4C], [5C], [6C], [7C] and [8C] are illustrated below.

(a) 2-[(2R)-(2-acetylamino-2-methoxycarbonyl) ethylsulfonyl]methyl-4-tert-butyldimethylsiloxy-2-cyclopentan-1-one (b) 2-methylidene-4-tert-butyldimethylsiloxy-2-cyclopentan-1-one (c) 2-diethylaminomethyl-4-tert-butyldimethylsiloxy-2-cyclopenten-1-one (d) 3-acetoxy-2-benzenesulfonylmethyl-2-cyclopenten-1-one In the general formula [3C] wherein X$_c$ is S, the compounds of formula [3C] include the following:

(e) (2R)-2-acetylamino-2-carboxyethanethiol (f) (2R)-2-acetylamino-2-methoxycarbonylethanethiol For conducting the above reaction, any condensation process may be used so long as the compounds of formula [2C] can be condensed with the compounds of formula [3C]. The reaction is carried out generally in an organic solvent, water or a mixture thereof. As the organic solvent there may be employed an aromatic hydrocarbon such as benzene, toluene, etc.; an alcohol such as methanol, ethanol, etc.; an ether such as tetrahydrofuran, diethyl ether, etc.; a halogenated hydrocarbon such as methylene chloride, chloroform, etc.; a ketone such as acetone, methyl ethyl ketone, etc.; an aprotic polar solvent such as dimethyl sulfoxide, dimethylformamide, etc. Preferred examples of the solvent are an ether such as tetrahydrofuran or diethyl ether, a halogenated hydrocarbon such as methylene chloride or chloroform, a ketone such as acetone or methyl ethyl ketone, an aprotic polar solvent such as dimethyl sulfoxide or dimethylformamide, or a mixture of such solvent and water. The reaction proceeds generally in the presence of an acid or a base or in the absence or any catalyst, preferably under basic conditions using inorganic bases, e.g., potassium hydroxide, sodium hydroxide, potassium carbonate, sodium carbonate, sodium hydride, etc., or organic bases such as triethylamine, 1,8-diazabicyclo[5.4.0]-undeca-7-ene, etc. These reactants are employed in an amount of approximately 0.1 to 20-fold mols, preferably approximately 0.5 to 5-fold mols. The reaction temperature is not particularly limited so that the reaction may be carried out under cooling, at ambient temperature or with heating. Preferably, the reaction is performed at a temperature between 0° C. and 100° C. The compounds of formula [2C] may be reacted with the compounds of formula [3C] in an equimolar amount. Practically, the compounds of formula [3C] may be used in an excess amount, e.g., 1 to 2-fold mols. The reaction is performed in 0.1 to 200 hours, preferably 0.1 to 72 hours.

Where Compound (a) or Compound (b) is selected as the compounds of formula [2C], the resulting condensation product is further dehydrated after removal of the protective group for the hydroxy to give the desired cyclopentenone derivative. As reactants for the removal of the protective group and the dehydration, an acid, an acidic resin, a Lewis acid or a fluorine reagent may be employed. The acid that can be used includes an inorganic acid such as hydrochloric acid or sulfuric acid and an organic acid such as p-toluenesulfonic acid and acetic acid. As the acidic resin, preferred is Dowex 50. Boron fluoride etherate or the like is advantageously used as the Lewis acid. The fluorine reagent includes tetrabutylammonium fluoride and hydrogen fluoride.

In the compounds of general formula [2C] wherein $X_c$ is N, that is, where the compounds of formula [7C] are condensed with the compounds of formula [3C], the objective condensation product can be prepared by methylating or oxidizing the nitrogen of the compounds shown by formula [7C] and then reacting the methylated or oxidized product with the compounds of formula [3C]. Examples of the methylating agent are a methyl halide and dimethyl sulfate, preferably methyl iodide. The oxidizing agent includes an organic peracid such as m-chloroperbenzoic acid, hydrogen peroxide, an organic peroxide, etc., preferably an organic peracid such as m-chloroperbenzoic acid, or hydrogen peroxide.

The compounds of formula [1C] wherein $X_c$ is $SO_2$ may be prepared by oxidizing the compounds of formula [1C] wherein $X_c$ is S. The oxidizing agent suitable for use includes an organic peracid such as m-chloroperbenzoic acid, etc., an inorganic oxidizing agent such as manganese dioxide, chromic acid, ruthenium tetroxide, etc., hydrogen peroxide, an organic peroxide, preferably an organic peracid such as m-chloroperbenzoic acid.

The compounds of formula [1C] wherein $X_c$ is SO may be prepared by oxidizing the compounds of formula [1C] wherein $X_c$ is S. The oxidizing agent suitable for use includes an organic peracid such as m-chloroperbenzoic acid, etc., an inorganic oxidizing agent such as manganese dioxide, chromic acid, ruthenium tetroxide, etc., hydrogen peroxide, an organic peroxide, a halogen type oxidizing agent such as periodic acid, etc.

For example, Compound (a) and Compound (b) described above may be prepared as follows.

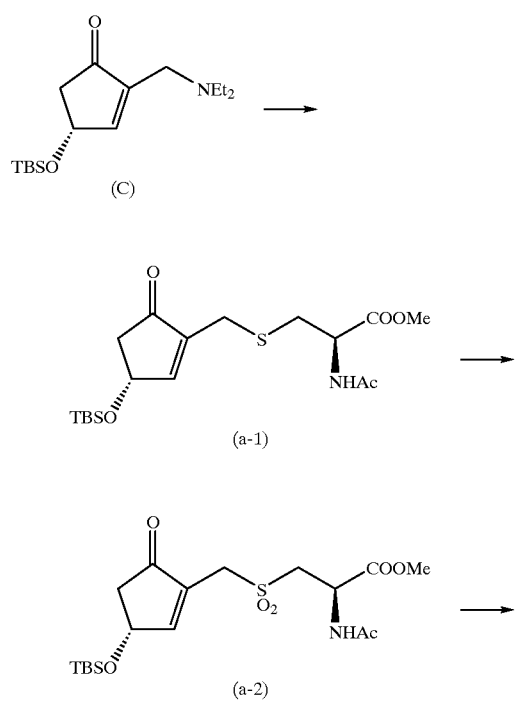

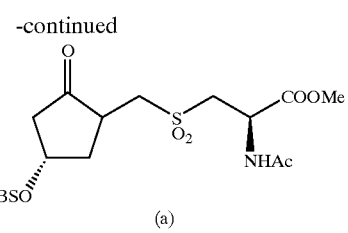

Starting Compound (c) is known and commercially available from, e.g., Nissan Chemical Co., Ltd. Compound (c) may be converted into Compound (a-1) under reaction conditions similar to those used for the condensation of the compounds of formula [2C], wherein Xc is N. Next Compound (a-2) may be produced under reaction conditions similar to those for the oxidation to $SO_2$ described above. The carbon-carbon double bond of Compound (a-2) may be reduced in a conventional manner to give Compound (a). As the reducing agent there may be employed an alkaline metal reducing agent, an organic tin reducing agent, an organic silicon reducing agent, a catalytic hydrogenation reducing agent, etc., preferably a catalytic hydrogenation reducing agent such as palladium-carbon, etc. Compound (b) may be prepared by maintaining Compound (a) under basic conditions. Reactants that may be used for the basic conditions are an inorganic base such as potassium hydroxide, sodium hydroxide, potassium carbonate, sodium carbonate, sodium hydride, etc., and an organic base such as triethylamine, 1,8-diazabicyclo[5.4.0]-undeca-7-ene, etc., preferably an organic base such as triethylamine or 1,8-diazabicyclo [5.4.0]-undeca-7-ene.

Compound (d-1) is known by literature and may be prepared, e.g., by the method described J. Org. Chem., 58, 3953–3959 (1993). By acetylation of Compound (d-1) in a conventional manner, Compound (d) may be prepared.

The compounds of formula [4C] through [8C] other than Compounds (a) to (d) may be prepared by appropriately modifying the above procedures for preparing Compounds (a) to (d).

Compound (e) is commercially available from, e.g., Tokyo Kasei K.K. Compound (f) is readily prepared by heating Compound (e) in methanol in the presence of an acidic catalyst. As the acidic catalyst, there are an organic acid such as hydrochloric acid, sulfuric acid, etc., an organic acid such as p-toluenesulfonic acid, or a Lewis acid such as boron fluoride etherate, etc., preferably an organic acid such as p-toluenesulfonic acid.

[D] Processes for preparing the compounds of formula [1D]

The compounds of general formula [1D] wherein $X_D$ is S, O or NH are prepared by reacting ketone derivatives (the carbonyl at the 1-position may be protected appropriately; hereinafter simply referred to as reactive derivatives) represented by general formula [2D]:

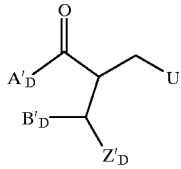
[2D]

(wherein U is a splitting-off group and, $A'_D$, $B'_D$ and $Z'_D$ have the same significance as defined in $A_D$, $B_D$ and $Z_D$ but where the group contains a functional group, the functional group may be protected suitably), with compounds of general formula [3D]:

$HX_D2-Y''_D$ [3D]

(wherein $X_D2$ is S, O or NH and $Y'_D$ has the same significance as defined for $Y_D$ but where it contains a functional group, the functional group may be properly protected), and when required, removing the protective group. Preferred examples of the reactive derivatives described above are compounds of general formulas [4D], [5D], [6D], [7D] and [8D].

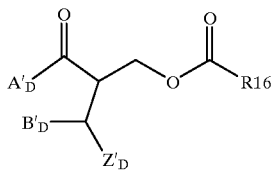
[4D]

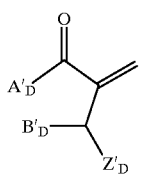
[5D]

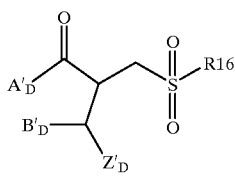
[6D]

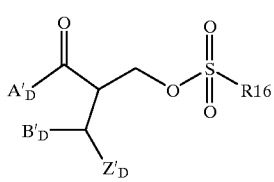
[7D]

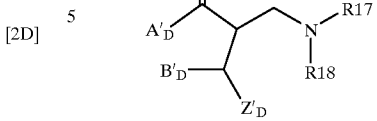
[8D]

In the formulas above, R16 is an aliphatic group having 1 to 10 carbon atoms, such as an alkyl, an alkenyl or an aryl. These groups may be substituted or unsubstituted. Where a substituent(s) are a functional group(s), the functional groups may be appropriately protected with protective groups. Each of R17 and R18, which may be the same or different, independently represents an alkyl having 1 to 4 carbon atoms or R17 and R18 are combined together to form a piperazine ring or a pyrrolidine ring. $A'_D$, $B'_D$ and $Z'_D$ have the same significance as defined above. R16 and $Z'_D$ may also be combined together to form a γ-butyrolactone ring.

Examples of the compounds of general formulas [4D], [5D], [6D], [7D] and [8D] are shown below.

(a) 4-acetyl-γ-butyrolactone
(b) 3-methylidene-4-oxo-1-n-pentanoic acid
(c) trans-2,3-bis(acetoxymethyl)-1-cyclobutanone
(d) 3-acetoxymethyl-2-methylidene-1-cyclobutanone
(e) 3-ethoxycarbonyl-2-methanesulfoxymethyl-1-cyclobutanone
(f) 3-ethoxycarbonyl-2-methylidene-1-cyclobutanone
(g) 2-[(2,3-O-isopropylidene)propylsulfonyl]-methyl-3-oxo-1-cyclohexanecarboxylic acid
(h) 2-methylidene-3-oxo-1-cyclohexanecarboxylic acid
(i) 4-oxo-4-phenyl-3-(1-piperidyl)methylbutyric acid
(j) 4-oxo-4-(3-pyridyl)-3-(1-piperidyl)methylbutyric acid
(p) 4-(1-piperidyl)methyl-5-oxo-5-phenylpentanoic acid In the compounds of formula [3D] wherein $X_D$ is S, the compounds of formula [3D] include the following:

(q) (2R)-2-acetylamino-2-carboxyethanethiol
(r) (2R)-2-acetylamino-2-methoxycarbonylethanethiol
(s) 2,3-dihydroxypropane-1-thiol (alphathioglycerine)

For conducting the above reaction, any condensation process may be used so long as the compounds of formula [2D] can be condensed with the compounds of formula [3D]. The reaction is carried out generally in an organic solvent, water or a mixture thereof. As the organic solvent there may be employed an aromatic hydrocarbon such as benzene, toluene, etc.; an alcohol such as methanol, ethanol, etc.; an ether such as tetrahydrofuran, diethyl ether, etc.; a halogenated hydrocarbon such as methylene chloride, chloroform, etc.; a ketone such as acetone, methyl ethyl ketone, etc.; an aprotic polar solvent such as dimethyl sulfoxide, dimethylformamide, etc. Preferred examples of the solvent to be used are an ether such as tetrahydrofuran or diethyl ether, a halogenated hydrocarbon such as methylene chloride or chloroform, a ketone such as acetone or methyl ethyl ketone, an aprotic polar solvent such as dimethyl sulfoxide or dimethylformamide an alcohol such as methanol or ethanol, or a mixture of such solvent and water. The reaction proceeds generally in the presence of an acid or a base or in the absence or any catalyst, preferably under basic conditions. Where no catalyst is used, the reaction may sometimes proceed with heating. Reactants used to make the reaction system are an inorganic base such as potassium hydroxide, sodium hydroxide, potassium carbonate, sodium carbonate, sodium hydride, etc., or an organic base such as triethylamine, 1,8-diazabicyclo[5.4.0]-undeca-7-ene, etc. These reactants are employed in an amount of approximately 0.1 to 20-fold mols, preferably approximately 0.5 to 5-fold mols. The reaction temperature is not particularly limited so that the reaction may be carried out under cooling, at ambient temperature or with heating. Preferably, the reaction is performed at a temperature between −20° C. and 130° C. Where the condensation is performed in the absence of a catalyst, the temperature is preferably between 30° C. and 200° C. The compounds of formula [2D] may be reacted with the compounds of formula [3D] in an equimolar amount. Practically, the compounds of formula [3D] may be used in an excess amount, e.g., 1 to 2-fold mols. The reaction is performed in 0.1 to 200 hours, preferably 0.1 to 72 hours.

The compounds of formula [1D] wherein $X_D$ is $SO_2$ may be prepared by oxidizing the compounds of formula [1D] wherein $X_D$ is S. The oxidizing agent suitable for use in the oxidation includes an organic peracid such as m-chloroperbenzoic acid, etc., an inorganic oxidizing agent such as permanganate, chromic acid, ruthenium tetroxide, etc., hydrogen peroxide, an organic peroxide, etc., preferably an organic peracid such as m-chloroperbenzoic acid.

The compounds of formula [1D] wherein $X_D$ is SO may be prepared by oxidizing the compounds of formula [1D] wherein $X_D$ is S. The oxidizing agent suitable for use in the oxidation includes an organic peracid such as m-chloroperbenzoic acid, etc., an inorganic oxidizing agent such as manganese dioxide, chromic acid, ruthenium tetroxide, etc., hydrogen peroxide, an organic peroxide, a halogen type oxidizing agent such as periodic acid, etc.

For example, Compound (a) and Compound (b) described above may be prepared as follows.

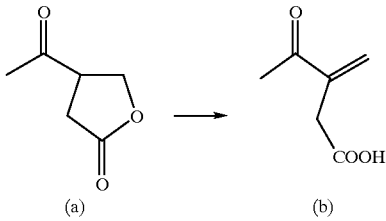

Compound (a) is known and may be prepared, e.g., by the method described in Bull. Chem. Soc. Jpn., 32, 1282 (1959). Compound (b) is also known and may be prepared, e.g., by the process disclosed in Japanese Patent KOKOKU Showa 37-5911. Compound (b) may be prepared by maintaining Compound (a) under acidic or basic conditions. Reactants used for the above reaction are an inorganic base such as potassium hydroxide, sodium hydroxide, potassium carbonate, sodium carbonate, sodium hydride, etc., an organic base such as triethylamine, 1,8-diazabicyclo[5.4.0]-undeca-7-ene, etc., an in-organic acid such as hydrochloric acid, sulfuric acid, etc., and an organic acid such as p-toluenesulfonic acid, preferably an organic base such as triethylamine, 1,8-diazabicyclo[5.4.0]-undeca-7-ene or an inorganic acid such as sulfuric acid.

Compounds (c) and (d) can be prepared as follows.

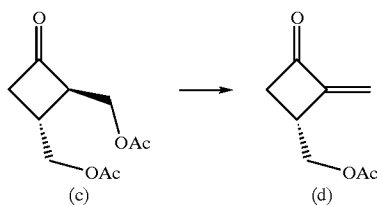

Compound (c) analogues are known and described in, e.g., Tetrahedron Lett., 6453 (1989) and Compound (c) itself can be readily prepared by the process described therein. Compound (d) can be prepared by maintaining Compound (c) under basic conditions. Reactants that may be advantageously used for the reaction are an inorganic base such as potassium hydroxide, sodium hydroxide, potassium carbonate, sodium carbonate, sodium hydride, etc., and an organic base such as triethylamine, 1,8-diazabicyclo[5.4.0)-undeca-7-ene, etc., preferably an organic base such as triethylamine or 1,8-diazabicyclo(5.4.0]-undeca-7-ene.

Compounds (e) and (f) may be prepared as follows.

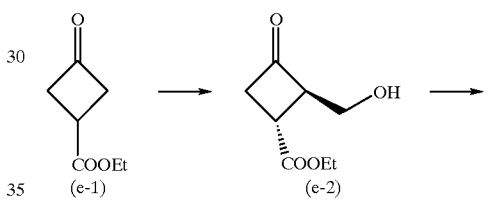

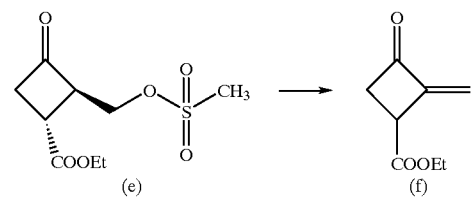

Compound (e-1) is known and may be prepared, e.g., by the process described J. Org. Chem., 53, 3841 (1988). To convert Compound (e-1) to Compound (e) and then Compound (f), the process described in J. Org. Chem., 53, 611 (1988) is applied by appropriate modification. That is, Compound (e-2) can be prepared by treating Compound (e-1) with a base and treating the anions generated with formaldehyde. As the base, there may be used LDA, n-butyl lithium, KHMDS, sodium hydride, etc., preferably LDA. Formaldehyde is preferably reacted as a monomer after cracking of its polymer. Compound (e) can be prepared by mesylation of Compound (e-2) in a conventional manner. More specifically, Compound (e-2) is reacted with mesyl chloride as a reactant in methylene chloride, while ice-cooling, in the presence of triethylamine as a base. Then Compound (f) can be produced via Compound (e) spontaneously under the same system at a time.

Compounds (g) and (h) may be prepared as follows.

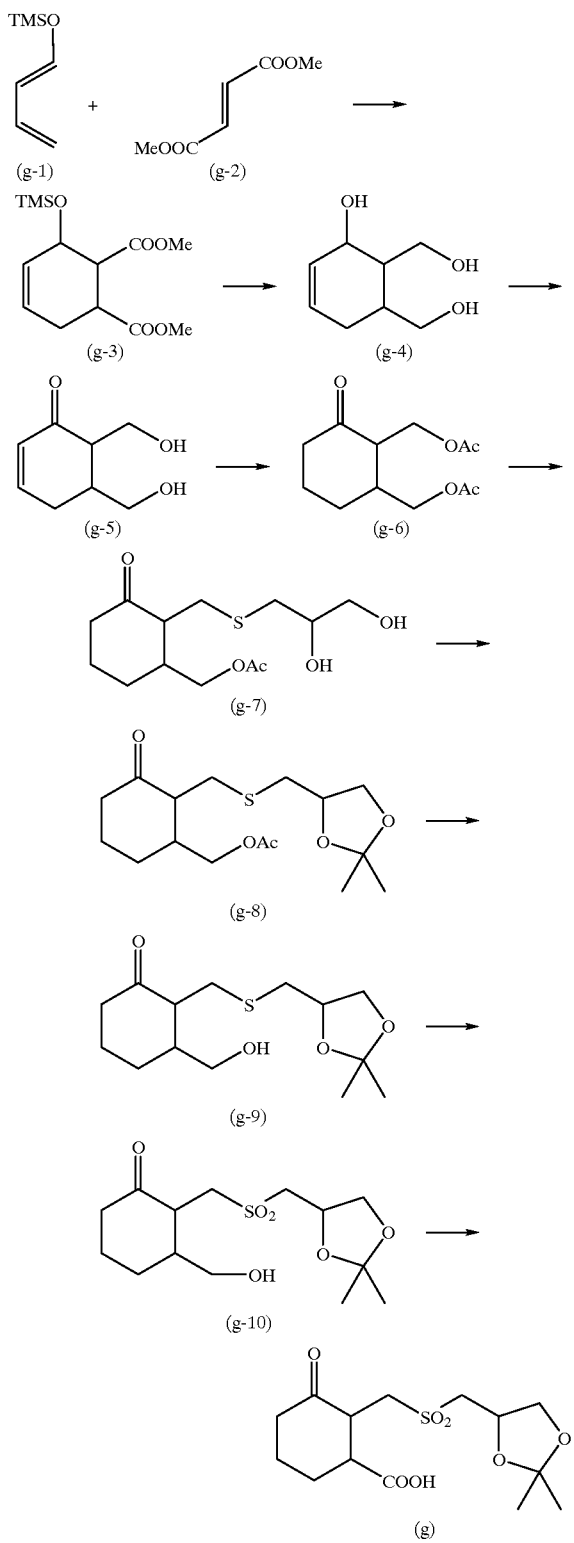

Compound (g-1) and Compound (g-2), which are known by literature and commercially available, are subjected to Diels-Alder reaction in a conventional manner to give Compound (g-3). Compound (g-3) is converted into Compound (g-4) through the reduction with lithium aluminum hydride and the removal of silyl protective group. The allyl alcohol moiety in Compound (g-4) is oxidized with manganese dioxide in a conventional manner. The hydroxy groups of resulting Compound (g-5) is acetylated in acetic anhydridepyridine as a reactant followed by the reduction of the double bond in the ring with palladium-carbon. Compound (g-6) can thus be readily prepared.

The reaction of Compound (g-6) to give Compound (g-7) can be performed under conditions similar to those used to condense the compounds of formula [2D] and the compounds of formula [3D]. In this reaction, alpha-thioglycerine is employed as the compound of formula [3D]. Next, the 1,2-diol group of Compound (g-7) is protected with a protective group such as an acetal, a ketal or an ortho-ester. Preferably, Compound (g-7) is reacted with acetone or its activated derivative in the presence of an acid catalyst to give Compound (g-8), where the 1,2-diol is protected with the isopropylidene. Subsequently, the acetyl is removed by alkaline hydrolysis in a conventional manner to give Compound (g-9). The sulfide of Compound (g-9) is oxidized to the sulfone. Thus, Compound (g-10) is prepared. The reaction is carried out under such conditions that are similar to those used for the oxidation but the hydroxy is not oxidized. Where the hydroxy is oxidized to COOH, Compound (g) can be prepared in one step. Compound (g) can be prepared by oxidizing the hydroxy with an oxidizing agent. The oxidizing agent that can be used includes an inorganic acid such as a permanganate, chromic acid, etc., preferably chromic acid. Compound (h) can be prepared by maintaining Compound (g) under basic conditions similar to those used to condense the compounds of formula [2D] and the compounds of formula [3D], without adding the compounds of formula [3D] to the reaction system. Reactants that may be advantageously used for the reaction are an inorganic base such as potassium hydroxide, sodium hydroxide, potassium carbonate, sodium carbonate, etc., and an organic base such as triethylamine, 1,8-diazabicyclo[5.4.0]-undeca-7-ene, etc., preferably an organic base such as triethylamine.

Compound (i) is known and may be prepared, e.g., by the process described in J. Chem. Soc. (C), 2308 (1967). Compound (j) may be prepared by reacting the corresponding aldehyde with an acrylic acid derivative in the presence of a catalyst such as sodium cyanide or 3-benzyl-5-(2-hydroxyethyl)-4-methylthiazolium chloride, etc. (Chem. Ber., 109, 289, 541 (1976)) and then subjecting the reaction product to Mannich reaction. Compound (p) can be prepared by subjecting known 5-oxo-5-phenylpentanoic acid to Mannich reaction.

Compounds (q) and (s) are commercially available from, e.g., Tokyo Kasei K.K. Compound (r) can be readily prepared by heating Compound (q) in methanol in the presence of an acid catalyst. As the acidic catalyst, there are an in-organic acid such as hydrochloric acid, sulfuric acid, etc., an organic acid such as p-toluenesulfonic acid, or a Lewis acid such as boron fluoride etherate, etc., preferably an organic acid such as p-toluenesulfonic acid.

[E] Process for preparing the compound of formula [1E]

The compound of formula [1E] (hereinafter sometimes referred to as physiologically active substance NA) may be prepared by culturing NA 32176-producing strain belonging to the genus Streptomyces to produce and accumulate the physiologically active substance NA32176A and collecting the physiologically active substance NA32176A from the culture solution. A representative examples of bacteria capable of producing the physiologically active substance NA32176A has the following microbiological and physiological properties.

1. Morphological properties

When observed after incubation at 27° C. for 2 weeks, aerial mycelia are simply branched and spiral or hook-like at the top. Neither sporangia nor verticillate branch are noted. No zoospore is noted, either. The surface of spores is flat or rough. The spores are cylindrical and have a size of 0.7 to 0.9×1.3 μm. The spores are formed in more than 20 chains.

2. Growth in various media

Growth conditions at 27° C. for 2 weeks in various media are shown in Table 1 below.

TABLE 1

| Medium | Growth | Aerial Mycelium | Substrate Mycelium | Soluble Pigment |
|---|---|---|---|---|
| Sucrose-nitrate agar medium | moderate | moderate, brownish white ~light brownish grey ~black (hygroscopic) | colorless ~light yellow | none |
| Glucose-asparagine-agar medium | moderate | abundant, brownish white~light brownish grey ~black (hygroscopic) | light yellow ~brown | slightly brownish |
| Glycerine-asparagine-agar medium (ISP 5 med.) | moderate | abundant, brownish white~ light brownish gray~black (hygroscopic) | colorless~ light yellow | brownish |
| Starch-inorganic salt-agar medium (ISP 4 med.) | good | moderate, brownish white~light brownish gray ~black (hygroscopic) | light yellow | slightly ~brownish |
| Tyrosine-agar medium (ISP 7 med) | good | moderate, brownish white~light brownish gray ~black (hygroscopic) | light yellow | brownish |
| Nutrient-agar medium | moderate | moderate, white | light yellow | slightly brownish |
| Yeast-maltose-agar medium (ISP 2 med.) | good | abundant, brownish white~light brownish gray ~black (hygroscopic) | colorless | slightly brownish |
| Oatmeal-agar medium (ISP 3 med.) | moderate | moderate, brownish white~light brownish gray ~black (hygroscopic) | colorless | none |

3. Physiological properties

1) Optimum growth temperature range: 24~37° C.

2) Reduction of nitrate: negative

3) Liquefaction of gelatin (glucose-peptone-gelatin medium, 20° C.) : pseudo-positive 4) Hydrolysis of starch (starch-inorganic salt-agar medium): positive 5) Solidification of skimmed milk: negative 6) Peptonization of skimmed milk: positive 7) Formation of melanoid pigment: negative 4. Assimilation of carbon sources (Pridham-Gottlieb agar medium)

| | |
|---|---|
| L-Arabinose | + |
| D-Xylose | + |
| D-Glucose | + |
| D-Fructose | + |
| Sucrose | + |
| Inositol | − |
| L-Rhamnose | − |
| Raffinose | + |
| D-Mannitol | + |

5. Diaminopimelic acid in cell wall

LL-diaminopimelic acid

From the foregoing results, the cell wall of this strain is LL-diaminopimelic acid; according to International Streptomyces Project (abbreviated as ISP), the morphology of spore-forming mycelium belongs to section spirales. The surface of spores is flat or rough; the mycelia are of gray color-series and hygroscopic. Melanin-like pigment is not produced. The substrate mycelium shows light yellow or light brown. The strain assimilates as carbon sources L-arabinose, D-glucose, D-fructose, sucrose, raffinose, D-mannose, D-mannitol and D-xylose.

Based on the foregoing properties, survey was made according to R. E. Buchanan & N. E. Gibbons, Bergey's Manual of Determinative Bacteriology, 8th edition, 1974; the strain NA32176 was found to belong to the genus Streptomyces. Therefore, the strain was named Streptomyces sp. NA32176.

The strain was deposited in the National Institute Bioscience and Human-Technology Agency of Industrial Science and Technology (No. 1-3, Higashi 1-chome, Tsukubashi, Ibaraki, Japan) on Aug. 8, 1997 and received FERM P-16372 as an accession number. Then the deposition was transferred into an international deposition under the Budapest Treaty on Jul. 7, 1998 and received FERM BP-6411 as an accession number.

The strain capable of producing the physiologically active substance NA32176A of the present invention having the aforesaid neuron differentiation promoting activity belongs to the genus Streptomyces. Streptomyces sp. NA32176 (Accession No. FERM P-16372 in the National Institute Bioscience and Human-Technology Agency of Industrial Science and Technology; International Accession No. FERM BP-6411), which was isolated by the present inventors, is one example of the strains used most effectively in this invention.

The strain belonging to the genus Streptomyces employed in the present invention are susceptible to change in their properties, like other strains belonging to the genus Streptomyces, and thus readily mutated by artificial mutation using, e.g., UV rays, X rays or chemicals. Any mutant can be used for the present invention so long as it is capable of producing the physiologically active substance NA32176A of the present invention.

For producing the physiologically active substance NA32176A according to the present invention, the strain described above is aerobically incubated in a medium containing nutrients Streptomyces can assimilate. As nutrient sources, known nutrients heretofore used for the incubation of Streptomyces may be employed. As carbon sources, there are glucose, fructose, glycerine, sucrose, dextrin, galactose, organic acids, etc., that may be used, alone or in combination thereof.

As inorganic and organic nitrogen sources, there are ammonium chloride, ammonium sulfate, urea, ammonium nitrate, sodium nitrate, peptone, meat extract, yeast extract, dry yeast, corn steep liquor, soybean powder, cotton seed lees, Casamino acid, bacto-soyton, soluble vegetable protein, oatmeal, etc., which may be employed, alone or in combination.

If necessary and desired, inorganic salts such as sodium chloride, calcium carbonate, magnesium sulfate, copper sulfate, iron sulfate, zinc sulfate, manganese chloride, phosphoric acid salts, etc. may also be supplemented to the system. Furthermore, organic materials such as amino acids, vitamins, nucleic acids and inorganic substances may also be supplemented appropriately in the culture system.

For incubation, liquid culture, especially deep spinner culture is most suitable. It is desired to perform incubation at a temperature of 20° C. to 40° C. at a pH range of slightly acidic to slightly alkaline nature.

In liquid culture, the incubation generally for 3 to 5 days results in the production and accumulation of the substance NA32176A in the culture broth. The incubation is terminated when the amount of the substance produced reached the maximum. The cells are then separated from the medium by filtration and the product is purified and isolated.

The purification and isolation of the product from the filtrate may be effected by methods conventionally applied to the separation and purification of a metabolite from a microorganism from the cultured cells.

That is, the culture broth is separated into the filtrate and the cells by conventional filtration. The filtrate is passed through a DIAION HP-20 (trademark, Mitsubishi Chemical Industries, Ltd.) column under alkaline conditions to adsorb the objective substance. After washing with water, the column was eluted in a linear gradient from water to 80% hydrated methanol. The eluted active fraction is concentrated and methanol is distilled off. The resulting concentrate is extracted with n-butanol under acidic conditions of hydrochloric acid.

The n-butanol phase is concentrated in vacuum. The concentrate is then subjected to Sephadex LH-20 (trademark, Pharmacia Biotech) column chromatography (moving phase: methanol). The collected active fractions are concentrated and dissolved in a mixture of ethyl acetate-water (1:1). The solution is subjected to centrifugal liquid-liquid partition chromatography (manufactured by Sanki Engineering K.K., CPC-LLB-M) using as a fixing phase the lower layer of the ethyl acetate-water mixture above. After washing with the upper layer of the mixture, the active fraction is reversely eluted with the lower layer. Further Sephadex LH-20 column chromatography (moving phase: methanol) gives NA32176A.

Physicochemical properties of the thus obtained physiologically active substance NA32176A are shown below.
1) Appearance: white powder
2) Molecular weight: 418
3) Molecular formula: C18H$_{30}$N$_2$O$_7$S
   (determined by high resolution mass spectrum)
4) Solubility:
   soluble in a lower alcohol, water or dimethylsulfoxide;
   insoluble in hexane or petroleum ether
5) Rf value by ODS thin layer chromatography:
   0.7 with a developing solvent of n-butanol:acetic acid:water (4:1:2)
6) UV absorption spectrum:
   showing terminal absorption in water
7) IR absorption spectrum:
   The spectrum measured with potassium tablet is shown in FIG. 1.

Figure 2:
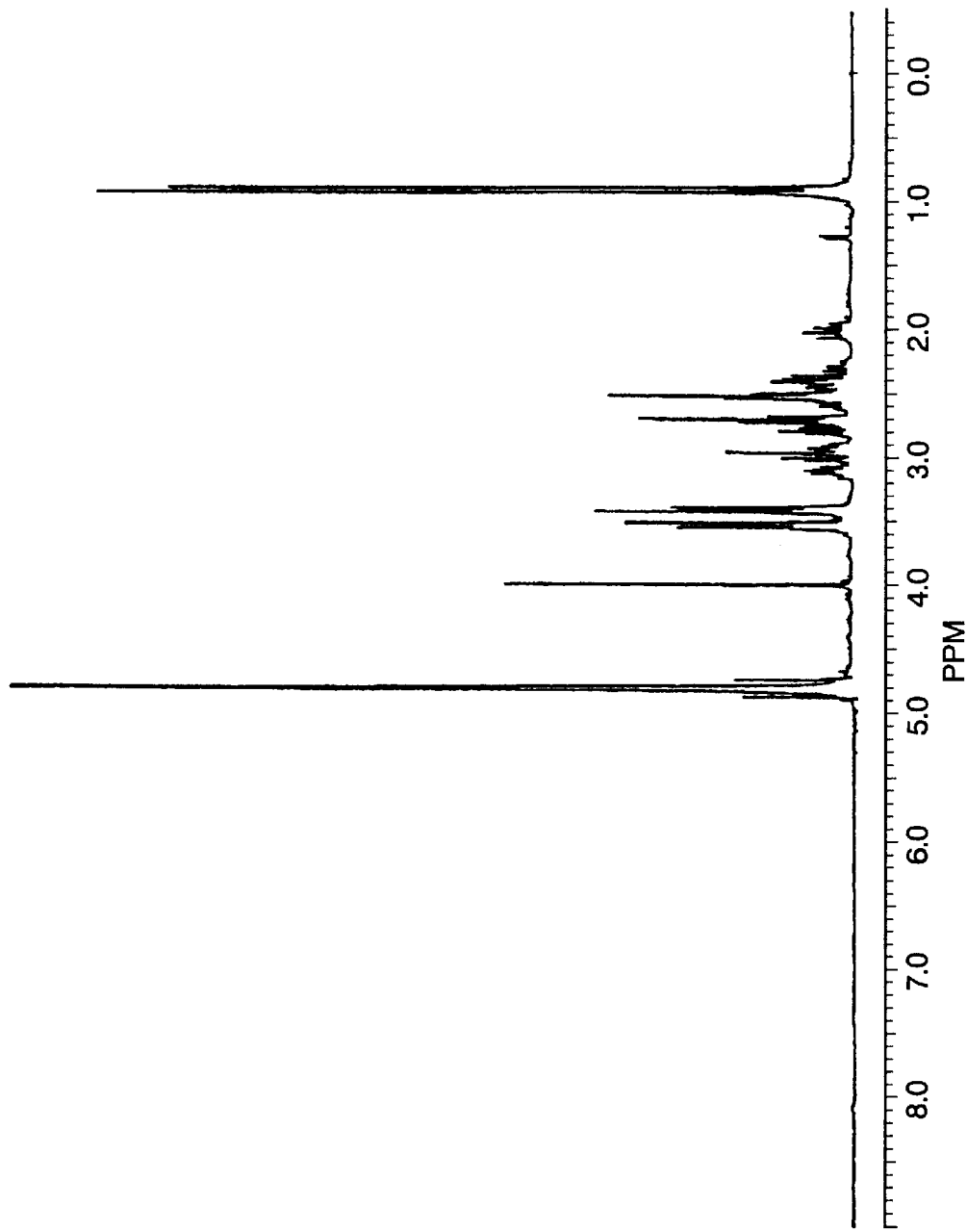
FIG. 2 shows the hydrogen nuclear magnetic resonance spectrum of NA32176A (compound of formula [1E]) measured in heavy water.
Figure 3:
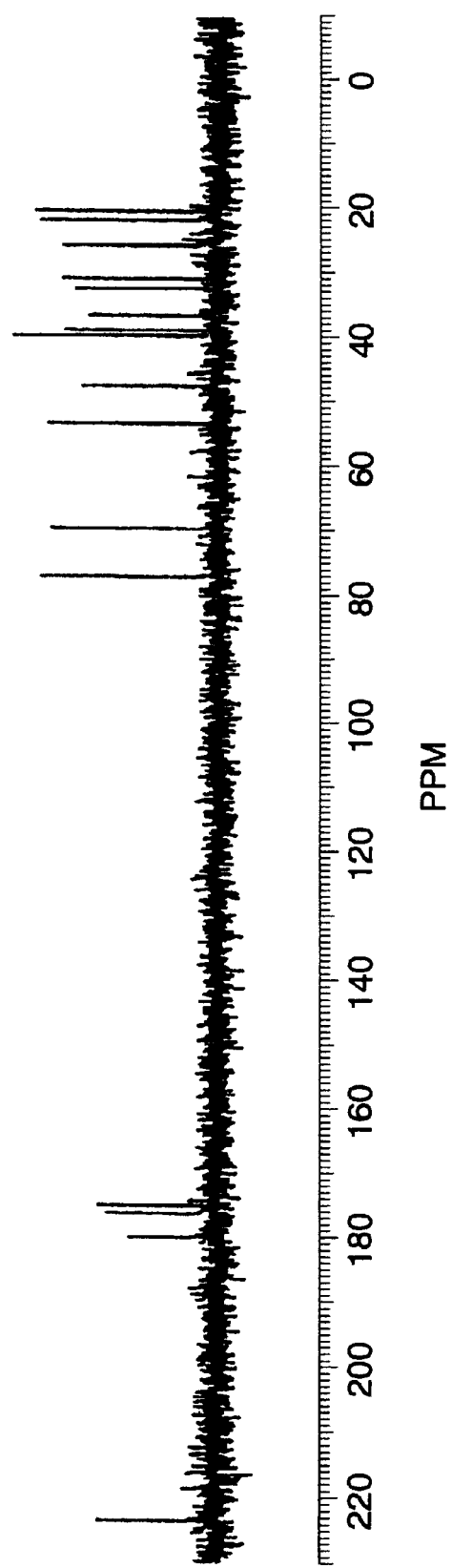
FIG. 3 shows the hydrogen nuclear magnetic resonance spectrum of NA32176A (compound of formula [1E]) measured in heavy water.

8) Hydrogen nuclear magnetic resonance spectrum:
   The spectrum measured in heavy water is shown in FIG. 2.
9) Carbon nuclear magnetic resonance spectrum:
   The spectrum measured in heavy water is shown in FIG. 3. Chemical shift data is shown below.
   δ (ppm) 223.5 (s), 180.1 (s), 176.4 (s), 175.1 (s), 77.0 (d), 69.6 (t), 53.4 (d), 47.7 (d), 39.8 (s), 39.7 (t), 38.9 (t), 36.7 (t), 36.5 (t), 32.5 (t), 31.0 (t), 25.7 (t), 21.8 (q), 20.3 (q)
10) Color-forming reaction:
    positive with phosphorus molybdate and palladium chloride The physiologically active substance NA32176A represented by formula [1E] may also be prepared in a manner similar to the processes for producing the compounds of formula [1B] described above.

In more detail, the physiologically active substance NA32176A may be readily produced by using pantetheine (a product of cysteamine and pantothenic acid bound to each other) as the compound of formula [3B] and condensing pantetheine under conditions similar to those used with Compounds (a) through (f).

Pantetheine is known by Helv. Chim. Acta, 35, 1903 (1952) and may be readily prepared by hydrolysis of pantetheine S-benzoyl ester under alkaline conditions in a conventional manner.

[F] Processes for preparing the compounds of formula [1F]
The compounds of general formula [1F] may be prepared by reacting compounds of general formula [2F]:

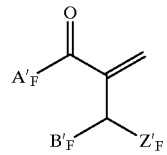

[2F]

(wherein A'$_F$, B'$_F$ and Z'$_F$ have the same significance as defined in A$_F$, B$_F$ and Z$_F$ but where the group contains a functional group, the functional group may be protected suitably), with compounds of general formula [3F]:

HNX'$_F$Y'$_F$ [3F]

(wherein X'$_F$ and Y'$_F$ have the same significance as defined for X$_F$ and Y$_F$ but where it contains a functional group, the functional group may be properly protected), and when required, removing the protective group. Most of the compounds of formula [3F] are commercially available. Specific examples of the compounds [3F] are piperidine, pyrrolidine, morpholine, N-methylpiperazine, N-phenylpiperazine, diethylamine, di-n-propylamine, diisopropylamine, etc.

For conducting the above reaction, any condensation process may be used so long as the compounds of formula [2F] can be condensed with the compounds of formula [3F]. The reaction is carried out generally in an organic solvent, water or a mixture thereof. As the organic solvent there may be employed an aromatic hydrocarbon such as benzene, toluene, etc.; an alcohol such as methanol, ethanol, etc.; an ether such as tetrahydrofuran, diethyl ether, etc.; a halogenated hydrocarbon such as methylene chloride, chloroform, etc.; a ketone such as acetone, methyl ethyl ketone, etc.; an aprotic polar solvent such as dimethyl sulfoxide, dimethylformamide, etc. Preferred examples of the solvent to be used are an ether such as tetrahydrofuran or diethyl ether, a halogenated hydrocarbon such as methylene chloride or chloroform, a ketone such as acetone or methyl ethyl ketone, an aprotic polar solvent such as dimethyl sulfoxide or dimethylformamide, an alcohol such as methanol or ethanol, or a mixture of such solvent and water. The reaction proceeds generally in the presence of a base or in the absence or any catalyst. Reactants used to keep the basic conditions are an inorganic base such as potassium hydroxide, sodium hydroxide, potassium carbonate, sodium carbonate, sodium hydride, etc., or an organic base such as triethylamine, 1,8-diazabicyclo[5.4.0]-undeca-7-ene, etc. These reactants are employed in an amount of approximately 0.1 to 20-fold mols, preferably approximately 0.5 to 5-fold mols. The reaction temperature is not particularly limited so that the reaction may be carried out under cooling, at ambient temperature or with heating. Preferably, the reaction is performed at a temperature between −50° C. and 150° C. The compounds of formula [2F] may be reacted with the compounds of formula [3F] in an equimolar amount. Practically, the compounds of formula [3F] may be used in an excess amount, e.g., 1 to 2-fold mols. The reaction is performed in 0.1 to 240 hours, preferably 0.1 to 96 hours.

The compounds of general formula [1F] may be readily prepared by reacting compounds of general formula [4F]:

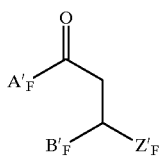

[4F]

(wherein $A'_F$, $B'_F$ and $Z'_F$ have the same significance as defined in $A_F$, $B_F$ and $Z_F$ but where the group contains a functional group, the functional group may be protected suitably), with compounds of general formula [3F]:

$HNX'_F Y'_F$   [3F]

(wherein $X'_F$ and $Y'_F$ have the same significance as defined for $X_F$ and $Y_F$ but where it contains a functional group, the functional group may be properly protected) in the presence of formaldehyde or an equivalent thereto, and when required, removing the protective group. With respect to the details of the compounds of formula [3F], the foregoing description applies thereto.

The condensation process of the compounds of formula [4F] and the compounds of formula [3F] in the presence of formaldehyde or an equivalent thereto is called Mannich reaction, which details are already described in various reviews (e.g., Tetrahedron, 46, 1791 (1990), Synthesis, 1973, 703). The reaction is carried out generally in an organic solvent, water or a mixture thereof. As the organic solvent there may be employed an aromatic hydrocarbon such as benzene, toluene, etc.; an alcohol such as methanol, ethanol, etc.; an ether such as tetrahydrofuran, diethyl ether, etc.; a halogenated hydrocarbon such as methylene chloride, chloroform, etc.; a ketone such as acetone, methyl ethyl ketone, etc.; an aprotic polar solvent such as dimethyl sulfoxide, dimethylformamide, etc. Preferred examples of the solvent are an ether such as tetrahydrofuran or diethyl ether, a halogenated hydrocarbon such as methylene chloride or chloroform, a ketone such as acetone or methyl ethyl ketone, an aprotic polar solvent such as dimethyl sulfoxide or dimethylformamide, an alcohol such as methanol or ethanol, or a mixture of such solvent and water. The reaction proceeds generally in the presence of any catalyst. If necessary and desired, an acid may be used as a catalyst. Example of the formaldehyde equivalent are 1,3,5-trioxane and bis(dimethylamino)methane. Formaldehyde and its equivalents may be used in an amount of approximately 0.9 to 100-fold mols, preferably 1 to 20-fold mols. The reaction temperature is not particularly limited so that the reaction may be carried out under cooling, at ambient temperature or with heating. Preferably, the reaction is performed at a temperature between 0° C. and 200° C. The compounds of formula [4F] may be reacted with the compounds of formula [3F] in an equimolar amount. Practically, the compounds of formula [3F] may be used in an excess amount, e.g., 1 to 2-fold mols. The reaction is performed in 0.1 to 360 hours, preferably 0.1 to 120 hours.

The compounds of general formula [1F] may be readily prepared by reacting compounds of formula [5F]:

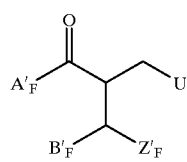

[5F]

(wherein $A'_F$, $B'_F$ and $Z'_F$ have the same significance as defined in $A_F$, $B_F$ and $Z_F$ but where the group contains a functional group, the functional group may be protected suitably, and U is a leaving group and the carbonyl at the 1-position may be suitably protected), with compounds of general formula [3F]:

$HNX'_F Y'_F$   [3F]

(wherein $X'_F$ and $Y'_F$ have the same significance as defined for $X_F$ and $Y_F$, and where it contains a functional group, the functional group may be properly protected), and when required, removing the protective group. The compounds of formula [3F] are detained herein above. The reaction conditions used for the reaction are similar to those for the reaction of the compounds of formula [2F] and [3F].

Preferred examples of the leaving group are chloride, bromine, iodine, methanesulfonyloxy, chloromethanesulfonyloxy, trifluoromethanesulfonyloxy, chloromethanesulfonyloxy and (2,3-O-isopropylidene)propylsulfonyl.

Specific examples of the compounds of formula [5F] are listed below.

(a) 2-[(2,3-O-isopropylidene)propylsulfonyl]methyl-3-oxo-1-cyclopentanecarboxylic acid (b) 2-[(2,3-O-isopropylidene)propylsulfonyl]methyl-3-methoxycarbonylcyclopentanone As a representative process for preparing the compounds of formula [2F] is described below. That is, the compounds of formula [2F] may be readily prepared by reacting the compounds of formula [4F]:

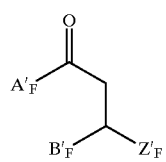

[4F]

(wherein $A'_F$, $B'_F$ and $Z'_F$ have the same significance as defined in $A_F$, $B_F$ and $Z_F$ but where the group contains a functional group, the functional group may be protected suitably) with formaldehyde or an equivalent thereto in the presence of a secondary amine, if necessary, while heating. The reaction conditions are similar to those used to react the compounds of formula [4F] with the compounds of formula [3F] described above. Where heating is further required, it is preferred to heat at 30° C. to 200° C. Alternatively, the compounds of formula [2F] may be readily prepared by producing the compounds of formula [1F] through Mannich reaction, oxidizing the nitrogen of the compounds [1F] with an oxidizing agent or alkylating the same with an alkylating agent to convert into the quaternary salt and then heating, if necessary. The oxidizing agent suitable for use in the oxidation includes an organic peracid such as m-chloroperbenzoic acid, etc., hydrogen peroxide, an organic peroxide, etc. The alkylating agent includes methyl iodide, dimethyl sulfate, ethyl iodide, etc. Heating conditions optionally performed following the oxidation or alkylation are similar to those described above.

In the compounds of formula [4F] wherein $A'_F$ is, for example, an aliphatic hydrocarbon group, regioselectivity in the Mannich reaction might sometimes cause a problem. In that case, the problem may be avoided as follows. For example, known 3-acetylbutyrolactone (Bull. Chem. Soc. Jpn., 32, 1282 (1959)) is kept under acidic or basic conditions to prepare 3-methylidene-4-oxo-1-n-pentaneoic acid. Reactants used for the reaction are an inorganic base such as sodium hydroxide, etc., an organic base such as triethylamine, 1,8-diazabicyclo[5.4.0]-undeca-7-ene, etc., an inorganic acid such as hydrochloric acid, sulfuric acid, etc., and an organic acid such as p-toluenesulfonic acid, preferably an organic base such as triethylamine or 1,8-diazabicyclo[5.4.0]-undeca-7-ene and an inorganic acid such as sulfuric acid.

To cope with the regioselectivity problem, other alternatives may be used, such as the process disclosed in J. Chem. Soc. Chem. Commun., 1974, 253 in which highly site-selective reactants for Mannich reaction are used, or the process involving site specific conversion of a ketone to an enolate followed by introduction of an aminomethylene unit into the enolate disclosed in Tetrahedron, 46, 987 (1990).

Some of the compounds of formula [4F] are commercially available as reagents. They are, e.g., 4-phenyl-4-oxobutanoic acid, 4-(4-methylphenyl)-4-oxobutanoic acid, 4-(4-methoxyphenyl)-4-oxobutanoic acid, 2-methyl-4-oxo-4-phenylbutyric acid, 4-benzoylbutyric acid, etc. The compounds of formula [4F] wherein $A_F$ is, e.g., a benzene ring or a benzene ring substituted with an electron donating group may also be synthesized by Friedel-Crafts acylation with maleic anhydride in the presence of a Lewis acid catalyst such as aluminum chloride (Org. Synthesis, Coll. III, 109 (1955)).

The compounds of formula [4F], wherein $A_F$ is other than the groups described above, or reduction products thereof (alcohol products) may be prepared by a modification of Reformatsky reaction, which involves reacting the corresponding acid halide of $A_F$ or aldehyde with ethyl γ-iodopropionate in the presence of zinc (J. Am. Chem. Soc., 109, 8056 (1987)). The reduction product may be oxidized to the corresponding ketone in a conventional manner to give the compounds of formula [4F]. Alternatively, the compounds of formula [4F] may be prepared by reacting the corresponding aldehyde of $A_F$ with acrylic acid derivatives in the presence of a catalyst such as sodium cyanide or 3-benzyl-5-(2-hydroxyethyl)-4-methylthiazolium chloride, as described in Chem. Ber., 109, Section 289, 541 (1976). Furthermore, the compounds of formula [4F] may be prepared by subjecting the corresponding methyl ketone of $A_F$ to Aldol condensation with glyoxylic acid accompanying dehydration in vacuo with heating, and reducing the resulting carbon-carbon double bond in a conventional manner using, e.g., zinc powders-acetic acid, as described in J. Med. Chem., 15, 918 (1972).

The compounds of formula [5F] can be prepared, for example, in accordance with the following process.

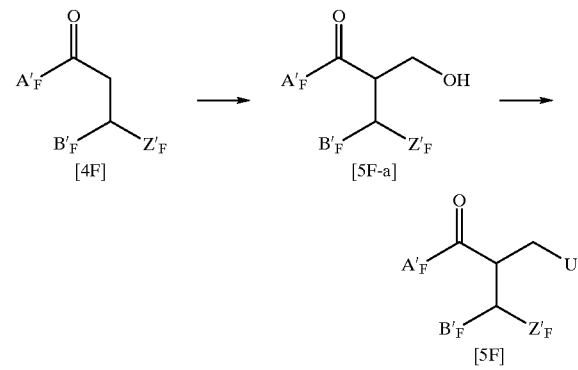

wherein $A'_F$, $B'_F$ and $Z'_F$ have the same significance as defined in $A_F$, $B_F$ and $Z_F$ but where the group contains a functional group, the functional group may be protected suitably, and U is a leaving group and the carbonyl at the 1-position may be suitably protected.

The compounds of formula (5F-a) may be prepared from the compounds of formula [4F] by a modification of the known processes for preparing a βhydroxyketone, e.g., by reacting the compounds of formula [4F] with formaldehyde under basic conditions, or by reacting silyl-enol derivatives of the compounds of formula [4F] with formaldehyde under acidic conditions. The compounds of formula [5F] may be readily prepared by reacting the thus obtained compounds of formula (5F-a) with a sulfonyl chloride such as p-toluenesulfonyl chloride, if necessary, in the presence of a base, or by reacting with a halogenating reagent for the hydroxy, such as thionyl chloride, a triphenylphosphine-halogenating agent, a triphenylphosphine-diethyl azodicarboxylate-halogenating agent, etc. in a conventional manner. The thus prepared compounds of formula [5F] may be used without isolating the same for the next reaction.

Compounds (a) and (b) described above are the same as Compounds (c) and (d) in the preparation of the compounds of formula [1B] and may be prepared by the processes described for these compounds.

Hereinafter the pharmaceutical properties of the compounds of the present invention will be described in more detail.

The compounds of the present invention and pharmacologically acceptable salts thereof are found to exhibit a potent neuron differentiation promoting activity. Therefore, the compositions comprising as the active ingredient the compounds of the present invention and pharmacologically acceptable salts thereof are effective for promoting or accelerating the neuron differentiation and can thus be used as medicaments for the treatment of central and peripheral nervous disorders.

Where the compounds of the present invention and pharmacologically acceptable salts thereof are used as the neuron differentiation accelerator, the composition may be used in the form of pharmaceutical preparations such as injection, drop, granules, tablets, granulates, fine particles, powders, capsules, liquid, inhalation, suppositories, eye lotion, plaster, ointment, spray, etc., singly or in combination with pharmaceutically acceptable additives such as carriers, excipient, diluents, dissolution aids, etc. The route for administration may be chosen from oral and parenteral administration (systemic and local administration).

The compound of the present invention or a pharmacologically acceptable salt thereof contained in the pharmaceutical composition varies depending upon the form of the preparation but preferably in an amount of 0.1 to 100 wt %. A dose is determined depending upon =age, sex, body weight, conditions of the patient and purpose of treatment, etc., but generally in a range of approximately 0.001 to 5000 mg/kg/day.

Next, the processes for preparing the compounds of the present invention or pharmacologically acceptable salts thereof and the neuron differentiation accelerating activity will be described below in more detail with reference to the following Examples.

EXAMPLE 1

Preparation of 4-[(2R)-(2-acetylamino-2-carboxy) ethylthio]methyl-3-oxo-1-cyclopentanecarboxylic Acid (Compound 1A)

(1) Preparation of 1,1-dimethoxy- 2,4-bis (methoxycarbonyl)cyclopentane (Compound 1A-B) and 1,1-dimethoxy-2,3-bis(methoxycarbonyl)cyclopentane (Compound 1A-b)

2,4-Bis(methoxycarbonyl)cyclopentanone (Compound 1A-A) is prepared as a mixture with 2,3-bis (methoxycarbonyl)cyclopentanone (Compound 1-Aa), e.g., by the process described in J. Org. Chem., 47, 2379 (1982). By converting the mixture into 2,4-bis(hydroxymethyl) cyclopentanone and 2,3-bis(hydroxymethyl) cyclopentanone, the two compounds can be separated from each other by silica gel column chromatography.

To a mixture (6970 mg, 34.85 mmols) of Compound (1A-A) and Compound (1A-a) were added absolute methanol (35 ml), methyl orthoformate (4.74 ml) and p-toluenesulfonic acid monohydrate (165 mg). The mixture was stirred at room temperature for 18 hours. After toluene (60 ml) was added to the reaction mixture, washing was conducted twice with saturated sodiumhydrogen carbonate (25 ml). The toluene layer was washed with saturated sodium chloride aqueous solution (50 ml) and concentrated to give a mixture (8334 mg, yield: 97.2%) of 1,1-dimethoxy-2,4-bis-(methoxycarbonyl)cyclopentane (Compound 1A-B) and 1,1-dimethoxy-2,3-bis(methoxycarbonyl)cyclopentane (Compound 1A-b).

(2) Preparation of 2,4-bis (hydroxymethyl)cyclopentanone (Compound 1A-C)

A solution of a mixture (9676 mg, 39.32 mmols) of Compound (1A-B) and Compound (1A-b) in absolute ether (10 ml) was dropwise added to a suspension of lithium aluminum hydride (3120 mg) in absolute ether (43 ml) over an hour under ice cooling. After stirring for 30 minutes, water (3.12 ml), 15% sodium hydroxide (3.12 ml) and water (3.12 ml) were further added to the mixture followed by stirring for further 30 minutes. Anhydrous sodium sulfate (10 g), ether (55 ml) and HAIFURO SUPER CEL (6 g) were added to the mixture. After stirring for 30 minutes, the mixture was filtered. The residue was further extracted twice with ether (100 ml). All of the ethereal fractions were collected and concentrated. The resulting residue was dissolved in acetone (37 ml). Water (1.85 ml) and 1 N hydrochloric acid (1.85 ml) were added to the solution. The mixture was stirred for 30 minutes at room temperature. After 1 N sodium hydroxide (1.85 ml) was added to the reaction mixture, silica gel (18 g) was added thereto followed by concentration. The residue was purified by silica gel column chromatography (550 ml, dichloromethane:methanol=30:1) to give Compound (1A-C, 1310 mg, yield: 23.1%) and Compound (1A-c, 1539 mg, yield: 27.0%).

TLC (silica gel:chloroform:methanol=10:1) Compound (1A-C, Rf=0.42), Compound (1A-c, Rf=0.45)

(3) Preparation of 2,4-bis(acetoxymethyl)cyclopentanone (Compound 1A-D)

To Compound (1A-C) (1130 mg, 7.847 mmols) were added anhydrous pyridine (4 ml) and absolute acetic acid (4 ml). The mixture was stirred at room temperature for an hour. After the reaction mixture was concentrated, the residue was purified by silica gel column chromatography (150 ml, hexane:ethyl acetate=1:1) to give Compound (1A-D) (1598 mg, yield: 89.2%).

1H-NMR (200 MHz, CDCl3) δ: 1.45–1.70 (1H, m), 1.85–2.12 (7H, m), 2.15–2.78 (4H, m), 4.00–4.39 (4H, m); MS (FAB, POS) m/z: 229 (M+H)+.

(4) Preparation of 4-acetoxymethyl-2-{(2,3-dihydroxy) propylthio}methylcyclopentanone (Compound 1A-E)

Methanol (5 ml), acetone (30 ml) and 1 N sodium hydroxide (6.1 ml) were added to Compound (1A-D) (1.4 g, 133 mmols) and alpha-thioglycerine (0.66 g, 133 mmols). The mixture was stirred for 45 minutes. After the pH was adjusted to 7.0 by adding 1 N hydrochloric acid to the reaction solution, the mixture was concentrated. Saturated sodium chloride aqueous solution (30 ml) was added to the residue. The mixture was extracted 5 times with dichloromethane (30 ml). The dichloromethane layer was dried over anhydrous sodium sulfate followed by concentration. The thus obtained residue was purified by silica gel column chromatography (300 ml, chloroform:methanol=40:1 to 10:1) to give Compound (1A-E) (1.5 g, yield: 88.23%).

1H-NMR (200 MHz, CDCl3) δ: 1.50 (1H, m), 1.78 –2.28 (5H, m), 2.35–2.80 (8H, m), 2.85–3.08 (1H, m), 3.50–3.63 (1H, m), 3.68–3.90 (2H, m), 3.98–4.20 (2H, m); MS (FAB, POS) m/z: 277 (M+H)+.

(5) Preparation of 4-acetoxymethyl-2-{(2,3-O-isopropylidene)propylthio}methylcyclopentanone (Compound 1A-F)

To Compound (1A-E) (1.6 g, 5.78 mmols) were added acetone (15 ml), dimethoxypropane (1.81 g, 17.34 mmols) and p-toluenesulfonic acid monohydrate (0.11 g, 0.578 mmols). The mixture was stirred at room temperature for 2 hours. After water (20 ml) and ethyl acetate (80 ml) were added to the reaction mixture, the pH of the aqueous phase was adjusted to 7.0 with saturated hydrogensodium carbonate. Sodium chloride was added to the aqueous phase for separation until it was saturated. The aqueous phase was further extracted twice with ethyl acetate (50 ml). The ethyl acetate layers were collected and dried over anhydrous sodium sulfate. The residue obtained after concentration was purified by silica gel column chromatography (300 ml, hexane:ethyl acetate=3:1) to give Compound (1A-F) (1.6 g, yield: 87.4%).

1H-NMR (200 MHz, CDCl3) δ: 1.35 (1H, s), 1.42 (3H, s), 1.85–2.26 (5H, m), 2.30–2.85 (7H, m), 2.95–3.12 (1H, m), 3.70 (1H, dd, J=6.27 Hz, 8.22 HZ), 3.98–4.32 (4H, m); MS (FAB, POS) m/z: 317 (M+H)+.

(6) Preparation of 4-hydroxymethyl-2-[(2,3-O-isopropylidene)propylthio]methylcyclopentanone (Compound 1A-G)

To Compound (1A-F) (1.6 g, 5.05 mmols) were added methanol (20 ml) and water (5 ml). Under ice cooling 1 N sodium hydroxide (3.2 ml, 3.20 mmols) was added to the mixture followed by stirring for an hour. After the pH was adjusted to 7.0 with 1 N hydrochloric acid, the reaction solution was concentrated and saturated sodium chloride aqueous solution (15 ml) was added to the residue. After extracting 3 times with ethyl acetate (30 ml), the ethyl acetate layer was dried over anhydrous sodium sulfate and then concentrated to dryness. The residue was purified by silica gel column chromatography (250 ml, ethyl acetate:hexane=2:1) to give Compound (1A-G) (1.0 g, yield: 72.4%).

1H-NMR (200 MHz, CDCl3) δ: 1.35 (3H, s), 1.42 (31H, s), 1.61–1.73 (1H, m), 1.95–2.85 (9H, m), 3.00 (1H, m), 3.60–3.78 (3H, m), 4.05–4.12 (1H, m), 4.18–4.33 (1, m); MS (FAB, POS) m/z: 275 (M+H)+.

(7) Preparation of 4-hydroxymethyl-2-[(2,3-O-isopropylidene)propylsulfonyl]methylcyclopentanone (Compound 1A-H)

Compound (1A-G) (1.0 g, 3.64 mmols) was dissolved in dichloromethane (25 ml). Under ice cooling, m-chloroperbenzoic acid (1.74 g, purity 80%, 8.04 mmols) was added to the solution by 4 portions. After stirring for 1.5 hours and filtering subsequently, water (10 ml), 20% sodium hydrogen sulfite (1 ml) and saturated sodium hydrogen carbonate (2 ml) were added to the filtrate. The mixture was stirred at room temperature for 15 minutes. After saturated sodium chloride aqueous solution (20 ml) was added to the reaction solution, the mixture was separated. The aqueous phase was further extracted twice with dichloromethane (25 ml). The dichloromethane layers were collected and dried over anhydrous sodium sulfate and then concentrated. The residue was purified by silica gel column chromatography (300 ml, ethyl acetate:hexane=3:1) to give Compound (1A-H) (1.0 g, yield: 89.2%).

(8) Preparation of 4-[(2,3-O-isopropylidene)propylsulfonyl]methyl-3-oxo-1-cyclopentanecarboxylic acid (Compound a)

Compound (1A-H) (1.0 g, 3.26 mmols) was dissolved in acetone (55 ml). While stirring, Jones reagent (2.5 ml) was dropwise added to the solution over 15 minutes while chilling. The reaction solution was stirred for 20 minutes, during which the reaction solution retained orange color. 2-Propanol (1 ml) was added to the reaction mixture. After stirring for 5 minutes, the mixture was concentrated. To the residue were added water (20 ml) and saturated sodium chloride aqueous solution (30 ml). The resulting mixture was extracted 8 times with dichloromethane (40 ml). The dichloromethane layer was washed with saturated sodium chloride aqueous solution (200 ml), dried over anhydrous sodium sulfate and then concentrated. The residue was purified by silica gel column chromatography (100 ml, chloroform:methanol=10:1 to 4 1) to give Compound (a) (0.69 g, yield: 66.3%).

1H-NMR (200 MHz, CDCl3) δ: 1.37 (3H, s), 1.44 (1.5H, s), 1.45 (1.5H, s), 1.78–2.31 (1H, m), 2.32–3.51 (8H, m), 3.75 (2H, m), 4.20 (1H, dd, J=8.67 Hz, 8.71 Hz), 4.60 (1H, m), 6.80 (1H, brs); MS (FAB, POS) m/z: 321 (M+H)+.

(9) Preparation of 4-[(2R)-(2-acetylamino-2-carboxy)ethylthio]methyl-3-oxo-1-cyclopentanecarboxylic acid (Compound 1A)

Compound (a) (170 mg, 0.53 mmols) was dissolved in acetone (7 ml). To the solution were added N-acetyl-L-cysteine (87 mg, 0.53 mmols) and 1 N sodium hydroxide (1.5 ml). The mixture was stirred at room temperature for 2 hours. After the pH was adjusted to 6.8 by adding 1N hydrochloric acid to the reaction mixture, the mixture was concentrated. The residue was purified on QAE-Sephadex (200 ml, C1 type, 0.05M–0.4 M sodium chloride aqueous solution, 700 ml each, gradient elution) to obtain the objective fraction. After the fraction was concentrated, methanol (3 ml) was added to filter insoluble salts off. The filtrate was purified by Sephadex LH-20 (100 ml, 80% hydrated methanol) to give Compound (1A) sodium salt (85 mg, yield: 46.1%).

1H-NMR (200 MHz, CDCl3) δ: 108 (1H, m), 2.06 (3H, s), 2.10–2.80 (5H, m), 2.81–3.16 (4H, m), 4.36 (1H, dd, J=44.4 Hz, 8.1 Hz); MS (FAB, POS) m/z: 348 (M+H)+.

EXAMPLE 2

Preparation of 4-[(2R)-(2-acetylamino-2-methoxycarbonyl)ethylthio]methyl-3-oxo-1-cyclopentanecarboxylic Acid (Compound 2A)

Acetone (6 ml), N-acetyl-L-cysteine methyl ester (110.6 mg, 0.624 mmols), water (2 ml) and 1 N sodium hydroxide (1.25 ml) were added to Compound (a) (200 mg, 0.624 mmols). The mixture was stirred at room temperature for 2 hours. After the pH was adjusted to 6.8 by adding 1N hydrochloric acid to the reaction mixture, the mixture was concentrated. The residue was purified on QAE-Sephadex (200 ml, C1 type, 0.05M–0.3 M sodium chloride aqueous solution, 700 ml each, gradient elution) to obtain the objective fraction. After the fraction was concentrated, methanol (3 ml) was added to filter insoluble salts off. The filtrate was purified by Sephadex LH-20 (100 ml, 80% hydrated methanol) to give Compound (2A) sodium salt (140 mg, yield: 66.6%).

1H-NMR (200 MHz, CDCl3) δ: 1.80 (1H, m), 2.06 (3H, s), 2.08–2.80 (5H, m), 2.81–3.18 (4H, m), 3.79 (3H, s), 4.64 (1H, m); MS (FAB, POS) m/z: 340 (M+H)+.

EXAMPLE 3

Preparation of (2RS,4S)-2-[(2R)-(2-acetylamino-2-carboxy)ethylthio]methyl-4-hydroxy-1-cyclopentanone (Compound 3A)

(1) Preparation of (4R)-2-[(2R)-(2-acetylamino-2-methoxycarbonyl)ethylthio]methyl-4-tert-butyldimethylsiloxy-2-cyclopenten-1-one (Compound 3A-b)

(4R)-2-(N,N-diethylamino)methyl-4-tert-butyldimethylsiloxy-2-cyclopenten-1-one (Compound 3A-a) (370 mg, 1.24 mmols) was dissolved in methanol (4 ml). To the solution was added iodomethane (0.16 ml, 2.48 mmols) followed by stirring at room temperature for 2 hours. After the reaction solution was concentrated, methanol (3 ml) and N-acetyl-L-cysteine methyl ester (220 mg, 1.24 mmols) were added to the residue. The mixture was stirred at room temperature for 1.5 hours. After the reaction solution was concentrated, the residue was purified by silica gel column chromatography (60 ml, dichloromethane:methanol=40:1) to give Compound (3A-b) (378 mg, yield: 75.7%).

1H-NMR (200 MHz, CDCl3) δ: 0.12 (3H, s), 0.14 (3H, s), 0.92 (9H, s), 2.07 (3H, s), 2.31 (1H, dd, J=2, 11 Hz, 18.31 Hz) 2.80 (1H, dd, J=5.99 Hz, 18.31 Hz), 2.99 (2H, m), 3.30 (2H, m), 3.78 (3H, s), 4.86 (1H, m), 4.92 (1H, m), 6.56 (1H, d, J=7.69 Hz), 7.29 (1H, m); MS (FAB, POS) m/z: 402 (M+H)+.

(2) Preparation of (4R)-2-[(2R)-(2-acetylamino-2-methoxycarbonyl)ethylthio]methyl-4-hydroxy-2-cyclopenten-1-one (Compound 3A-c)

Methanol (4 ml), water (0.2 ml) and Dowex 50 (H+ type, 300 mg) were added to Compound (3A-b) (64 mg, 0.16 mmol). The mixture was stirred at room temperature for 20 hours. The reaction mixture was concentrated and the residue was purified by silica gel column chromatography (20 ml, dichloromethane:methanol=20:1) to give Compound (3A-c) (33.6 mg, yield: 73.6%); MS (FAB, POS) m/z: 288 (M+H)+.

(3) Preparation of (4R)-2-[(2R)-(2-acetylamino-2-methoxycarbonyl)ethylsulfonyl]methyl-4-hydroxy-2-cyclopenten-1-one (Compound 3A-d)

Compound (3A-c) (33.6 mg, 0.117 mmol) was dissolved in dichloromethane (3 ml). Under ice cooling, m-chloroperbenzoic acid (purity 80%, 50 mg, 0.23 mmol) was added to the solution. After stirring at room temperature for 2 hours, water (5 ml) and dichloromethane (5 ml) were added to the reaction mixture. Thereafter saturated sodium hydrogen carbonate solution was added to the mixture until the aqueous layer became neutral. Sodium hydrogen sulfite (20% aqueous solution, 5 drops) was added to the mixture for separation. After the dichloromethane layer was concentrated, the residue was purified by silica gel column chromatography (20 ml, dichloromethane:methanol=10:1) to give Compound (3A-d) (36 mg, yield: 96.4%). MS (FAB, POS) m/z: 320 (M+H)+. (4) Preparation of (4S)-2-[(2R)-(2-acetylamino-2-methoxycarbonyl)ethylsulfonyl]methyl-4-hydroxycyclopentan-1-one (Compound c)

To Compound (3A-d) (36 mg, 0.112 mmol) were added ethanol (3 ml), methanol (1.5 ml) and 10% Pd—C (50% wet, 8.8 mg). The mixture was stirred at room temperature for 10 hours in hydrogen atmosphere. The reaction solution was filtered and the filtrate was concentrated to give Compound (c) (36 mg, yield: 100%). MS (FAB, POS) m/z: 322 (M+H)+.

(5) Preparation of (2RS,4R)-2-[(2R)-(2-acetylamino-2-carboxy)ethylthio]methyl-4-hydroxy-1-cyclopentanone (Compound 3A)

Acetone (3 ml), N-acetyl-L-cysteine (24.3 mg, 0.149 mmols), methanol (1.5 ml) and 1 N sodium hydroxide (0.22 ml) were added to Compound (c) (48 mg, 0.149 mmols). The mixture was stirred at room temperature for 1.5 hours. After silica gel (500 mg) was added to the reaction solution, the mixture was concentrated to dryness. The residue was purified by silica gel column chromatography (80 ml, dichloromethane:methanol:acetic acid=5:1:0.1) and concentrated again. The residue was dissolved in water (4 ml). After adjusting the pH to 6.8 with 1N sodium hydroxide, the solution was concentrated to give the sodium salt of Compound (3A) (26.6 mg, yield: 60%).

1H-NMR (200 MHz, D2O) δ: 1.76 (1H, m), 2.00 (3H, s), 2.20 (1H, dd, J=7.13 Hz, 18.9 Hz), 2.30–3.16 (8H, m), 4.40–4.62 (2H, m); MS (ESI, NEG) m/z: 274 (M–H)–.

EXAMPLE 4

(2RS,4S)-2-[(2R)-3-acetylamino-3-[1-{(2S)-methoxycarbonyl}pyrrolidinyl]-3-oxypropylthio]methyl-4-hydroxy-1-cyclopentanone (Compound 4A)

Compound (3) (28.2 mg, 0.1 mmol) and proline methyl ester hydrochloride (16.95 mg) were dissolved in dimethylformamide (3 ml). Under ice cooling, triethylamine (14.1 ul), 1-hydroxy-benzotriazole (16.5 mg, 0.12 mmol) and dicyclohexylcarbodiimide (23.1 mg) were added to the solution. The mixture was stirred at room temperature for 2 hours. The reaction solution was concentrated and the residue was purified by silica gel column chromatography (30 ml, dichloromethane:methanol=10:1) to give Compound (4A) (18.2 mg, yield: 47%).

1H-NMR (200 MHz, CDCl3) δ: 1.85–2.10 (3H, m), 2.00 (3H, s), 2.10–3.13 (10H, m), 3.64–3.90 (5H, m), 4.42–4.70 (2H, m), 4.98 (1H, m), 6.68 (1H, m); MS (FAB, POS) m/z: 387 (M+H)+.

EXAMPLE 5

2-((2R)-(2-acetylamino-2-methoxycarbonyl)ethylthio)methyl-3-oxo-1-indanecarboxylic Acid (Compound 6A)

After 37% formalin (0.088 ml, 1.08 mmol) was added to a mixture of 3-oxo-1-indanecarboxylic acid (191 mg, 1.08 mmol) and piperidine (92.3 mg, 1.08 mmol), the mixture was stirred at room temperature for 3 hours. The reaction solution was concentrated. Ethanol (3 ml) and N-acetyl-L-cysteine methyl ester (80 mg, 0.45 mmol) were added to the residue. The mixture was heated to reflux for 10 minutes and then concentrated in vacuo. The residue was purified by silica gel column chromatography (100 ml, chloroform:methanol:acetic acid=30:1:0.5) to give Compound (6A) (62 mg, yield: 15.7%).

1H-NMR (200 MHz, CDCl3) δ: 2.05–2.12 (3H), 2.63–3.30 (4H, m), 3.42 (1H, m), 3.74–3.81 (3H), 4.21 (1H, d, J=4.4 Hz), 4.89 (1H, m), 6.66–6.80 (1H, NH), 7.25 (1H, brs), 7.41–7.86 (4H, m); MS (FAB, POS) m/z: 366 (M+H)+.

EXAMPLE 6

(1R,2S)-2-[(2R)-{2-acetylamino-3-oxo-3-(1-pyrrolidinyl)}propylthio]methyl-3-oxo-1-cyclopentanecarboxylic Acid (Compound 1B)

(1) (2S,3R)-3-acetoxymethyl-2-[(2RS)-2,3-bis(hydroxy)propylthio]methylcyclopentanone (Compound A-2)

Alpha-thioglycerin (9.558 g, 90.17 mmols) was added to a solution of (2R,3R)-2,3-bis(acetoxymethyl)cyclopentanone (Compound A) (20.56 g, 90.17 mmols) in acetone (178 ml). Then methanol (20 ml) and 1 N sodium hydroxide (90.17 ml) were added to the mixture followed by stirring at room temperature for 40 minutes. After the pH was adjusted to 7.0 by adding 1 N hydrochloric acid to the reaction solution, the mixture was concentrated. The residue obtained was dissolved in methanol (200 ml) and silica gel (120 g) was added to the solution. The mixture was concentrated to dryness, which was then purified by silica gel column chromatography (330 ml, dichloromethane:methanol=25:1 to 5:1) to give Compound (A-2) (22.06 g, yield: 88.63%).

1H-NMR (200 MHz, CD3OD) δ: 1.56–1.79 (1H, m), 2.07 (3H, s), 2.07 (3H, s), 2.10–2.16 (9H, m), 3.50–3.60 (2H, m), 3.66–3.78 (1H, m), 4.21–4.34 (2H, m); MS (FAB, POS) m/z: 277 (M+H)+.

(2) Preparation of (2S,3R)-3-acetoxymethyl-2-[(2RS)-(2,3-O-isopropylidene)propylthio]methylcyclopentanone (Compound A-3)

Compound (A-2) (22.06 g, 79.92 mmols) was dissolved in anhydrous acetone (120 ml). Under ice cooling, p-toluenesulfonic acid monohydrate (1.5 g), dimethoxypropane (29.46 ml, 240 mmols) were added to the solution. The mixture was stirred at room temperature for 30 minutes. After water (150 ml) and ethyl acetate (300 ml) were added to the reaction mixture, the pH of the aqueous phase was adjusted to 7.0 with saturated sodium hydrogen carbonate. The aqueous phase was extracted twice with ethyl acetate (300 ml). The ethyl acetate layer was washed with saturated sodium chloride aqueous solution (160 ml), dried over anhydrous sodium sulfate and concentrated in vacuo to give Compound (A-3) (24.00 g, yield: 95.0%).

1H-NMR (200 MHz, CDCl3) δ: 1.35 (3H, s), 1.42 (3H, s), 1.51–1.76 (1H, m), 2.08 (3H, s), 2.10–2.96 (9H, m), 3.65–3.74 (1H, m), 4.05–4.18 (1H, m), 4.18–4.29 (2H, m); MS (FAB, POS) m/z: 317 (M+H)+.

(3) Preparation of (2S,3R)-3-hydroxymethyl-2-[(2RS)-(2,3-O-isopropylidene)propylthio]methylcyclopentanone (Compound A-4)

Compound (A-3) (25.22 g, 79.81 mmols) was dissolved in methanol (253 ml). Under ice cooling, 1N sodium hydroxide (50 ml) was added to the solution. The mixture was stirred at room temperature for 18 minutes. After the pH of the mixture was adjusted to 5.8 with 1N hydrochloric acid while ice cooling, the mixture was concentrated in vacuo to give the residue. Water (50 ml) was added to the residue and the mixture was extracted 3 times with ethyl acetate (200 ml). The ethyl acetate layer was washed with saturated sodium chloride aqueous solution (100 ml), dried over anhydrous sodium sulfate and concentrated in vacuo. The thus obtained residue was purified by silica gel column chromatography (300 ml, dichloromethane:methanol=30:1) to give Compound (A-4) (18.67 g, yield: 85.3%).

1H-NMR (200 MHz, CDCl3) δ: 1.36 (3H, s), 1.43 (3H, s), 1.58–1.81 (1H, m), 2.00–2.82 (9H, m), 3.02–3.11 (1H, dd, J=3.6 Hz, 13.2 Hz), 3.64–3.73 (1H, m), 3.76–3.91 (2H, m), 4.06–4.34 (2H, m); MS (FAB, POS) m/z: 275 (M+H)+.

(4) Preparation of (2S,3R)-3-hydroxymethyl-2-[(2RS)-(2,3-O-isopropylidene)propylsulfonyl]methylcyclopentanone (Compound A-5)

Compound (A-4) (5.558 g, 20.28 mmol) was dissolved in dichloromethane (55 ml). Under ice cooling, a solution of m-chloroperbenzoic acid (purity 80%, 8.74 g, 40.56 mmols) in dichloromethane (85 ml) was added to the solution. The mixture was stirred at room temperature for an hour. The reaction solution was filtered and to the filtrate, 20% sodium hydrogen sulfite (6.48 ml), saturated sodium carbonate aqueous solution (16.2 ml) and further water (50 ml) were added followed by stirring for 10 minutes. After liquid-liquid separation, the dichloromethane layer was washed with saturated sodium chloride aqueous solution (100 ml), dried over anhydrous sodium sulfate and concentrated in vacuo. The thus obtained residue was purified by silica gel column chromatography (150 ml, hexane:ethyl acetate=1:3) to give Compound (A-5) (5.798 g, yield: 93.4%).

1H-NMR (200 MHz, CDCl3) δ: 1.38 (3H, s), 1.45 (3H, s), 1.68–1.92 (1H, m), 1.99–2.76 (6H, m), 3.10–3.50 (3H, m), 3.70–4.08 (4H, m), 4.10–4.24 (1H, dd, J=6.14 Hz, 7.42 Hz), 4.56–4.68 (1H, m); MS (FAB, POS) m/z: 307 (M+H)+.

(5) Preparation of (1R,2S)-2-[(2RS)-(2,3-O-isopropylidene)propylsulfonyl]methyl-3-oxo-1-cyclopentanecarboxylic acid (Compound C)

Compound (A-5) (5.80 g, 18.94 mmols) was dissolved in acetone (320 ml). While stirring Jones reagent was added to the solution until the reaction solution maintained its orange color. Under ice cooling, 2-propanol was added to the reaction mixture until the reaction solution turned green. The mixture was concentrated in vacuo to remove acetone. To the residue water (120 ml) was added. The mixture was extracted twice with dichloromethane (200 ml). The dichloromethane layer was washed with saturated sodium chloride aqueous solution (80 ml), dried over anhydrous sodium sulfate and then concentrated in vacuo to give Compound (C) (4.59 g, yield: 75.7%).

1H-NMR (200 MHz, CDCl3) δ: 1.37 (3H, s), 1.43 (1.5H, s), 1.47 (1.5H, s), 2.02 (1H, m), 2.22–2.65 (3H, m), 2.94–3.32 (3H, m), 3.32–3.84 (4H, m), 4.19 (1H, m), 4.40 (1H, m), 4.59 (1H, m); MS (ESI, NEG) m/z: 319 (M–H)–.

(6) Preparation of (1R,2S)-2-[(2R)-{2-acetylamino-3-oxo-3-(1-pyrrolidinyl}propylthio]methyl-3-oxo-1-cyclopentanecarboxylic acid (Compound 1B)

Compound (C) (32 mg, 0.1 mmol) was dissolved in acetone (2 ml) and, a solution of (2R)-2-acetylamino-3-oxo-3-(1-pyrrolidinyl)propanethiol (21.6 mg, 0.1 mmol) in acetone (1 ml) was added thereto. The mixture was stirred at room temperature for 2 hours. After 1N hydrochloric acid was added to the reaction solution to adjust the pH to 6.8, the mixture was concentrated. The residue was purified on QAE-Sephadex (Cl type, 110 ml, 0.05M–0.5M NaCl, 300 ml each, gradient elution). The objective fractions were collected. After the pH was adjusted to 2.6, the product was adsorbed onto DIAION-SP207 (10 ml, Nippon Rensui K.K.), then washed with water and eluted with 80% hydrated methanol. After the pH was adjusted to 6.8 with 1N sodium hydroxide, the eluate was concentrated to dryness to give Compound (1B) sodium salt (26 mg, yield: 68.7%).

1H-NMR (200 MHz, D2O) δ: 1.75–2.05 (5H, m), 1.98 (3H, s), 2.06–2.61 (3H, m), 2.62–3.25 (6H, m), 3.28–3.49 (2H, m), 3.52–3.75 (2H, m), 4.69 (1H, t, J=6.88 Hz); MS (ESI, NEG) m/z: 355 (M–Na)–.

EXAMPLE 7

Preparation of (1R,2S)-2-[(2R)-{2-acetylamino-3-(4-morpholinyl)-3-oxo}propylthio]methyl-3-oxo-1-cyclopentanecarboxylic Acid (Compound 2B)

Compound (C) (32 mg, 0.1 mmol) was dissolved in acetone (2 ml) and, a solution of (2R)-2-acetylamino-3-(4-morpholinyl)-3-oxopropanethiol (23.2 mg, 0.1 mmol) in acetone (1 ml) was added thereto. The mixture was stirred at room temperature for 1.5 hours. Purification was made in a manner similar to Example 1 to give Compound (2B) sodium salt (22.4 mg, yield: 56.8%).

1H-NMR (200 MHz, D2O) δ: 1.78–1.98 (1H, m), 1.99 (1H, s), 2.05–2.60 (3H, m), 2.65–3.00 (6H, m), 3.45–3.89 (8H, m), 4.90 (1H, t, J=6.96); MS (FAB, POS) m/z: 395 (M+Na+H)+.

EXAMPLE 8

Preparation of (1R,2S)-2-[(2R)-12-acetylamino-3-oxo-3-(1-piperidinyl)propylthio1methyl-3-oxo-1-cyclopentanecarboxylic Acid Compound 3B)

Compound (C) (32 mg, 0.1 mmol) was dissolved in acetone (2 ml). A solution of (2R)-2-acetylamino-3-(1-piperidinyl)-3-oxopropanethiol (23 mg, 0.1 mmol) in acetone (1 ml) and 1N sodium hydroxide (0.2 ml) were added to the solution. The mixture was stirred at room temperature for 1.5 hours. Purification was made in a manner similar to Example 6 to give the sodium salt (26.0 mg, yield: 66.3%) of Compound (3B).

1H-NMR (200 MHz, D2O) δ: 1.40–1.72 (6H, m), 1.82 (1H, m), 1.98 (3H, s), 2.04–2.60 (3H, m), 2.62–3.20 (4H, m), 3.32–3.70 (4H, m), 4.98 (1H, t, J=7.04 Hz); MS (ESI, NEG) m/z: 369 (M–Na)–.

EXAMPLE 9

Preparation of (1R,2S)-2-[(2R)-({2-carboxy-2-pentafluoropropionylamino ethylthio]methyl-3-oxo-1-cyclopentanecarboxylic Acid (Compound 4B)

Compound (C) (32 mg, 0.1 mmol) was dissolved in acetone (2 ml). A solution of (2R)-2-carboxy-2-pentafluoropripionylaminoethanethiol (25.3 mg, 0.1 mmol) in acetone (1 ml), methanol (1 ml) and 1N sodium hydroxide (0.3 ml) were added to the solution. The mixture was stirred at room temperature for 1.5 hours. Purification was made in a manner similar to Example 1 to give the sodium salt (30.0 mg, yield: 66.5%) of Compound (4B).

1H-NMR (200 MHz, D2O) δ: 1.71–1.98 (1H, m), 2.05–2.60 (3H, m), 2.62–3.25 (6H, m), 4.41 (1H, dd, J=4.19 Hz, 9.24 Hz); MS (ESI, NEG) m/z: 428 (M–Na)–.

EXAMPLE 10

Preparation of trans-2-[(2R)-{2-acetylamino-3-oxo-3-(1-pyrrolidinyl)}propylthio]methyl-3-methoxycarbonyl-1-cyclopentanone (Compound 5B)

(1) Preparation of trans-3-acetoxy-2-[2,3-bis(hydroxy)propylthio]methylcyclopentanone (Compound a-2)

A solution of trans-2,3-bis(acetoxymethyl)cyclopentanone (Compound (a), 18.72 g, 81.8 mmols) in acetone (160 ml) was added to alpha-thioglycerin (8.7 g). The mixture was stirred at room temperature for 20 minutes. The reaction solution was concentrated. The residue obtained was dissolved in methanol and silica gel (100 g) was added thereto followed by concentration. The residue was purified by silica gel column chromatography (300 ml, dichloromethane:methanol=20:1 to 5:1) to give Compound (a-2) (21.88 g, yield: 96.8%).

1H-NMR (200 MHz, CD3OD) δ: 1.56–1.79 (1H, m), 2.07 (3H, s), 2.10–2.96 (9H, m), 3.56–3.60 (2H, m), 3.66–3.78 (1H, m), 4.21–4.34 (2H, m); MS (FAB, POS) m/z: 277 (M+H)+.

(2) Preparation of trans-3-acetoxy-2-[2,3-O-isopropylidene)propylthio]methylcyclopentanone (Compound a-3)

Compound (a-2) (21.9 g, 79.27 mmols) was dissolved in anhydrous acetone (120 ml). Under ice cooling, p-toluenesulfonic acid monohydrate (1.4 g), dimethoxypropane (29.4 ml) were added to the solution. The mixture was stirred at room temperature for 30 minutes. After water (140 ml) and ethyl acetate (280 ml) were added to the reaction mixture, the pH of the aqueous phase was adjusted to 7.0 with saturated sodium hydrogen carbonate. The aqueous phase was extracted twice with ethyl acetate (280 ml). The ethyl acetate layer was washed with saturated sodium chloride aqueous solution (150 ml), dried over anhydrous sodium sulfate and concentrated to give Compound (a-3) (23.34 g, yield: 93.2%).

1H-NMR (200 MHz, CDCl3) δ: 1.35 (3H, 1.42 (3H, s), 1.50–1.76 (1H, m), 2.08 (3H, m), 2.10–2.96 (9H, m), 3.65–3.74 (1H, m), 4.05–4.18 (2H, m), 4.18–4.29 (2H, m); MS (FAB, POS) m/z: 317 (M+H)+.

(3) Preparation of trans-3-hydroxymethyl-2-[2,3-O-isopropylidene)propylthio]methylcyclopentanone (Compound a-4)

Compound (a-3) (1097 mg, 3.47 mmols) was dissolved in methanol (200 ml) and under ice cooling, 1 N sodium hydroxide (3.47 ml) was added to the solution. The mixture was stirred at room temperature for 15 minutes. After the pH was adjusted to 7.0 with 1N hydrochloric acid while ice cooling, the mixture was concentrated. Water (3 ml) was added to the residue obtained followed by extracting 3 times with ethyl acetate (15 ml). The ethyl acetate layer was washed with saturated sodium chloride aqueous solution (10 ml), dried over anhydrous sodium sulfate and then concentrated. The obtained residue was purified by silica gel column chromatography (50 ml, chloroform methanol=30:1) to give Compound (a-4) (739 mg, yield: 77.5%).

1H-NMR (200 MHz, CDCl3) δ: 1.35 (3H, s), 1.43 (3H, s), 1.58–1.81 (1H, m), 2.00–2.81 (9H, m), 3.02–3.11 (1H, dd, J=3.5 Hz, 13.2 Hz), 3.64–3.73 (1H, m), 3.76–3.91 (2H, m), 4.06–4.34 (1H, m); MS (FAB, POS) m/z: 275 (M+H)+.

(4) Preparation of trans-3-hydroxymethyl-2-[2,3-O-isopropylidene propylsulfonyl 1methylcyclopenta none (Compound a-5)

Compound (a-4) (5140 mg, 18.76 mmol) was dissolved in dichloromethane (50 ml). Under ice cooling, a solution of m-chloroperbenzoic acid (8093 mg, purity 80%, 37.32 mmols) in dichloromethane (80 ml) was added to the solution. The mixture was stirred at room temperature for 2 hours. The reaction solution was filtered and to the filtrate, 20% sodium hydrogen sulfite (6 ml), saturated sodium carbonate aqueous solution (6 ml) and further water (50 ml) were added followed by stirring. After liquid-liquid separation, the dichloromethane layer was washed with saturated sodium chloride aqueous solution (30 ml), dried over anhydrous sodium sulfate and concentrated. The thus obtained residue was purified by silica gel column chromatography (160 ml, hexane:ethyl acetate=1:3) to give Compound (a-5) (4610 mg, yield: 80.3%).

1H-NMR (200 MHz, CDCl3) δ: 1.37 (3H, s), 1.46 (3H, s), 1.73–1.92 (1H, m), 1.98–2.73 (6H, m), 3.10–3.49 (3H, m), 3.68–4.08 (4H, m), 4.16–4.24 (1H, dd, J=6.14 Hz, 7.42 Hz), 4.56–4.68 (1H, m); MS (FAB, POS) m/z: 307 (M+H)+.

(5) Preparation of trans-2-[(2,3-O-isopropylidenelpropylsulfonyl]methyl-3-oxo-1-cyclopentanecarboxylic acid (Compound c]

Compound (a-5) (2630 mg, 8.59 mmols) was dissolved in acetone (150 ml). While stirring Jones reagent was added to the solution until the reaction solution turned orange. Under ice cooling, 2-propanol was added to the reaction mixture until the reaction solution turned green. The mixture was concentrated and water (60 ml) was added to the residue. The mixture was extracted 3 times with dichloromethane (100 ml). The dichloromethane layer was washed with saturated sodium chloride aqueous solution (40 ml), dried over anhydrous sodium sulfate and then concentrated to give Compound (c) (1948 mg, yield: 70.8%).

1H-NMR (200 MHz, CDCl3) δ: 1.37 (3H, s), 1.43 (1.5H, s), 1.47 (1.5H, s), 2.02 (1H, m), 2.22–2.65 (3H, m), 2.94–3.32 (3H, m), 3.32–3.84 (4H, m), 4.19 (1H, m), 4.40 (1H, m), 4.59 (1H, m); MS (ESI, NEG) m/z: 319 (M−H)−.

(6) Preparation of trans-2-[(2R)-{2-acetylamino-3-oxo-3-(1-pyrrolidinyl)}propylthio]methyl-3-methoxycarbonyl-1-cyclopentanone (Compound 5B)

Compound (c) (32 mg, 0.1 mmol), (2R)-2-acetylamino-3-oxo-3-(1-pyrrolidinyl)propanethiol (21.6 mg, 0.1 mmol) and 1N sodium hydroxide (0.2 ml) are reacted and purified in a manner similar to Example 1 to give sodium trans-2-[(2R)-{2-acetylamino-3-oxo-3-(1-pyrrolidinyl)}ethylthio]methyl-3-oxo-1-cyclopentanecarboxylate. The product was dissolved in DMF (3 ml) and methyl iodide (20 ul) was added thereto followed by stirring at room temperature for 35 minutes. The reaction solution was concentrated to dryness. The residue was purified by silica gel column chromatography (20 ml, dichloromethane:methanol=25:1) to give Compound (5B) (18 mg, yield: 48.6%).

1H-NMR (200 MHz, CDCl3) δ: 1.80–2.10 (5H, m), 2.00 (3H, s), 2.10–2.60 (3H, m), 2.68–3.20 (6H, m), 3.38–3.70 (4H, m), 3.75 (3H, s), 4.90 (1H, m), 6.58 (1H, d, J=8.34 Hz); MS (FAB, POS) m/z: 371 (M+H)+.

EXAMPLE 11

Preparation of trans-2-[(2R)-[2-acetylamino-3-{1-((2S)-2-methoxycarbonylpyrrolidinyl)}-3-oxo]propylthio]methyl-3-oxo-1-cyclopentanecarboxylic Acid (Compound 6B)

Compound (c) (53 mg, 0.165 mmol) and (2R)-2-acetylamino-3-[1-{(2S)-2-methoxycarbonyl]pyrrolidinyl}-3-oxopropanethiol (45.3 mg, 0.165 mmol) were dissolved in acetone (3 ml). Methanol (1 ml) and 1N sodium hydroxide (0.33 ml) were added to the solution. The mixture was stirred at room temperature for 1.5 hours. After 1N hydrochloric acid was added to the reaction mixture to adjust the pH to 2.5, the mixture was concentrated to dryness. The residue was purified by silica gel column chromatography (25 ml, dichloromethane:methanol=10:1) to give Compound (6B) (40.3 mg, yield: 58.9%).

1H-NMR (200 MHz, CDCl3) δ: 1.80–2.55 (8H, m), 2.01–2.02 (3H, sx2), 2.56–3.42 (6H, m), 3.62–4.00 (5H, m), 4.50 (1H, m), 4.75–5.19 (1H, m), 7,207.52 (1H, m), 7.80 (1H, brs); MS (ESI, NEG) m/z: 414 (M–H)–.

EXAMPLE 12

Preparation of trans-2-[(2R)-[2-acetylamino-3-{1-((2S)-2-methoxycarbonylazetidinyl)}-3-oxo] propylthio]methyl-3-oxo-1-cyclopentanecarboxylic Acid (Compound 7B)

Compound (c) (92 mg, 0.288 mmol) and (2R)-2-acetylamino-3-[1-{(2S)-2-methoxycarbonyl]azetidinyl}-3-oxopropanethiol (75.0 mg, 0.288 mmol) were dissolved in acetone (3 ml). Methanol (1 ml) and 1N sodium hydroxide (0.58 ml) were added to the solution. The mixture was stirred at room temperature for 1.5 hours. After 1N hydrochloric acid was added to the reaction mixture to adjust the pH to 2.5, the mixture was concentrated to dryness. The residue was purified by silica gel column chromatography (25 ml, dichloromethane:methanol=10:1) to give Compound (7B) (43.0 mg, yield: 373 mg).

1H-NMR (200 MHz, CDCl3) δ: 2.00 (3H, sx2), 2.08–3.60 (12H, m), 3.76–3.84 (3H, sx2), 3.99–4.55 (2H, m), 4.60–5.35 (2H, m), 7.12–7.50 (1H, m), 7.90–8.60 (1H, brs); MS (ESI, NEG) m/z: 399 (M–H)–.

EXAMPLE 13

Preparation of trans-2-[(2R)-(2-carboxy-2-pentafluoropropionylamino ethylthio]methyl-3-hydroxymethyl-1-cyclopentanone (Compound 8B)

Compound (c) (45.6 mg, 0.2 mmol) was dissolved in acetone (4 ml). (2R)-2-carboxyl-2-pentafluoro-propionylaminoethanethiol (50.6 mg, 0.2 mmol) in methanol (1.5 ml) and 1N sodium hydroxide (0.8 ml) were added to the solution. The mixture was stirred at room temperature for an hour. After 1N hydrochloric acid was added to the reaction mixture to adjust the pH to 2.5, the mixture was concentrated to dryness. The residue was purified in a manner similar to Example 1 to give Compound (8B) (71 mg, yield: 83.1%).

1H-NMR (200 MHz, D2O) δ: 1.50–1.76 (1H, m), 2.20–2.65 (5H, m), 2.70–3.00 (3H, m), 3.50–3.90 (2H, m), 4.43 (1H, m); MS (FAB, POS) m/z: 416 (M+H)+.

EXAMPLE 14

Preparation of trans-2-[(11-acetylamino-11-carboxy undecylthio]methyl-3-oxo-1-cyclopentanecarboxylic Acid (Compound 9B)
(1) Preparation of 1-acetylamino-11-benzyloxy-1,1-diethoxycarbonylundecane (Compound r-2)

Anhydrous ethanol (10.5 ml) and diethylacetamide malonate (2661 mg, 12.25 mmols) were added to sodium ethoxide (834 mg, 12.25 mmols). After stirring for 10 minutes, 1-benzyloxy-10-iododecane (Compound q-1) (2661 mg, 12.25 mmols) was added to the mixture. The mixture was heated to reflux for 4 hours and concentrated in vacuo. Chloroform (200 ml) and water (100 ml) were added to the residue for separation. The organic layer was washed with saturated sodium chloride aqueous solution (100 ml), dried over anhydrous sodium sulfate and then concentrated. The residue was purified by silica gel column chromatography (300 ml, hexane:ethyl acetate=4:1) to give Compound (r-2) (5080 mg, yield: 89.7%).

1H-NMR (200 MHz, CDCl3) δ: 1.05–1.42 (18H, m), 1.60 (4H, m), 2.02 (3H, s), 2.30 (2H, m), 3.48 (2H, t, J=6.64 Hz), 4.26 (4H, q, J=7.08 Hz), 4.50 (2H, s), 6.78 (1H, brs), 7.30 (5H, m)
(2) Preparation of 1-acetylamino-1,1-diethoxy-carbonyl-11-hydroxyundecane (Compound r-3)

Compound (r-2) (5090 mg, 10.99 mmols) was dissolved in ethanol (132 ml) and 10% Pd—C (50% wet, 1100 mg) was added to the solution. The mixture was stirred at room temperature for 3 hours in hydrogen atmosphere. The reaction solution was filtered and the filtrate was concentrated to give Compound (r-3) (3760 mg, yield: 91.7%).

MS (FAB, POS) m/z: 374 (M+H)+.
(3) Preparation of 1-acetylamino-1-carboxy-11-hydroxyundecane (Compound r-4)

Compound (r-3) (3760 mg, 10.08 mmols) was dissolved in ethanol (6 ml). After the pH was adjusted to 2.0 with 1N hydrochloric acid, the mixture was heated to reflux for 8 hours, during which the pH was maintained at 2.0 by adding 1N hydrochloric acid. The reaction solution was cooled to precipitate colorless crystals. The crystals were filtered to give Compound (r-4) (1341 mg, yield: 48.7%).

MS (FAB, POS) m/z: 274 (M+H)+.
(4) Preparation of 1-acetylamino-11-acetylthio-1-methoxycarbonylundecane (Compound r-5)

Compound (r-4) (176 mg, 0.64 mmol) was dissolved in methanol (2 ml) and TMS-diazomethane was added thereto. After reacting them for 15 minutes, the mixture was concentrated. The residue was added to a solution of 2-fluoro-1-methylpyridinium p-toluenesulfonate (190 mg, 0.637 mmol) in benzene acetone (1:1, 3 ml), and triethylamine (88.6 ul) was further added thereto. The mixture was stirred at 30° C. for 2 hours. Thioacetic acid (45.5 ul) and triethylamine (88.6 ul) were added to the reaction solution. The mixture was heated to reflux for 2 hours. After the reaction solution was concentrated, dichloromethane (10 ml) and water (5 ml) were added to the residue for liquid separation. The aqueous layer was extracted twice with dichloromethane (10 ml). The dichloromethane layers were collected, dried over anhydrous sodium sulfate and then concentrated. The obtained residue was purified by silica gel column chromatography (25 ml, dichloromethane) to give Compound (r-5) (222 mg, yield: 100%).

1H-NMR (200 MHz, CDCl3) δ: 1.30 (15H, m), 1.47–1.96 (5H, m), 2.04 (3H, s), 2.33 (3H, s), 2.89 (2H, t, J=7.04 Hz), 3.76 (3H, s), 4.61 (1H, m), 6.02 (1H, d, J=7.69 Hz)
(5) Preparation of 1-acetylamino-1-carboxy-11-mercaptoundecane (Compound r)

Compound (r-5) (222 mg, 0.64 mmol) was dissolved in methanol (3 ml) and 1N hydrochloric acid (1.3 ml) was added to the solution followed by stirring at room temperature for 2 hours. After the pH was adjusted to 3.0 with 1N hydrochloric acid, the mixture was concentrated. The residue obtained was purified by silica gel column chromatography (20 ml, dichloromethane:methanol=15:1) to give Compound (r) (123 mg, yield: 66.9%).

MS (ESI, NEG) m/z: 288 (M–H)–.
(6) Preparation of trans-2-[(11-acetylamino-11-carboxy) undecylthio]methyl-3-oxo-1-cyclopentanecarboxylic acid (Compound 9B)

Compound (r) (57.8 mg, 0.2 mmol) and trans-2-[(2RS)-(2,3-O-isopropylidene)propylsulfonyl]methyl-3-oxo-1-cyclopentanecarboxylic acid (Compound c) (64 mg, 0.2 mmol) were dissolved in acetone (3 ml). After 1N sodium hydroxide (0.6 ml) was added to the solution, the mixture was stirred at room temperature for 1.5 hours. The pH was then adjusted to 6.8 with 1N hydrochloric acid. The mixture was concentrated and the residue obtained was purified by QAE-Sephadex. The pH was again adjusted to 6.8. The product was adsorbed to activated carbon (12 ml), washed with water and eluted with 80% hydrated methanol. The eluate was concentrated to give the sodium salt of Compound (9B) (28.9 mg, yield: 32.7%).

1H-NMR (200 MHz) δ: 1.15–1.41 (16H, m), 1.45–1.98 (5H, m), 1.99 (3H, s), 2.10–2.65 (5H, m), 2.71–3.00 (4H, m), 4.08 (1H, dd, J=4.68, 8.6 Hz); MS (ESI, NEG) m/z: 450 (M–Na)–.

EXAMPLE 15

Preparation of (1R,2S)-2-[(2R)-2-acetylamino-3-oxo-3-{1-(4-phenyl)piperazinyl}propylthio]methyl-3-oxo- 1-cyclopentanecarboxylic Acid (Compound 13B]

A methanol solution (3 ml) of (2R)-2-acetylamino-3-oxo-3-[1-(4-phenylpiperazinyl)]-propanethiol (29.3 mg, 1 mmol), acetone (1 ml) and 1N sodium hydroxide (0.2 ml) were added to Compound (C) (32 mg, 1 mmol). The mixture was stirred at room temperature for 3 hours. After the pH was adjusted to 2.8 by adding 1N hydrochloric acid was to the reaction solution, silica gel (200 mg) was added thereto. The mixture was concentrated to dryness. The residue was purified by silica gel column chromatography (30 ml, chloroform:methanol=10:1) to give Compound (13B) (28.5 mg, yield: 63.7%).

1H-NMR (200 MHz, CDCl3) δ: 1.85, 2.13 (1H, m), 2.01 (3H, s), 2.06–2.60 (3H, m), 2.63–3.12 (6H, m), 3.68–3.92 (4H, m), 5.25 (1H, dd, J=6.96 Hz, 15.02 Hz), 6.25 (1H, brs), 6.93 (3H, m), 7.28 (2H, m), 7.48 (1H, d, J=8.42 Hz); MS (FAB, POS) m/z: 448 (M+H)+.

EXAMPLE 16

Preparation of (1R,2S)-2-{3-(3-pyridyl)propylthio}-methyl-3-oxo-1-cyclopentanecarboxylic Acid (Compound 14B)

Compound (C) (32 mg, 0.1 mmol) was dissolved in acetone (1 ml) and, a methanol solution (1 ml) of 3-(3-pyridyl)propanethiol (15.3 mg, 0.1 mmol) and 1N sodium hydroxide (0.18 ml) were added thereto. The mixture was stirred at room temperature for 3 hours. The mixture was concentrated and the residue was purified on QAE-Sephadex (Cl type, 110 ml, 0.05M–0.5M sodium chloride aqueous solution, 300 ml each, gradient elution). The objective fractions were collected. After the pH was adjusted to 2.8, the product was adsorbed onto SEPABEADS SP207 (12 ml, Nippon Rensui K.K.), washed with water and eluted with 80% hydrated methanol. By collecting the objective fractions, Compound (14B) (29.6 mg, yield: 89.8%) was obtained.

1H-NMR (200 MHz, CD3OD) δ: 1.81–2.08 (3H, m), 2.10–2.60 (5H, m), 2.68–3.00 (5H, m), 3.08 (1H, m), 7.40 (1H, m), 7.78 (1H, m), 8.40 (2H, m); MS (FAB, POS) m/z: 294 (M+H)+.

EXAMPLE 17

Preparation of (1R,2S)-2-[3-{3-(1-methylpyridinium iodide)}propylthio]methyl-3-oxo-1-cyclopentanecarboxylic Acid (Compound 15B)

Compound (C) (32 mg, 0.1 mmol) was dissolved in acetone (1 ml). A methanol solution (1.5 ml) of 3-{3-(1-methylpyridinium iodide)}propanethiol (30 mg, 0.1 mmol) and 1N sodium hydroxide are added to the solution. The mixture was stirred at room temperature for 2 hours. After the reaction solution was concentrated, the residue was purified in a manner similar to Example 16 to give Compound (15B) (17.8 mg, yield: 41%).

1H-NMR (200 MHz, CD3OD) δ: 1.85–2.10 (3H, m), 2.12–2.48 (3H, m), 2.48–2.86 (5H, m), 2.87–3.08 (3H, m), 4.42 (3H, m), 7.99 (1H, dd, J=6.23 Hz, 7.69 Hz), 8.48 (1H, d, J=7.69 Hz), 8.76 (1H, d, J=6.23 Hz), 8.89 (2H, m); MS (FAB, POS) m/z: 308 (M–H)+.

EXAMPLE 18

Preparation of 5-[(2R)-(2-acetylamino-2-carboxy) ethylthio]methyl-2-cyclopenten-1-one (Compound 1C)

(1) Preparation of (4R)-2-[(2R)-(2-acetylamino-2-methoxycarbonyl)ethylthio]methyl-4-tert-butyldimethylsiloxy-2-cyclopenten-1-one (Compound a)

Compound (c) (370 mg, 1.24 mmols) was dissolved in methanol (4 ml) and methyl iodide (0.16 ml, 2.48 mmols) was added to the solution. The mixture was stirred at room temperature for 2 hours. After the reaction solution was concentrated, methanol (3 ml) and N-acetyl-L-cysteine methyl ester (220 mg, 1.24 mmol) were added to the residue. The mixture was stirred at room temperature for 1.5 hrs. The reaction solution was concentrated and the residue was purified by silica gel column chromatography (60 ml, dichloromethane:methanol=40:1) to give Compound (a-1) (378 mg, yield: 75.7%).

1H-NMR (200 MHz, CDCl3) δ: 0.12 (3H, s), 0.14 (3H, s), 0.92 (9H, s), 2.07 (3H, s), 2.31 (1H, dd, J=2.11 Hz, 18.31 Hz), 2.80 (1H, dd, J=5.99 Hz, 18.31 Hz), 2.99 (2H, m), 3.30 (2H, m), 3.78 (3H, s), 4.86 (1H, m), 4.92 (1H, m), 6.56 (1H, d, J=7.69 Hz), 7.29 (1H, m); MS (FAB, POS) m/z: 402 (M+H)+.

(2) Preparation of (4R)-2-[(2R)-(2-acetylamino-2-methoxycarbonyl)ethylsulfonyl]methyl-4-tert-butyldimethylsiloxy-2-cyclopenten-1-one (Compound a-2)

Compound (a-1) (378 mg, 0.94 mmol) was dissolved in dichloromethane (30 ml). Under ice cooling, m-chloroperbenzoic acid (406 mg, purity 80%, 1.88 mmols) was added to the solution. After water (15 ml) and 20% sodium hydrogen sulfite (3 ml) were added to the reaction solution, saturated sodium hydrogen carbonate was added to the mixture until the pH of the aqueous layer became 7.0. The dichloromethane layer was washed with saturated sodium chloride aqueous solution and concentrated. The residue was purified by silica gel column chromatography (50 ml, dichloromethane:methanol=10:1) to give Compound (a-2) (355 mg, yield: 87.3%).

1H-NMR (200 MHz, CDCl3) δ: 0.13 (3H, s), 0.14 (3H, s), 0.96 (9H, s), 2.08 (3H, s), 2.35 (1H, dd, J=2.16 Hz, 18.52 Hz), 2.86 (1H, dd, J=5.94 Hz, 18.52 Hz), 3.65 (2H, d, J=4.97 Hz), 3.80 (3H, s), 3.81–4.16 (2H, m), 4.89–5.09 (2H, m), 6.70 (1H, brd, J=7.41z), 7.66 (1H, m); MS (FAB, POS) m/z: 434 (M+H)+.

(3) Preparation of (4R)-2-[(2R)-(2-acetylamino-2-methoxycarbonyl)ethylsulfonyl]methyl-4-tert-butyldimethylsiloxy-2-cyclopentan-1-one (Compound a)

Compound (a-2) (355 mg, 0.82 mmol) was dissolved in ethanol (20 ml) and 10% Pd—C (80 mg, 50% hydrated) was added to the solution. The mixture was stirred at room temperature for 5 hours in hydrogen atmosphere. The reaction solution was filtered and the filtrate was concentrated to give Compound (a) (330 mg, yield: 92.9%).

MS (FAB, POS) m/z: 436 (M+H)+.

(4) Preparation of (4R)-2-[(2R)-(2-acetylamino-2-carbonyl) ethylthio]methyl-4-tert-butyldimethylsiloxy-2-cyclopentan-1-one (Compound a-3)

Acetone (2 ml), methanol (8 ml), N-acetyl-L-cysteine (123.9 mg, 0.76 mmol) and 1 N sodium hydroxide (1.52 ml) were added to Compound (a) (330 mg, 0.76 mmol). The mixture was stirred at room temperature for 2 hours. After the reaction solution was concentrated, purification was performed using Sephadex LH-20 (200 ml, 80% hydrated methanol) to give Compound (a-3) (299 mg). The compound was used for the subsequent reaction without further purification.

(5) Preparation of 5-[(2R)-(2-acetylamino-2-carboxy) ethylthio]methyl-2-cyclopenten-1-one (Compound 1C)

Methanol (15 ml), water (1 ml) and Dowex 50 (H+ type, 300 mg) were added to Compound (a-3) (299 mg, 0.76 mmol). The mixture was stirred at room temperature for 20 hours. After filtration, silica gel (1 g) was added to the filtrate followed by concentration. The residue obtained was purified by silica gel column chromatography (80 ml, dichloromethane:methanol:acetic acid=5:1:0.1) to give Compound (1C) (83 mg, yield: 39%).

1H-NMR (200 MHz, D2O) δ: 2.00 (3H, s), 2.45–3.16 (7H, m), 4.52 (1H, m), 6.20 (1H, m), 7.98 (1H, m); MS (FAB, POS) m/z: 258 (M+H)+.

EXAMPLE 19

Preparation of (4R)-2-[(2R)-(2-acetylamino-2-carboxy)ethylthio]methyl-4-hydroxy-2-cyclopenten-1-one (Compound 2C)

Acetone (2 ml), methanol (4 ml), N-acetyl-L-cysteine (61.9 mg, 0.39 mmol) and 1 N sodium hydroxide (0.76 ml) were added to (4R)-2-[(2R)-(2-acetylamino-2-methoxycarbonyl)ethylsulfonyl]methyl-4-tert-butyldimethylsioloxy-2-cyclopenten-1-one (165 mg, 0.38 mmol). The mixture was stirred at room temperature for 2 hours. After the reaction solution was concentrated, methanol (5 ml), water (1 ml) and Dowex 50 (H type, 700 mg) were added to the residue followed by stirring at room temperature for 16 hours. After filtration, silica gel (500 mg) was added to the reaction mixture, which was then concentrated. The residue was purified by silica gel column chromatography (80 ml, dichloro-methane:methanol:acetic acid=5:1:0.1). After concentration, the residue was dissolved in water (10 ml) and 1N sodium hydroxide was added thereto to adjust the pH to 6.9. Thus, the sodium salt (61 mg, yield: 54.4%) of Compound (2C) was obtained.

1H-NMR (200 MHz, D2O) δ: 2.00 (3H, s), 2.3 (1H, dd, J=1.83 Hz, 18.83 Hz), 2.75–3.07 (3H, m), 3.32 (2H, s), 4.48 (1, dd, J=4.76 Hz, 8.01 Hz), 4.98 (1H, m), 7.52 (1H, m); MS (ESI, NEG) m/z: 272 (M–Na)–.

EXAMPLE 20

Preparation of 2-[(2R)-(2-acetylamino-2-carboxy)-ethylthio]methyl-3-hydroxy-2-cyclopenten-1-one (Compound 3C)

N-Acetyl-L-cysteine (193 mg, 1.18 mmol), methanol (2 ml), acetone (4 ml) and 1 N sodium hydroxide (2.36 ml) were added to Compound (d) (347 mg, 1.18 mmol). The mixture was stirred at room temperature. 1N Sodium hydroxide was added to the mixture portionwise until the reaction solution became neutral (4 hours). Silica gel (1.2 g) was then added to the reaction solution. The mixture was concentrated. The residue was purified by silica gel column chromatography (100 ml, dichloromethane:methanol:acetic acid=5:1:0.1 to 2.5:1:0.1) to give Compound (3C) (308 mg, yield: 95.6%).

1H-NMR (200 MHz, D2O) δ: 2.00 (1H, s), 2.49 (4H, s), 2.72–2.99 (2H, s), 3.26 (2H, s), 4.38 (1H, dd, J=4.68 Hz, 8.26 Hz); MS (FAB, NEG) m/z: 272 (M–H)–.

EXAMPLE 21

Preparation of 3-{(2R)-2-acetylamino-2-carboxyethylthio}methyl-4-oxo-1-n-pentanoic acid (Compound 1D)

Compound (a) (256.3 mg, 2.00 mmols) was dissolved in tetrahydrofuran (3 ml) and 1,8-diazabicyclo[5.4.0]-undeca-7-ene (609 mg, 4.00 mmols) was added to the solution. The mixture was reacted overnight at room temperature. After Amberlist-15 (3 g) was added to the reaction mixture, the mixture was stirred for 5 minutes. Then the resin was filtered off. The filtrate was concentrated in vacuo. The residue was purified by silica gel column chromatography (40 ml, hexane:ethyl acetate=3:2 to 1:1) to fractionate the fraction containing Compound (b). The fraction was concentrated in vacuo. The residue obtained was dissolved in tetrahydrofuran (3 ml). N-Acetyl-L-cysteine (107.7 mg, 0.66 mmol) and triethylamine (265.1 mg, 2.62 mmols) were added to the solution. After stirring at room temperature overnight, the reaction solution was concentrated in vacuo. The residue was purified by silica gel column chromatography (40 ml, methylene chloride:methanol=10:1 to 2:1). The objective fraction was concentrated in vacuo and dissolved in tetrahydrofuran (3 ml) and methanol (1 ml). Amberlist-15 (2 g) was added to the solution. After stirring the mixture for 3 minutes, the resin was filtered off and the filtrate was concentrated in vacuo. The residue was purified by silica gel column chromatography (40 ml, methylene chloride:methanol=10:1) to give Compound (1D) (40.9 mg, yield: 7%).

1H-NMR (200 MHz, DMSO-d6)) δ: 1.86 (3H, s), 2.18 (3H, s), 2.4–2.6 (2H, m), 2.7–3.0 (4H, m), 3.05 (1H, m), 4.38 (1H, ddd, J=8.1, 8.1, 5.1 Hz), 8.24 (1H, d, J=8.1 Hz); MS (FAB, POS) m/z: 292 (M+H)+.

In a manner similar to the above procedures, 3-{(2R)-2-acetylamino-2-methoxycarbonylethylthio}methyl-4-oxo-1-n-pentanoic acid (Compound 2D) may be prepared.

1H-NMR (200 MHz, DMSO-d6) δ: 1.86 (3H, s), 2.17 (3H, s), 2.4–2.7 (2H, m), 2.7–3.0 (4H, m), 3.04 (1H, m), 3.65 (3H, s), 4.46 (1H, ddd, J=8.1, 8.1, 5.7 Hz), 8.39 (1H, d, J=8.1 Hz); MS (FAB, POS) m/z: 306 (M+H)+.

EXAMPLE 22

Preparation of trans-2-{(2R)-2-acetylamino-2-methoxycarbonylethylthio}methyl-3-ethoxycarbonyl-1-cyclobutanone (Compound 3D)

(1) Preparation of trans-2-hydroxymethyl-3-ethoxycarbonyl-1-cyclobutanone (Compound e-2)

Under ice cooling, diisopropylamine (0.296 g, 2.92 mmols) was added to a solution of n-butyl lithium (1.59 M/hexane solution, 2.79 mmols) in tetrahydrofuran (8 ml) and the mixture was stirred for 10 minutes. After cooling to −78° C., a solution of 3-ethoxycarbonyl-1-cyclobutanone (Compound e-1) (355.4 mg, 2.50 mmols) in tetrahydrofuran (3 ml) was dropwise added to the mixture, which was then stirred for 15 minutes. After the temperature was once elevated to 0° C., the mixture was stirred for 15 minutes and again cooled to −78° C. Hexamethylphosphoramide (535.8 mg, 2.99 mmols) was added to the system. After stirring for 5 minutes, a solution obtained by trapping formaldehyde subjected to cracking at 160° C. and trapped in diethyl ether of −78° C. was poured into the system through a needle. The reaction was terminated by adding hydrochloric acid and the insoluble matters were filtered off. The filtrate was concentrated in vacuo. The residue was purified by silica gel column chromatography (50 ml, hexane:diethyl ether=1:1 to 1:2) to give Compound (e-2) (50.7 mg, yield: 12%).

1H-NMR (60 MHz, CDCl3) δ: 1.30 (3H, t, J=7 Hz), 2.17 (1H, br), 3.23 (2H, m), 3.6–4.0 (4H, m), 4.20 (2H, q, J=7 Hz)

(2) Preparation of 2-methylidene-3-ethoxycarbonyl-1-cyclobutanone (Compound f)

Compound (e-2) was dissolved in methylene chloride (2 ml). Under ice cooling, triethylamine (60.1 mg, 0.59 mmol) and mesyl chloride (36.7 mg, 0.32 mmol) were added to the solution. The mixture was stirred for 30 minutes under the same conditions. Water and diethyl ether were added to the system for separation. The resulting organic layer was washed with water and then with saturated sodium chloride aqueous solution, dried over anhydrous sodium sulfate and concentrated in vacuo to give Compound (f) (40.3 mg, yield: 96%).

1H-NMR (60 MHz, CDCl3) δ: 1.33 (3H, t, J=7 Hz), 3.30 (1H, dd, J=15 Hz, 8 Hz), 3.40 (1H, dd, J=15.6 Hz), 4.00 (1H, m), 4.40 (2H, q, J=7 Hz), 5.50 (1H, m), 6.03 (1H, m)

(3) Preparation of trans-2-{(2R)-2-acetylamino-2-methoxycarbonylethylthio}methyl-3-ethoxycarbonyl-1-cyclobutanone (Compound 3D)

Compound (f) (40.3 mg, 0.26 mmol) was dissolved in methylene chloride (2 ml). Under ice cooling, N-acetyl-L-cysteine (46.1 mg, 0.26 mmol) and triethylamine (10.9 mg, 0.11 mmol) were added to the solution. The mixture was stirred for an hour under the same conditions. The reaction solution was concentrated and the residue was purified by silica gel column chromatography (20 ml, methylene chloride:methanol=40:1) and Sephadex LH-20 (10 ml, eluted with methanol) to give Compound (3D) (27.4 mg, yield: 36.4%).

1H-NMR (200 MHz, CDCl3) δ: 1.31 (3H, t, J=7.4 Hz), 2.07 (3H, s), 2.80 (2H, m), 3.0–3.5 (5H, m), 3.78 (3H, s), 3.84 (1H, m), 4.24 (2H, dd, J=7.0, 1.7 Hz), 4.83 (1H, dt, J=7.6, 4.9 Hz), 6.46 (1H, brs, J=6.3 Hz); MS (FAB, POS) m/z: 332 (M+H)+.

EXAMPLE 23

Preparation of trans-2-{(2R)-2-acetylamino-2-carboxyethylthio}methyl-3-oxo-1-cyclobutanecarboxylic Acid (Compound 4D)

After 3N hydrochloric acid aqueous solution (4 ml) was added to Compound (3) (17.4 mg, 0.05 mmol), the mixture was stirred at room temperature overnight. The reaction solution was concentrated in vacuo. The residue obtained was purified twice by Sephadex LH-20 (100 ml and 200 ml, eluted with methanol) and twice by silica gel column chromatography (2 ml, methylene chloride:methanol=20:1 to 2:1) to give Compound (4D) (6.0 mg, yield: 40%).

1H-NMR (200 MHz, CD3OD) δ: 2.01 (3H, 2.80–4.0 (8H, m), 4.60 (1H, m); MS (FAB, POS) m/z: 290 (M+H)+.

EXAMPLE 24

Preparation of trans-3-acetoxymethyl-2-(2,3-dihydroxypropylthio)methyl-1-cyclobutanone (Compound 5D)

(1) Preparation of 3-acetoxymethyl-2-methylidene-1-cyclobutanone (Compound d)

After tetrahydrofuran (3 ml) and 1,8-diazabicyclo[5.4.0]-undeca-7-ene (25.5 mg, 0.168 mmol) was added to Compound (c) (30 mg, 0.14 mmol), the mixture was stirred at room temperature for an hour. The reaction solution was purified by silica gel column chromatography (10 ml, hexane:ethyl acetate=2:1) to give Compound (d) (23 mg, yield: 95.5%).

1H-NMR (60 MHz, CDCl3) δ: 2.00 (3H, s), 2.65–3.30 (3H, m), 4.33 (2H, m), 5.30 (1H, d, J=4.1 Hz), 5.80 (1H, d, J=4.1 Hz)

(2) Preparation of trans-3-acetoxymethyl-2-(2,3-dihydroxypropylthio)methyl-1-cyclobutanone (Compound 5D)

Compound (d) (23 mg, 0.133 mmol) was dissolved in acetone (1 ml) and a solution of alpha-thioglycerin (11 ul, 0.133 mmol) in methanol (1 ml) was added to the solution. The mixture was stirred at room temperature for an hour. The reaction solution was concentrated. The residue obtained was purified by silica gel column chromatography (20 ml, dichloromethane:methanol=20:1) to give Compound (5D) (19 mg, yield: 51.3%).

1H-NMR (200 MHz, CDCl3) δ: 2.07, 2.10 (3H, sx2), 2.45–3.45 (8H, m), 3.50 3.90 (3H, m), 4.33 (2H, m)

EXAMPLE 24

Preparation of 2-{(2R)-2-acetylamino-2-carboxyethylthio}methyl-3-oxo-1-cyclohexanecarboxylic acid (Compound 6D)

(1) Preparation of 4.5-dimethoxycarbonyl-3-trimethylsiloxy-1-cyclohexene (Compound g-3)

Compound (g-1) (589 mg, 4.09 mmols) and Compound (g-2) (588 mg, 4.09 mmols) were dissolved in benzene. The reaction was carried out at 150° C. for 5 hours. After the reaction solution was concentrated, the residue was purified by silica gel column chromatography (80 ml, hexane:ethyl acetate=5:1 to 3:1) to give Compound (g-3) (875 mg, yield: 74.6%).

1H-NMR (200 MHz, CDCl3) δ: 0.05–0.12 (9H, m), 1.95–2.20 (1H, m), 2.70–2.94 (1H, m), 2.95–3.19 (1H, m), 3.68 (3H, m), 3.70 (3H, s), 4.50 (1H, m), 5.50–5.90 (2H, m)

(2) Preparation of 4,5-bis(hydroxymethyl)-3-hydroxy-1-cyclohexene (Compound a-4)

Lithium borohydride was suspended in anhydrous tetrahydrofuran (25 ml). Under ice cooling, a solution of Compound (g-3) (875 mg, 3.05 mmols) in anhydrous tetrahydrofuran (4 ml) was dropwise added to the suspension. The reaction was carried out for 2 hours. Then water (0.196 ml), 15% sodium hydroxide aqueous solution (0.196 ml) and water (0.59 ml) were added to the mixture. Stirring was further continued. After the suspension was filtered, the filtrate was concentrated. The residue was purified by silica gel column chromatography (20 ml, methylene chloride:methanol=20:1) to give Compound (g-4) (340 mg, 70.5%).

Preparation of 5,6-bis(hydroxymethyl)-2-cyclohexen-1-one (Compound g-5)

Compound (g-4) (320 mg, 2.02 mmols) was dissolved in acetone (20 ml). Manganese dioxide (1400 mg) was gradually added to the solution. After the reaction, the precipitates were filtered off. The filtrate was concentrated and the residue was purified by silica gel column chromatography (40 ml, methylene chloride:methanol=10:1) to give Compound (g-5) (205 mg, 61.1%).

1H-NMR (200 MHz, CDCl3) δ: 2.30–2.60 (4H, m), 3.65 (2H, m), 3.76 (1H, dd, J=3.67 Hz, 11.08 Hz), 4.10 (1H, dd, J=3.67 Hz, 11.08 Hz), 5.98 (1H, dt, J=2.12 Hz, 12.13 Hz), 7.08 (1H, m)

(4) Preparation of 2,3-bis(acetoxymethyl)-1-cyclohexanone (Compound g-6)

Pyridine (10 ml) and acetic anhydride (3 ml) were added to Compound (g-5) (205 mg, 1.31 mmol). The mixture was reacted at room temperature for 2 hours. After the reaction solution was concentrated, the residue was subjected to silica gel column chromatography (20 ml, hexane:ethyl acetate=1:1). The fraction was concentrated and the concentrate was dissolved in ethanol (20 ml). Palladium-carbon (50% hydrated) (50 mg) was added to the solution. The reaction was carried out at room temperature overnight in hydrogen atmosphere. The catalyst was filtered off and the filtrate was concentrated. The residue was purified by silica gel column chromatography (30 ml, methylene chloride:methanol=20:1) to give Compound (g-6) (175 mg, 73.0%).

1H-NMR (200 MHz, CDCl3) δ: 1.70 (2H, m), 1.89–2.20 (3H, m), 2.02 (3H, s), 2.08 (3H, s), 4.13 (2H, m), 4.38 (2H, m)

(5) Preparation of 3-acetoxymethyl-2-[2,3-(dihydroxy) propylthio]methyl-1-cyclohexanone (Compound g-7)

2,3-Bis(acetoxymethyl)-1-cyclohexanone (Compound g-6) (200 mg, 0.826 mmol) was dissolved in acetone (3 ml). A solution of alpha-thioglycerin (89.2 mg, 0.826 mmol) in methanol (1 ml) and 1N sodium hydroxide (0.826 ml) were added to the solution. The mixture was stirred at room temperature for an hour. Silica gel (1 g) was added to the reaction mixture. After concentration, the residue was purified by silica gel column chromatography (30 ml, dichloromethane:methanol=20:1) to give Compound (g-7) (175 mg, yield: 73.0%).

MS (FAB, POS) m/z: 291 (M+H)+.

(6) Preparation of 3-acetoxymethyl-2-[(2,3-O-isopropylidene)propylthio]methyl-1-cyclohexanone (Compound g-8)

Compound (g-7) (170 mg, 0.586 mmol) was dissolved in anhydrous acetone (1.5 ml). p-Toluenesulfonic acid monohydrate (11 mg, 0.06 mmol), dimethoxypropane (0.34 ml, 1.76 mmol) were added to the solution. The mixture was stirred at room temperature for 30 minutes. After water (2 ml) was added to the reaction mixture and the pH was adjusted to 7.0 with saturated hydrogensodium carbonate, the mixture was extracted three times with ethyl acetate (5 ml). The organic layer was washed with saturated sodium chloride aqueous solution (5 ml), dried over anhydrous sodium sulfate and concentrated to give Compound (g-8) (191 mg, yield: 98.7%).

1H-NMR (200 MHz, CDCl3) δ: 1.30 (3H, s), 1.39 (3H, s), 1.52–2.15 (5H, m), 2.03 (3H, s), 2.20–3.05 (7H, m) 3.67 (1H, m), 3.82–4.29 (4H, m)

(7) Preparation of 3-hydroxymethyl-2-[(2,3-O-isopropylidene)propylthio]methyl-1-cyclohexanone (Compound g-9)

Compound (g-8) (191 mg, 0.578 mmol) was dissolved in methanol (2 ml). Under ice cooling, water (0.2 ml) and 1N sodium hydroxide (0.57 ml) were added to the solution. The mixture was stirred for 15 minutes while ice cooling. By adding 1N hydrochloric acid to the reaction mixture, the pH was adjusted to 6.8. Silica gel (500 mg) was added to the system. The mixture was then concentrated and the residue was purified by silica gel column chromatography (20 ml, dichloromethane:methanol=30:1) to give Compound (g-9) (155 mg, yield: 93.1%).

MS (FAB, POS) m/z: 289 (M+H)+.

(8) Preparation of 3-hydroxymethyl-2-[(2RS)-(2,3-O-isopropylidene)propylsulfonyl]methyl-1-cyclohexanone (Compound g-10)

Compound (g-9) (155 mg, 0.538 mmol) was dissolved in dichloromethane (2 ml). Under ice cooling, a dichloromethane solution (5 ml) of m-chloroperbenzoic acid (232 mg, purity 80%, 1.07 mmol) was added to the solution. After the reaction mixture was filtered, water (4 ml) and 20% sodium hydrogen sulfite (0.17 ml) were added to the filtrate. Saturated sodium hydrogen carbonate was added to the mixture until the pH of the aqueous layer became 7.0. After the aqueous layer was extracted twice with dichloromethane (10 ml), the dichloromethane layer was washed with saturated sodium chloride aqueous solution (15 ml), dried over anhydrous sodium sulfate and concentrated. The residue was purified by silica gel column chromatography (18 ml, hexane:ethyl acetate=1:3) to give Compound (g-10) (151 mg, yield: 87.7%).

MS (FAB, POS) m/z: 321 (M+H)+.

(9) Preparation of 2-[(2,3-O-isopropylidene)-propylsulfonyl]methyl-3-oxo-1-cyclohexanecarboxylic acid (Compound g)

Compound (g-10) (151 mg, 0.47 mmol) was dissolved in acetone (9 ml). Jones reagent was added to the solution until the solution turned orange. The mixture was stirred at room temperature for 10 minutes. Thereafter, 2-propanol was added to the reaction mixture until it turned green. The mixture was concentrated and water (5 ml) was added to the concentrate. The resulting solution was extracted 3 times with dichloromethane (5 ml). The dichloromethane layer was washed with saturated sodium chloride aqueous solution (10 ml), dried over anhydrous sodium sulfate and then concentrated to give Compound (g) (88.6 mg, yield: 56.4%).

MS (ESI, NEG) m/z: 333 (M–H)–.

(10) Preparation of 2-{(2R)-2-acetylamino-2-carboxyethylthio}methyl-3-oxo-1-cyclohexanecarboxylic acid (Compound 6D)

Compound (g) (88.6 mg, 0.265 mmol) was dissolved in acetone (3 ml). N-Acetyl-L-cysteine (43.2 mg, 0.265 mmol), 1N sodium hydroxide (0.78 ml, 0.795 mmol) and methanol (1 ml) were added to the solution. The mixture was stirred for 2 hour at room temperature. After the pH of the mixture was adjusted to 6.8 with 1N hydrochloric acid, the residue was purified by Sephadex LH-20 (200 ml, 80% hydrated methanol) to give the sodium salt (57.7 mg, yield: 60.3%) of Compound (6D).

1H-NMR (200 MHz, D2O) δ: 1.52–2.18 (4H, m), 2.00 (3H, s), 2.27–3.22 (8H, m), 4.28 (1H, dd, J=4.03 Hz, 8.34 Hz); MS (ESI, NEG) m/z: 361 (M–Na)–.

EXAMPLE 25

Preparation of 3-[(2R)-(2-acetylamino-2-carboxy) ethylthio]methyl-4-oxo-4-phenylbutyric Acid (Compound 7D)

N-Acetyl-L-cysteine (39 mg, 0.24 mmol) and ethanol (4 ml) were added to 4-oxo-3-(1-piperidinyl)methyl-4-phenylbutyric acid (66 mg, 0.24 mmol). The mixture was heated to reflux for 2 hours. After the reaction mixture was concentrated in vacuo, water (5 ml) and ethyl acetate (8 ml) were added to the residue. The pH of the aqueous layer was adjusted to 2.0 with 1N hydrochloric acid followed by liquid-liquid separation. The mixture was extracted twice with ethyl acetate (8 ml). The collected ethyl acetate layers were washed with saturated sodium chloride aqueous solution (5 ml), dried over anhydrous sodium sulfate and then concentrated in vacuo. The residue was purified by silica gel column chromatography (20 ml, chloroform methanol= 20:1) to give Compound (7D) (45 mg, yield: 53.1%).

1H-NMR (60 MHz, CD3OD) δ: 2.19 (1.5H, s), 2.20 (1.5H, s), 2.50–3.30 (6H, m), 4.16 (1H, m), 4.58 (1H, m), 7.55 (3H, m), 8.00 (2H, m); MS (FAB, POS) m/z: 354 (M+H)+.

EXAMPLE 26

Preparation of 3-[(2R)-(2-acetylamino-2-methoxycarbonyl)ethylthio]methyl-4-oxo-4-phenylbutyric Acid (Compound 8D)

N-Acetyl-L-cysteine methyl ester (66.3 mg, 0.37 mmol) and ethanol (4 ml) were successively added to 4-oxo-3-(1-piperidyl)methyl-4-phenylbutyric acid (103 mg, 0.37 mmol). The mixture was heated to reflux for an hour. The reaction mixture was purified in a manner similar to Example 25 to give Compound (8D) (116 mg, yield: 84.5%).

1H-NMR (60 MHz, CDCl3) δ: 2.01 (1.5H, s), 2.03 (1.5H, s), 2.48–3.16 (6H, m), 3.70 (1.5H, s), 3.73 (1H, s), 4.17 (1H, m), 4.85 (1H, m), 6.70 (1H, m), 7.52 (3H, m), 7.90 (2H, m); MS (FAB, POS) m/z: 368 (M+H)+.

EXAMPLE 27

Preparation of 3-[(2R)-(2-acetylamino-2-methoxycarbonyl)ethylthio]methyl-4-(4-methoxyphenyl)-4-oxobutyric Acid (Compound 9D)

N-Acetyl-L-cysteine methyl ester (66.3 mg, 0.37 mmol) and ethanol (3 ml) were added to 4-(4-methoxyphenyl)-4-oxo-3-(1-piperidyl)methyl-butyric acid (109 mg, 0.37 mmol). The mixture was heated to reflux for 2 hours. Purification was performed in a manner similar to Example 25 to give Compound (9D) (110 mg, yield: 73.4%).

1H-NMR (200 MHz, CDCl3) δ: 1.98 (1.5H, s), 2.05 (1.5H, s), 2.68 (2H, m), 2.90 (4H, m), 3.69 (1.5H, s), 3.72 (1.5H, s), 3.89 (3H, s), 4.02 (1H, m), 4.80 (1H, m), 6.48–6.72 (1H, m), 6.98 (2H, d, J=8.92 Hz), 7.40 (1H, brs), 7.98 (2H, dd, J=3.3 Hz, 8.92 Hz); MS (FAB, POS) m/z: 398 (M+H)+.

EXAMPLE 28

Preparation of 3-{2-(acetylamino)ethylthio}methyl-4-(4-methoxyphenyl)-4-oxobutyric Acid (Compound 10D)

N-Acetyl-L-cysteamine (45 mg, 0.37 mmol) and ethanol (3 ml) were added to 4-(4-methoxyphenyl)-4-oxo-3-(1-piperidyl)methyl-4-phenylbutyric acid (109 mg, 0.37 mmol). The mixture was heated to reflux for 2 hours. Purification was performed in a manner similar to Example 25 to give Compound (10D) (93 mg, yield: 72%).

1H-NMR (200 MHz, CDCl3) δ: 1.98 (1.5H, s), 2.58–2.76 (4H, m), 2.90 (2H, m), 3.39 (2H, m), 3.89 (3H, m), 4.07 (1H, m), 6.12 (1H, t, J=4.68 Hz), 6.60 (1H, brs), 6.95 (2H, d, J=8.9 Hz), 7.98 (2H, d, J=8.9 Hz); MS (FAB, POS) m/z: 340 (M+H)+.

EXAMPLE 29

Preparation of 3-{2-(acetylamino)ethylthio}methyl-4-oxo-4-phenylbutyric Acid (Compound 11D)

N-Acetyl-L-cysteamine (45 mg, 0.37 mmol) and ethanol (3 ml) were added to 4-oxo-4-phenyl-3-(1-piperidyl)methylbutyric acid (103 mg, 0.37 mmol). The mixture was heated to reflux for 2 hours. Purification was performed in a manner similar to Example 25 to give Compound (11D) (83 mg, yield: 71.7%).

1H-NMR (200 MHz, CDCl3) δ: 1.97 (3H, s), 2.58–2.78 (4H, m), 2.90 (2H, m), 3.48 (2H, m), 4.11 (1H, m), 6.25 (1H, t, J=5.21 Hz), 7.50 (3H, m), 7.98 (2H, m), 8.05 (1H, brs); MS (FAB, POS) m/z: 310 (M+H)+.

EXAMPLE 30

Preparation of 3-{2-(acetylamino)ethylthio}methyl-4-(4-methylphenyl)-4-oxobutyric Acid (Compound 12D)

N-Acetyl-L-cysteamine (57 mg, 0.47 mmol) and ethanol (3 ml) were added to 4-(4-methylphenyl)-4-oxo-3-(1-piperidyl)methylbutyric acid (131 mg, 0.47 mmol). The mixture was heated to reflux. Purification was performed in a manner similar to Example 25 to give Compound (12D) (114 mg, yield: 73.6%).

1H-NMR (60 MHz, CDCl3) 3 : 2.30 (3H, s), 2.70 (3H, s), 2.76–3.30 (4H, m), 3.30–4.15 (4H, m), 4.33 (1H, m), 6.70 (1H, t, J=6.0 Hz), 7.50 (2H, d, J=9.2 Hz), 7.80 (1H, brs), 8.16 (2H, d, J=9.2 Hz); MS (FAB, POS) m/z: 382 (M+H)+.

EXAMPLE 31

Preparation of 3-{(2R)-(2-acetylamino-2-methoxycarbonyl)ethylthio}methyl-4-(4-methylphenyl)-4-oxobutyric Acid (Compound 13D)

N-Acetyl-L-cysteine methyl ester (92 mg, 0.52 mmol) and ethanol (3 ml) were added to 4-(4-methylphenyl)-4-oxo-3-(1-piperidyl)methylbutyric acid (142 mg, 0.52 mmol). The mixture was heated to reflux for 2 hours. Purification was performed in a manner similar to Example 25 to give Compound (13D) (126 mg, yield: 63.5%).

1H-NMR (60 MHz, CDCl3) δ: 2.30 (3H, s), 2.38 (1.5H, s), 2.80 (3H, s), 2.98–3.60 (6H, m), 4.01 (1.5H, s), 4.10 (1.5H, s), 4.40 (1H, m), 5.14 (1H, m), 7.02 (1H, m), 7.41 (1H, brs), 7.52 (2H, d, J=8.5 Hz), 8.17 (2H, d, J=8.5 Hz); MS (FAB, POS) m/z: 324 (M+H)+.

EXAMPLE 32

Preparation of 3-[(2R)-(2-acetylamino-2-methoxycarbonyl)ethylthio]methyl-4-oxo-4-(3-pyridyl)butyric Acid (Compound 32D)

(1) Preparation of methyl 4-oxo-4-(3-pyridyl)butyrate (Compound 32D-A)

In nitrogen atmosphere, a solution of 3-pyridinecarboxyaldehyde (10.7 g, 100 mmols) in anhydrous dimethylformamide (20 ml) was dropwise added to a solution of sodium cyanide (2.44 g, 50 mmols) at 30° C. in anhydrous dimethylformamide (80 ml) over 30 minutes. After stirring for 30 minutes, a solution of methyl acrylate (8.6 g, 100 mmols) in anhydrous dimethylformamide (80 ml) was dropwise added to the reaction mixture over an hour followed by stirring for 3 hours at 30° C. Acetic acid (0.66 ml) and water (30 ml) were added to the reaction solution. After stirring for 10 minutes, the mixture was concentrated in vacuo. Water (360 ml) and chloroform (300 ml×3) were added to the residue for separation. The resultant organic phase was washed with saturated sodium chloride aqueous solution (300 ml), dried over anhydrous sodium sulfate and concentrated in vacuo. The residue was purified by silica gel column chromatography (650 ml, hexane:ethyl acetate= 1:1–1:2) to give Compound (32D-A) (7.87 g, yield: 40.7%).

(2) Preparation of 4-oxo-4-(3-pyridyl)butyric acid (Compound 32D-B)

Compound (32D-A) (5.04 g, 26.11 mmols) was dissolved in methanol (60 ml). After 1N sodium hydroxide aqueous solution (32 ml) was added to the solution, the mixture was stirred for 3 hours at room temperature. Then, 2N hydrochloric acid (16 ml) was added to the reaction mixture followed by concentration in vacuo. The residue was purified by silica gel column chromatography (250 ml, chloroform:methanol:acetic acid=20:1:0.5) to give Compound (32D-B) (3.13 g, yield: 66.9%).

1H-NMR (200 MHz, CD3OD) δ: 2.72 (3H, t, J=6.5 Hz), 3.33 (3H, t, J=6.5 Hz), 7.59 (1H, m), 8.42 (1H, m), 8.73 (1H, m), 9.14 (1H, m); MS (FAB, POS) m/z: 180 (M+H)+.

(3) Preparation of 4-oxo-4-(3-pyridyl)-3-(1-piperidyl) methylbutyric acid (Compound 32D-C)

Piperidine (140 mg, 1.64 mmol) and 37% formalin (0.133 ml, 1.64 mmol) were added to Compound (32D-B) (246 mg, 1.37 mmol). The mixture was stirred at 100° C. for 2 hours. Silica gel (1.8 g) was added to the reaction solution. After concentration, the residue was purified by silica gel column chromatography (30 ml, chloroform:methanol:acetic acid=10:1:0.5 to 10:5:3) to give Compound (32D-C) (300 mg, yield: 79%).

1H-NMR (200 MHz, CDCl3) δ: 1.45–1.80 (6H, m), 2.30–3.15 (8H, m), 4.28 (1H, m), 7.46 (1H, dd, J=4.7 Hz, 8.0 Hz), 8.00 (1H, brs), 8.37 (1H, dt, J=2.0 Hz, 8.0 Hz), 8.78 (1H, dd, J=1.6 Hz, J=4.8 Hz), 9.28 (1H, d, J=1.6 Hz)

(4) Preparation of 3-[(2R)-(2-acetylamino-2-methoxycarbonyl)ethylthio]methyl-4-oxo-4-(3-pyridyl) butyric acid (Compound 32D)

N-Acetyl-L-cysteine methyl ester (96.2 mg, 0.54 mmol) was added to a solution of Compound (32D-C) (150 ml, 0.54 mmol) in ethanol (3 ml). The mixture was heated to reflux for 2 hours. The reaction mixture was concentrated. The residue was purified by silica gel column chromatography (30 ml, chloroform:methanol:acetic acid=20:1:0.5) to give Compound (32D) (89 mg, yield: 44.7%).

1H-NMR (200 MHz, CDCl3) δ: 1.98 (1.5H, s), 2.01 (1.5H, s), 2.70 (2H, m), 2.93 (4H, m), 3.68 (1.5H, s), 3.71 (1.5H, s), 4.06 (1H, m), 4.79 (1H, m), 6.80 (1H, m), 7.20 (1H, m, NH), 7.49 (1H, m), 8.35 (1H, m), 8.75 (1H, d, J=3.9 Hz), 9.24 (1H, s), 1.048 (1H, brs); MS (FAB, POS) m/z: 369 (M+H)+.

EXAMPLE 33

Preparation of 4-[(2R)-{(2-acetylamino-2-carboxy)-ethylthiol}]methyl-5-oxo-5-phenylpentanoic Acid (Compound 38D)

(1) Preparation of 4-(1-piperazinyl)methyl-5-oxo-5-phenylpentanoic acid (Compound 38D-A)

4-Benzoylbutyric acid (1000.9 mg, 5.21 mmols) was suspended in a formalin aqueous solution (507 mg, 6.25 mmols) and piperidine (532 mg, 6.25 mmols). The reaction was carried out at 100° C. for 3 hours and a half. Piperidine (517 mg, 6.07 mmols) was added thereto and the mixture was heated to 100° C. for further 3 hours. After air-cooling to room temperature, the reaction mixture was concentrated in vacuo. The residue was purified by silica gel column chromatography (100 ml, dichloromethane:methanol=10:1 to 5:1) to give Compound (38D-A) (1500.8 mg, yield: 99%).

1H-NMR (200 MHz, CDCl3) δ: 1.2–1.8 (8H, m), 2.10 (1H, m), 2.42 (1H, m), 2.5–3.0 (4H, m), 3.16 (1H, dd, J=2.0 Hz, 12.7 Hz), 3.38 (4H, m), 3.16 (1H, dd, J=2.0 Hz, 12.7 Hz), 3.38 (1H, dd, J=8.1 Hz, 12.5 Hz), 4.37 (1H, m), 7.2–7.4 (2H, m), 7.46 (1H, t, J=7.4 Hz), 8.41 (2H, d, J=7.2 Hz), 9.30 (1H, br).

MS (FAB, POS) m/z: 290 (M+H)+.

(2) Preparation of 4-[(2R)-{(2-acetylamino-2-carboxy)ethylthiol}]methyl-5-oxo-5-phenylpentanoic acid (Compound 38D)

Compound (38D-A) (576.0 mg, 1.99 mmol) and (R)-N-acetylcysteine (324.7 mg, 1.99 mmol) were dissolved in ethanol (5 ml). The solution was heated to reflux for 4 hours. After air-cooling, the mixture was concentrated in vacuo.

The residue was purified by silica gel column chromatography (100 ml, chloroform:methanol=10:1 to 3:1) to give Compound (38D) (417.4 mg, yield: 57%).

1H-NMR (200 MHz, DMSO-d6) δ: 1.7–2.0 (2H, m), 1.83 (3H, d, J=2 Hz), 2.20 (2H, t, J=7.3 Hz), 2.6–3.0 (4H, m), 3.86 (1H, m), 4.33 (1H, dt, J=4.8 Hz, 7.4 Hz), 7.5–7.7 (3H, m), 8.00 (2H, dd, J=7.0 Hz, 2.2 Hz), 8.09 (1H, d, J-7.3 Hz).

MS (FAB, NEG) m/z: 366 (M–H)+.

EXAMPLE 34

Preparation of (1R,2S)-2-[N-(panthoyl--alanylamido)ethylthio]methyl-3-oxo-1-cyclopentanecarboxylic Acid (Compound 1E)

A 100 ml aliquot of seed culture medium (2.0% glycerin, 1.0% glucose, 0.5% soybean meal, 0.3% peptone, 0.5% yeast extract, 0.2% calcium carbonate, 0.05% dipotassium phosphate and 0.05% magnesium sulfate; pH 7.0) was charged in an rotary shaker Erlenmeyer flask of 500 ml volume and sterilized at 120° C. for 20 minutes in an autoclave. One platinum loop of strain NA32176 (FERM P-16372) was inoculated to the medium and cultured at 27 C for 2 days at 220 rpm.

In main culture, a 100 ml aliquot of culture medium (1.0% glucose, 4.0% starch syrup, 1.0% corn steep liquor, 0.2% yeast extract, 1.0% gluten meal, 0.00011% iron sulfate heptahydrate, 0.00064% copper sulfate pentahydrate, 0.00015% zinc sulfate heptahydrate, 0.00079% manganese chloride tetrahydrate, 0.0001% cobalt chloride and 0.2% calcium carbonate; pH 7.0) was charged in a rotary shaker Erlenmeyer flask of 500 ml volume, which had been sterilized at 120° C. for 20 minutes in an autoclave. One milliliter of the above seed culture broth was inoculated to the main medium charged in the flask and cultured at 27° C. for 2 days, at 220 rpm.

The cultured broth (10 L) was filtered in a conventional manner to separate the filtrate and the mycelial cake.

After the pH was adjusted to 8 with 4N sodium hydroxide, the filtrate was applied to a DIAION HP-20 column (1 L), and then washed. Elution was performed by a linear gradient from water (2 L) to 80% methanol (2 L). After methanol was removed, the pH of the eluted fraction was adjusted to 2 with 1N hydrochloric acid. Extraction with n-butanol followed.

The n-butanol layer was concentrate in vacuo. The residue (491 mg) was applied to Sephadex LH-20 column chromatography (fai 3.5×90 cm, moving phase: methanol). The active fraction (267 mg) thus obtained was dissolved in a mixture of ethyl acetate-water (1:1). The solution was then subjected to centrifugal liquid-liquid partition chromatography (volume of 250 ml, 1500 rpm, flow rate: 3 ml/min)—the lower phase of the mixture was previously seed to operate as the fixing phase). After washing with the upper phase liquid of the mixture, the active fraction was reversely eluted by the lower phase to give the crude active substance (16 mg). The crude substance was purified by Sephadex LH-20 column chromatography (fai 1.8×85 cm, moving phase:methanol) to give NA32176A (Compound E) (13 mg).

The appearance, molecular weight, solubility, Rf value by ODS thin layer chromatography, UV absorption spectrum, IR absorption spectrum, $^1$H-NMR spectrum and $^{13}$C-NMR spectrum of NA32176A (Compound 1E) purified as above were determined. The physicochemical properties of NA32176A (Compound 1E) were found to be as described above.

EXAMPLE 35

Preparation of 4-oxo-4-phenyl-3-(1-piperidyl)-methylbutyric acid (Compound 1F)

Compound (1F) may be prepared by a known process, e.g., described in J. Chem. Soc. (C), 2308 (1967).

EXAMPLE 36

Preparation of 4-(4-methylphenyl)-4-oxo-3-(1-piperidyl)methylbutyric Acid (Compound 2F)

Piperidine (1027 mg, 12.07 mmols) and 37% formaldehyde aqueous solution (0.98 ml, 12.07 mmols) were added to 4-(4-methylphenyl)-4-oxobutyric Acid (2320 mg, 12.07 mmols). The reaction solution was heated to become homogeneous. The reaction solution was then stirred at room temperature for 15 hours and concentrated in vacuo. The residue was purified by silica gel column chromatography (chloroform:methanol=20:1 to 10:1) to give Compound (2F) (745 mg, yield: 22.6%).

1H-NMR (60 MHz, CDCl3) δ: 1.66–2.36 (6H, m), 2.50–3.05 (2H, m), 2.85 (3H, s), 3.60 (2H, m), 4.70 (1H, m), 7.61 (2H, d, J=9.1 Hz), 8.30 (2H, d, J=9.1 Hz), 10.3 (1H, brs); MS (FAB, POS) m/z: 274 (M+H)+.

EXAMPLE 37

Preparation of 4-(4-methoxyphenyl)-4-oxo-3-(1-piperidyl)methylbutyric Acid (Compound 3F)

Piperidine (851 mg, 10 mmols) and 37% formaldehyde aqueous solution (0.81 ml, 10 mmols) were added to 4-(4-methoxyphenyl)-4-oxobutyric Acid (2080 mg, 10 mmols). The mixture was heated to become homogeneous. The reaction solution was stirred at room temperature for 3 hours and concentrated in vacuo. The residue was purified by silica gel column chromatography (250 ml, chloroform:methanol=20:1 to 10:1) to give Compound (3F) (552 mg, yield: 19%).

1H-NMR (60 MHz, CDCl3) δ: 1.60–2.48 (6H, m), 2.66–3.30 (2H, m), 3.16–3.50 (4H, m), 3.70 (3H, m), 4.33 (3H, m), 4.80 (1H, m), 7.35 (2H, d, J=9.5 Hz), 8.50 (2H, d, J=9.5 Hz), 11.40 (1H, brs); MS (FAB, POS) m/z: 290 (M+H)+.

EXAMPLE 38

Preparation of 4-oxo-4-phenyl-3-(1-pyrrolidinyl)-methylbutyric acid (Compound 4F)

Pyrrolidine (1020 mg, 14.34 mmols) and 37% formaldehyde aqueous solution (1.16 ml) were added to 4-oxo-4-phenylbutyric acid (2555 mg, 14.34 mmols). The mixture was heated to become homogeneous. The reaction solution was stirred at room temperature for 10 hours and concentrated in vacuo. A part of the residue (920 mg) was purified by silica gel column chromatography (90 ml, chloroform:methanol=5:1 to 2:1) to give Compound (4F) (372 mg, yield: 40%).

1H-NMR (60 MHz, CD3OD) δ: 2.17 (4H, m), 2.64 (2H, m), 3.30–3.72 (6H, m), 4.33 (1H, m), 7.60 (3H, m), 8.12 (2H, m); MS (FAB, POS) m/z: 262 (M+H)+.

EXAMPLE 39

Preparation of 3-(4-morpholinyl)methyl-4-oxo-4-phenylbutyric Acid (Compound 5F)

Morpholine (3891 mg, 4.47 mmols) and 37% formaldehyde solution (0.37 g, 4.47 mmols) were added to 4-oxo-4-phenylbutyric acid (797 mg, 4.47 mmols). The mixture was heated to become homogeneous. The reaction solution was stirred at room temperature for 15 hours and concentrated in vacuo. The residue was purified by silica gel column chromatography (200 ml, chloroform:methanol=10:1 to 2:1) to give Compound (5F) (510 mg, yield: 41%).

1H-NMR (200 MHz, CD3CD) δ: 2.40–3.08 (8H, m), 3.69 (4H, t, J=4.68 Hz), 4.21 (1H, m), 7.50 (3H, m), 8.00 (2H, m), 10.40 (1H, brs); MS (FAB, POS) m/z: 278 (M+H)+.

EXAMPLE 40

Preparation of 3-f1-(4-methylpiperazinyl)}methyl-4-oxo-4-phenylbutyric Acid (Compound 6F)

1-Methylpiperazine (349 mg, 3.51 mmols) and 37% formaldehyde solution (0.29 ml, 3.51 mmols) were added to 4-oxo-4-phenylbutyric acid (627 mg, 3.51 mmols). The mixture was heated to become homogeneous. The reaction solution was stirred at room temperature for 15 hours and concentrated in vacuo. The residue was purified by silica gel column chromatography (90 ml, butanol:acetic acid:water=20:1:1) and Sephadex LH-20 (250 ml, 80% hydrated methanol) to give Compound (6F) (251 mg, yield: 24.6%).

1H-NMR (60 MHz, CDCl3) δ: 2.50–3.60 (12H, m), 2.84 (3H, s), 4.50 (1H, m), 7.80 (3H, m), 8.30 (2H, m), 12.16 (1H, brs); MS (FAB, POS) m/z: 291 (M+H)+.

EXAMPLE 41

Preparation of 3-(diethylamino)methyl-4-oxo-4-phenylbutyric Acid (Compound 7F)

Diethylamine (300 mg, 4.10 mmols) and 37% formaldehyde solution (0.33 ml) were added to 4-oxo-4-phenylbutyric acid (730 mg, 4.10 mmols). The mixture was heated to become homogeneous. The reaction solution was stirred at room temperature for 16 hours and concentrated in vacuo. The residue was purified by silica gel column chromatography (90 ml, chloroform:methanol=10:1 to 5:1) to give Compound (7F) (312 mg, yield: 28.9%).

1H-NMR (60 MHz, CDCl3) δ: 1.90 (6H, t, J=6.8 Hz), 3.06–4.00 (8H, m), 4.95 (1H, m), 8.20 (3H, m), 8.72 (2H, m), 11.70 (1H, brs); MS (FAB, POS) m/z: 264 (M+H)+.

EXAMPLE 42

Preparation of (1R,2R)-3-oxo-2-(1-piperidyl)methyl-1-cyclopentanecarboxylic Acid (Compound 8F)

(1R,2S)-2-[(2RS)-(2,3-O-isopropylidene)-propylsulfonyl]methyl-3-oxo-1-cyclopentanecarboxylic acid (205 mg, 0.64 mmol) was dissolved in acetone (3 ml). To the solution, piperidine (55 mg, 0.64 mmol), methanol (2 ml) and 1N sodium hydroxide (0.45 ml) were successively added. The mixture was stirred at room temperature for 20 hours. The reaction solution was concentrated in vacuo. The residue was purified by Sephadex LH-20 (250 ml, 80% hydrated methanol) to give Compound (8F) (75 mg, yield: 52%).

MS (FAB, POS) m/z: 226 (M+H)+.

EXAMPLE 43

Preparation of 4-oxo-4-(3-pyridyl)-3-(1-piperidyl)methylbutyric Acid (Compound 12F)

(1) Preparation of methyl 4-oxo-4-(3-pyridyl)butyrate (Compound 12F-A)

In nitrogen atmosphere, a solution of 3-pyridinecarboxyaldehyde (10.7 g, 100 mmols) in anhydrous dimethylformamide (20 ml) was dropwise added to a solution of sodium cyanide (2.44 g, 50 mmols) at 30° C. in anhydrous dimethylformamide (80 ml) over 30 minutes. After stirring for 30 minutes, a solution of methyl acrylate (8.6 g, 100 mmols) in anhydrous dimethylformamide (80 ml) was dropwise added to the reaction mixture over an hour followed by stirring for 3 hours at 30° C. Acetic acid (0.66 ml) and water (30 ml) were added to the reaction solution. After stirring for 10 minutes, the mixture was concentrated in vacuo. Water (360 ml) and chloroform (300 ml×3) were added to the residue for separation. The resultant organic phase was washed with saturated sodium chloride aqueous solution (300 ml), dried over anhydrous sodium sulfate and concentrated in vacuo. The residue was purified by silica gel column chromatography (650 ml, hexane:ethyl acetate= 1:1–1:2) to give Compound (12F-A) (7.87 g, yield: 40.7%).

(2) Preparation of 4-oxo-4-(3-pyridyl)butyric acid (Compound 12F-B)

Compound (12F-A) (5.04 g, 26.11 mmols) was dissolved in methanol (60 ml). After 1N sodium hydroxide aqueous solution (32 ml) was added to the solution, the mixture was stirred for 3 hours at room temperature. Then, 2N hydrochloric acid (16 ml) was added to the reaction mixture followed by concentration in vacuo. The residue was purified by silica gel column chromatography (250 ml, chloroform:methanol:acetic acid=20:1:0.5) to give Compound (12F-B) (3.13 g, yield: 66.9%).

1H-NMR (200 MHz, CD3OD) δ: 2.72 (3H, t, J=6.5 Hz), 3.33 (3H, t, J=6.5 Hz), 7.59 (1H, m), 8.42 (1H, m), 8.73 (1H, m), 9.14 (1H, m); MS (FAB, POS) m/z: 180 (M+H)+.

(3) Preparation of 4-oxo-4-(3-pyridyl)-3-(1-piperidyl) methylbutyric acid (Compound 12F Piperidine (140 mg, 1.64 mmol) and 37% formalin (0.133 ml, 1.64 mmol) were added to Compound (12F-B) (246 mg, 1.37 mmol). The mixture was stirred at 100° C. for 2 hours. Silica gel (1.8 g) was added to the reaction solution. After concentration, the residue was purified by silica gel column chromatography (30 ml, chloroform:methanol:acetic acid= 10:1:0.5 to 10:5:3) to give Compound (12F) (300 mg, yield: 79%).

1H-NMR (200 MHz, CDCl3) δ: 1.45–1.80 (6H, m), 2.30–3.15 (8H, m), 4.28 (1H, m), 7.46 (1H, dd, J=4.7 Hz, 8.0 Hz), 8.00 (1H, brs), 8.37 (1H, dt, J=2.0 Hz, 8.0 Hz), 8.78 (1H, dd, J=1.6 Hz, J-4.8 Hz), 9.28 (1H, d, J=1.6 Hz); MS (FAB, POS) m/z: 180 (M+H)+.

EXAMPLE 44

Preparation of 4-(2-furyl)-4-oxo-3-(1-piperidyl) methylbutyric Acid (Compound 26F)

(1) Preparation of methyl 4-(2-furyl)-4-oxobutyrate (Compound 26F-A)

After 3-benzyl-5-(2-hydroxyethyl)-4-methylthiazolium chloride (1.0 g, 4 mmols) and triethylamine (2.02 g, 20 mmols) were added to a solution of furfural (4.8 g, 50 mmols) in absolute ethanol (30 ml). The mixture was stirred at room temperature for 40 minutes. Methyl acrylate (5.0 g, 50 mmols) was further added to the mixture followed by heating to reflux for 7 hours. The reaction solution was concentrated in vacuo. The residue obtained was purified by silica gel column chromatography (600 ml, hexane:ethyl acetate=2:1) to give Compound (26F-A) (3430 mg, yield: 37.6%).

1H-NMR (200 MHz, CDCl3) δ: 2.74 (2H, t, J=6.8 Hz), 3.18 (2H, t, J=6.8 Hz), 6.54 (1H, dd, J=1.7 Hz, 3.6 Hz), 7.23 (1H, dd, J=0.7 Hz, 3.6 Hz), 7.59 (1H, dd, J=0.7 Hz, 1.7 Hz); MS (FAB, POS) m/z: 180 (M+H)+.

(2) Preparation of 4-(2-furyl)-4-oxobutyric acid (Compound 26F-B)

To a solution of Compound (26F-A) (1820 mg, 10 mmols) in methanol (20 ml) was added 1N sodium hydroxide aqueous solution (10.5 ml). The mixture was stirred at room temperature for 3 hours. After concentration in vacuo, water (30 ml) and ethyl acetate (30 ml) were added to the residue for separation. The pH of the aqueous phase was adjusted to 3.0 with 2N hydrochloric acid aqueous solution followed by extraction with ethyl acetate (30 ml×2). The organic phase was washed with saturated sodium chloride aqueous solution (50 ml), dried over anhydrous sodium sulfate and concentrated in vacuo to give Compound (26F-B) (1445 mg, yield: 86%).

1H-NMR (200 MHz, CDCl3) δ: 2.77 (2H, t, J=6.6 Hz), 3.17 (2H, t, J=6.6 Hz), 6.55 (1H, dd, J=1.7 Hz, 3.7 Hz), 7.23 (1H, dd, J=0.7 Hz, 3.6 Hz), 7.59 (1H, dd, J=0.7 Hz, 1.7 Hz); MS (FAB, POS) m/z: 168 (M+H)+.

(3) Preparation of 4-(2-furyl)-4-oxo-3-(1-piperidyl) methylbutyric acid (Compound 26F)

Piperidine (797 mg, 9.36 mmol) and 37% formalin (0.76 ml, 9.36 mmols) were added to Compound (26F-B) (1431 mg, 8.51 mmols). The mixture was stirred at room temperature for 4 days. Silica gel (4.5 g) was added to the reaction solution. After concentrated in vacuo, the residue was purified by silica gel column chromatography (100 ml, chloroform:methanol:acetic acid=10:1:0.5 to 3:1:0.3) to give Compound (26F) (1325 mg, yield: 62.5%).

1H-NMR (200 MHz, CDCl3) δ: 1.56 (2H, m), 1.79 (4H, m), 2.48 (1H, dd, J=10.7 Hz, 15.5 Hz), 2.82 (5H, m), 3.16 (2H, d, J=6.2), 4.08 (1H, m), 6.60 (1H, dd, J=1.7 Hz, 3.6 Hz), 7.49 (1H, d, J=3.6 Hz), 7.66 (1H, d, J=1.6 Hz), 10.7 Hz (1H, brs); MS (FAB, NEG) m/z: 264 (M–H)–.

EXAMPLE 45

Preparation of 3-(1-piperidyl)methyl-4-oxo-4-(4'-trifluoromethylphenyl)butyric Acid (Compound 9F)

(1) Preparation of 4'-(trifluoromethyl)cinnamic acid (Compound 9F-A)

A mixture of 4'-(trifluoromethyl)acetophenone (2500.5 mg, 13.29 mmols) and glyoxylic acid monohydrate (1223.3 mg, 13.29 mmols) was reacted at 95° C. for 1 hours while sucking through an aspirator. Glyoxylic acid monohydrate (439.5 mg, 477 mole) was further added to the system and the mixture was reacted at 95° C. for 2 h while sucking through or aspirator. After cooling to room temperature, 20 ml of 5% potassium carbonate was added to the reaction solution. The mixture was extracted twice with ethyl acetate. Aqueous layer was adjusted to pH1 with 4N hydrochloric acid and then extracted with ethylacetate twice. The extract was washed with water and then saturated sodium chloride aqueous solution, dried over anhydrous sodium sulfate and concentrated in vacuo. The residue was dissolved in acetic acid (10 ml) and conc. hydrochloric acid (0.5 ml) was added to the solution. The mixture was heated to reflux for 7 hours. The reaction solution was concentrated in vacuo. The residue was dissolved in ethyl acetate. The solution was washed with water and then saturated sodium chloride aqueous solution, dried over anhydrous sodium sulfate and concentrated in vacuo. The residue was recrystallized from hexaneethyl acetate to give Compound (9F-A) (1554.5 mg, yield: 48%).

1H-NMR (60 MHz, CD3OD) δ: 6.93 (1H, d, J=15 Hz), 7.83 (2H, d, J=10 Hz), 8.00 (1H, d, J=15 Hz), 8.14 (2H, d, J=10 Hz)

(2) Preparation of 4-(4'-(trifluoromethylphenyl)-butyric acid (Compound 9F-B)

Compound (9F-A) (1036.9 mg, 4.25 mmols) was dissolved in acetic acid (9 ml) and water (2 ml). Zinc powders (320.1 mg, 4.89 mmols) were added to the solution. The mixture was stirred at room temperature for 4 hours. After filtering through celite, the filtrate was concentrated in vacuo. The residue was suspended in ethyl acetate and purified to give Compound (9F-B) (1111.0 mg, 100%).

1H-NMR (200 MHz, DMSO-d6) δ: 3.22 (2H, t, J=6.3 Hz), 3.37 (br), 7.88 (2H, d, J=8.3 Hz), 8.15 (2H, d, J=8.3 Hz).

(3) Preparation of 3-(1-piperidyl)methyl-4-oxo-4-(4'-trifluoromethylphenyl)butyric acid (Compound 9F)

Compound (9F-B) (1005.7 mg, 4.08 mmols) was dissolved in dimethylsulfoxide (10 ml). Formalin aqueous solution (507 mg, 6.25 mmols) and piperidine (532 mg, 6.25 mmols) was added to the solution. The mixture was reacted at 100° C. for 24 hours. After ice-cooling, the precipitates were filtered off. The filtrate was separated with water and ethyl acetate. After the aqueous phase was extracted with ethyl acetate, the combined organic layers were washed with saturated sodium chloride aqueous solution and concentrated in vacuo. The residue was purified by silica gel column chromatography (200 ml, chloroform methanol=5:1 to 1:2) to give Compound (9F) (312.5 mg, yield: 22%).

1H-NMR (200 MHz, DMSO-d6) δ: 1.4–1.0 (6H, m), 2.36 (1H, dd, J=10.1 Hz, 15.2 Hz), 2.70 (1H, dd, J=15.3 Hz, 2.4 Hz), 2.7–3.0 (4H, m), 3.26 (2H, d, J=6.2 Hz), 4.40 (1H, m), 7.78 (2H, d, J=8.5 Hz), 8.24 (2H, d, J=8.1 Hz). MS (FAB, NEG) m/z: 343 (M).

EXAMPLE 46

Preparation of 2-methyl-4-oxo-4-phenyl-3-(1-piperazinyl)methylbutyric Acid (Compound 41F)

2-Methyl-4-oxo-4-phenylbutyric acid (1000.5 mg, 5.21 mmols) was suspended in formalin aqueous solution (507 mg, 6.25 mmols) and piperidine (532 mg, 6.25 mmols). Ethanol (6 ml) was further added to the suspension. The reaction was conducted at 100° C. for 40 minutes. The crystals obtained by filtration with heating were dried to give Compound (41F) (529.2 mg, yield: 35%).

MS (FAB, POS) m/z: 290 (M+H)+.

EXAMPLE 47

Preparation of 4-(1-piperazinyl)methyl-5-oxo-5-phenylpentanoic Acid (Compound 42F)

4-Benzoylbutyric acid (1000.9 mg, 5.21 mmols) was suspended in a formalin aqueous solution (507 mg, 6.25 mmols) and piperidine (532 mg, 6.25 mmols). The reaction was carried out at 100° C. for 3 hours and a half. Piperidine (517 mg, 6.07 mmols) was added thereto and the mixture was heated to 100° C. for further 3 hours. After air-cooling to room temperature, the reaction mixture was concentrated in vacuo. The residue was purified by silica gel column chromatography (100 ml, dichloromethane: L=10:1 to 5:1) to give Compound (42F) (1500.8 mg, yield: 99%).

1H-NMR (200 MHz, CdCl3) δ: 1.2–1.8 (8H, m), 2.10 (1H, m), 2.42 (1H, m), 2.5–3.0 (4H, m), 3.16 (1H, dd, J=2.0 Hz, 12.7 Hz), 3.38 (1H, dd, J=8.1 Hz, 12.5 Hz), 4.37 (1H, m), 7.2–7.4 (2H, m), 7.46 (1H, t, J=7.4 Hz), 8.41 (2H, d, J=7.2 Hz), 9.30 (1H, br). MS (FAB, OOS) m/z: 290 (M+H)+.

Test Example 1
Neuron-like neurite extension effect of the compounds of this invention on PC12 cells The effect of the compounds of the invention was examined by a modification of the method of Green et al., Ann. Rev. Neurosci., 3, 353, 1980, and evaluated in terms of morphological change of PC12 cells and a level of the change. That is, PC12 cells were inoculated on Dulbecco-modified Eagle's medium supplemented with 10% calf fetal serum and 10% equine serum in approximately 100,000 cells/ml. The cells were incubated at 37° C. overnight in 5% $CO_2$ using collagen-coated 96 well multiplates. Morphological change of the cells was microscopically observed one day after the test compound was added to each well under this conditions.

The minimum effective dose (MED, g/ml) of each compound on PC12 cells that caused neuron-like neurite extension is shown in Table 2 below.

TABLE 2

Minimum effective dose to cause neuron-like neurite extension on PC12 cells

| Compound No. | MED (g/ml) |
|---|---|
| 1A | 3.2 |
| 2A | 3.2 |
| 6A | 25 |
| 1B | 3.2 |
| 2B | 1.6 |
| 3B | 3.2 |
| 4B | 3.2 |
| 5B | 0.8 |
| 6B | 1.6 |
| 7B | 3.1 |
| 8B | 0.8 |
| 9B | 6.3 |
| 13B | 1.6 |
| 14B | 3.1 |
| 15B | 3.1 |
| 2C | 6.3 |
| 1D | 25 |
| 2D | 13 |
| 3D | 0.8 |
| 4D | 13 |
| 5D | 50 |
| 6D | 50 |
| 7D | 13 |
| 8D | 6.3 |
| 9D | 50 |
| 10D | 100 |
| 11D | 13 |
| 12D | 13 |
| 13D | 13 |
| 32D | 3.1 |
| 38D | 6.3 |
| 1E | 1.2 |
| 1F | 1.6 |
| 2F | 3.1 |
| 3F | 3.1 |
| 4F | 1.6 |
| 5F | 3.1 |
| 6F | 3.1 |
| 7F | 1.6 |
| 8F | 1.6 |
| 12F | 3.1 |
| 26F | 3.1 |
| 9F | 0.8 |
| 41F | 6.3 |
| 42F | 1.6 |

Industrial Applicability

The compounds of the present invention or pharmacologically acceptable salts thereof exhibit a potent neuron differentiation accelerating activity. The pharmaceutical compositions comprising these compounds or pharmacologically acceptable salts thereof are thus useful as neuron differentiation accelerators and effectively applicable as medicaments for the treatment of central or nervous system disorders.

What is claimed is:

1. A ketone derivative of formula [1D]:

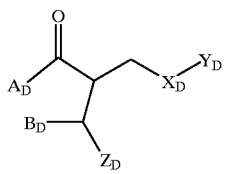

wherein:
- $A_D$ is an unsubstituted or substituted aromatic hydrocarbon, heterocyclic ring or saturated heterocyclic ring;
- $B_D$ is hydrogen or an unsubstituted aliphatic hydrocarbon group having 1 to 4 carbon atoms;
- $X_D$ is O, S, SO, $SO_2$ or NH;
- $Y_D$ is a substituted or unsubstituted aliphatic hydrocarbon group having 1 to 6 carbon atoms or a substituted or unsubstituted aromatic hydrocarbon group or monocyclic aromatic heterocyclic ring having 3 to 6 carbon atoms;
- $Z_D$ is carboxy or a group derived therefrom, an unsubstituted or substituted alkyl or alkenyl having 1 to 4 carbon atoms; or a pharmacologically acceptable salt thereof.

2. A ketone derivative of formula [1D] or a pharmacologically acceptable salt thereof, according to claim 1, wherein:
- $A_D$ is an unsubstituted or substituted aromatic hydrocarbon, aromatic heterocyclic ring or saturated heterocyclic ring;
- $B_D$ is hydrogen or an unsubstituted aliphatic hydrocarbon group having 1 to 4 carbon atoms;
- $X_D$ is S, O or SO;
- $Y_D$ is an aliphatic hydrocarbon group having 1 to 6 carbon atoms (wherein at least one hydrogen is substituted with carboxy or a group derived therefrom, amino or a group derived therefrom, or, hydroxy or a group derived therefrom; and,
- $Z_D$ is carboxy or a group derived therefrom.

3. A ketone derivative of formula [1D] or a pharmacologically acceptable salt thereof, according to claim 2, wherein:
- $A_D$ is an unsubstituted benzene ring wherein, when substituted, 1 to 3 hydrogen atoms are substituted with an unsubstituted alkyl group having 1 to 4 carbon atoms, a halogen, an alkoxy having 1 to 4 carbon atoms, or trifluoromethyl;
- $B_D$ is hydrogen or an aliphatic hydrocarbon group having 1 to 4 carbon atoms;
- $X_D$ is S, O or SO;
- $Y_D$ is an aliphatic hydrocarbon group having 1 to 6 carbon atoms (wherein at least one hydrogen is substituted with carboxy, COOR1 (wherein R1 is a substituted or unsubstituted alkyl or alkenyl having 1 to 4 carbon atoms), CONR2R3 (wherein each of R2 and R3, which may be the same or different and independently represents hydrogen or an unsubstituted or substituted alkyl having 1 to 4 carbon atoms), COW (wherein W is a heterocyclic ring which may be unsubstituted or substituted with carboxy or a group derived therefrom or, amino or a group derived therefrom), or NR4R5 (wherein each of R4 and R5, which may be the same or different, and independently represents hydrogen, an unsubstituted or substituted alkyl group having 1 to 4 carbon atoms or, an unsubstituted or substituted acyl having 1 to 5 carbon atoms) and,
- $Z_D$ is carboxy, COOR7 (wherein R7 is an unsubstituted or substituted alkyl group having 1 to 4 carbon atoms), CONR8R9 (wherein each of R8 and R9, which may be the same or different and independently represents hydrogen or an unsubstituted or substituted alkyl having 1 to 4 carbon atoms).

4. A ketone derivative of formula [1D] or a pharmacologically acceptable salt thereof, according to claim 3, wherein:
- $A_D$ is an unsubstituted or substituted benzene ring, wherein, when substituted, 1 to 3 hydrogen atoms are substituted with methyl, methoxy, methoxycarbonyl, nitro, cyano, a halogen or trifluoromethyl;
- $B_D$ is hydrogen or an alkyl having 1 to 4 carbon atoms;
- $X_D$ is S;
- $Y_D$ is an aliphatic hydrocarbon group having 1 to 6 carbon atoms (wherein at least two hydrogen atoms are substituted with carboxy, COOR1' (wherein R1' is an alkyl or alkenyl having 1 to 4 carbon atoms), NHCOR14 (wherein R14 is an alkyl having 1 to 4 carbon atoms which hydrogen may optionally be substituted with fluorine), hydroxy or OCOR15 (wherein R15 is an alkyl having 1 to 4 carbon atoms);
- $Z_D$ is carboxy, COOR7' (wherein R7' is an alkyl having 1 to 4 carbon atoms) or $CH_2OR10'$ (wherein R10' is hydrogen or an acyl having 1 to 5 carbon atoms).

5. A ketone derivative of formula [1D] or a pharmacologically acceptable salt thereof, according to claim 4, wherein:
- $A_D$ is an unsubstituted benzene ring or a benzene ring substituted with methyl or methoxy;
- $B_D$ is hydrogen;
- $X_D$ is S;
- $Y_D$ is 2-acetylamino-2-carboxyethyl, 2-acetylamino-2-methoxycarbonylethyl or 2-acetylaminoethyl; and,
- $Z_D$ is carboxy, methoxycarbonyl, acetoxymethyl or hydroxymethyl.

6. A ketone derivative of formula [1D] or a pharmacologically acceptable salt thereof, according to claim 2, wherein:
- $A_D$ is an unsubstituted or substituted aromatic heterocyclic ring;
- $B_D$ is hydrogen or an aliphatic hydrocarbon group having 1 to 4 carbon atoms;
- $X_D$ is S, O, or SO;
- $Y_D$ is an aliphatic hydrocarbon group having 1 to 6 carbon atoms (wherein at least one hydrogen is substituted with carboxy, COOR1 (wherein R1 is a substituted or unsubstituted alkyl or alkenyl having 1 to 4 carbon atoms), CONR2R3 (wherein each of R2 and R3, which may be the same or different and independently represents hydrogen or an unsubstituted or substituted alkyl having 1 to 4 carbon atoms), COW (wherein W is a heterocyclic ring which may be unsubstituted or substituted with carboxy or a group derived therefrom or, amino or a group derived therefrom), or NR4R5 (wherein each of R4 and R5, which may be the same or different, and independently represents hydrogen, an unsubstituted or substituted alkyl group having 1 to 4 carbon atoms or, an unsubstituted or substituted acyl having 1 to 5 carbon atoms) and, $Z_D$ is carboxy, COOR7 (wherein R7 is an unsubstituted or substituted alkyl group having 1 to 4 carbon atoms), CONR8R9 (wherein each of R8 and R9, which may be the same or different and independently represents hydrogen or an unsubstituted or substituted alkyl having 1 to 4 carbon atoms).

7. A ketone derivative of formula [1D] or a pharmacologically acceptable salt thereof, according to claim 6, wherein:

$A_D$ is an unsubstituted aromatic heterocyclic ring;

$B_D$ is hydrogen or an alkyl having 1 to 4 carbon atoms;

$X_D$ is S;

$Y_D$ is an aliphatic hydrocarbon group having 1 to 6 carbon atoms (wherein at least two hydrogen atoms are substituted with carboxy, COOR1' (wherein R1' is an alkyl or alkenyl having 1 to 4 carbon atoms), NHCOR14 (wherein R14 is an alkyl having 1 to 4 carbon atoms which hydrogen may optionally be substituted with fluorine), hydroxy or OCOR15 (wherein R15 is an alkyl group having 1 to 4 carbon atoms);

$Z_D$ is carboxy, COOR7' (wherein R7' is an alkyl group having 1 to 4 carbon atoms) or CH$_2$OR10' (wherein R10' is hydrogen or an acyl having 1 to 5 carbon atoms).

8. A ketone derivative of formula [1D] or a pharmacologically acceptable salt thereof, according to claim 7, wherein:

$A_D$ is 3-pyridyl;

$B_D$ is hydrogen;

$X_D$ is S;

$Y_D$ is 2-acetylamino-2-carboxyethyl, 2-acetylamino-2-methoxycarbonylethyl; and $Z_D$ is carboxy.

9. A pharmaceutical composition comprising as an effective ingredient a ketone derivative of formula [1D] according to claim 1 or a ketone derivative according to any one of claims 2 to 5 and 6 to 8, or a pharmacologically acceptable salt thereof.

10. A composition for the treatment of central nervous disorders comprising as an effective ingredient a ketone derivative of formula [1D] according to claim 1 or a ketone derivative according to any one of claims 2 to 5 and 6 to 8, or a pharmacologically acceptable salt thereof.

11. A composition for the treatment of peripheral nervous disorders comprising as an effective ingredient a ketone derivative of formula [1D] according to claim 1 or a ketone derivative according to any one of claims 2 to 5 and 6 to 8, or a pharmacologically acceptable salt thereof.

12. A composition for the treatment of promoting nerve cell differentiation comprising as an effective ingredient a ketone derivative of formula [1D] according to claim 1 or a ketone derivative according to any one of claims 2 to 5 and 6 to 8, or a pharmacologically acceptable salt thereof.

* * * * *